(12) United States Patent
Horne

(10) Patent No.: US 12,090,313 B2
(45) Date of Patent: Sep. 17, 2024

(54) EXPANDABLE MECHANICAL HEMODYNAMIC SUPPORT SYSTEMS, DEVICES, AND METHODS

(71) Applicant: Narwhal Medical LLC, Minneapolis, MN (US)

(72) Inventor: Loïc Van Horne, Minneapolis, MN (US)

(73) Assignee: Narwhal Medical LLC, Minneapolis, MN (US)

( * ) Notice: Subject to any disclaimer, the term of this patent is extended or adjusted under 35 U.S.C. 154(b) by 0 days.

(21) Appl. No.: 18/108,409

(22) Filed: Feb. 10, 2023

(65) Prior Publication Data
US 2023/0256229 A1 Aug. 17, 2023

Related U.S. Application Data

(60) Provisional application No. 63/414,581, filed on Oct. 10, 2022, provisional application No. 63/309,829, filed on Feb. 14, 2022.

(51) Int. Cl.

| | | |
|---|---|---|
| *A61M 60/806* | (2021.01) | |
| *A61M 60/13* | (2021.01) | |
| *A61M 60/174* | (2021.01) | |
| *A61M 60/178* | (2021.01) | |
| *A61M 60/216* | (2021.01) | |

(Continued)

(52) U.S. Cl.
CPC .......... *A61M 60/178* (2021.01); *A61M 60/13* (2021.01); *A61M 60/174* (2021.01);
(Continued)

(58) Field of Classification Search
CPC . A61M 60/808; A61M 60/148; A61M 60/414
See application file for complete search history.

(56) References Cited

U.S. PATENT DOCUMENTS

| | | |
|---|---|---|
| 10,905,808 B2 | 2/2021 | Tuval et al. |
| 10,994,120 B2 | 5/2021 | Tuval et al. |

(Continued)

FOREIGN PATENT DOCUMENTS

| | | |
|---|---|---|
| WO | WO 00/19097 | 4/2000 |
| WO | WO 03/103745 A2 | 12/2003 |

OTHER PUBLICATIONS

PCT International Search Report and Written Opinion in International Appln. No. PCT/US23/62417, mailed on Aug. 25, 2023, 18 pages.

(Continued)

*Primary Examiner* — Michael J D'Abreu
(74) *Attorney, Agent, or Firm* — Fish & Richardson P.C.

(57) ABSTRACT

Some embodiments of percutaneous ventricular assist devices have a two-part design that includes a housing component and a separately deployable rotatable inner catheter component. The housing component can include an expandable pump housing. The inner catheter can include an expandable pump impeller and an associated flexible drive shaft. The drive shaft can be coupled to a motor located external to the patient. The motor can rotate the drive shaft to spin the pump impeller inside of the pump housing, causing blood to be pumped within the patient. In some embodiments, the pump impeller is inflatable or self-expandable. The two-part percutaneous ventricular assist devices with inflatable or self-expandable pump impellers are designed to have very small delivery profiles. Accordingly, various deployment modalities, including radial artery deployment, are practicable using the two-part percutaneous ventricular assist devices described herein.

10 Claims, 63 Drawing Sheets

(51) Int. Cl.
  *A61M 60/226* (2021.01)
  *A61M 60/414* (2021.01)
  *A61M 60/416* (2021.01)
  *A61M 60/538* (2021.01)
  *A61M 60/585* (2021.01)
  *A61M 60/808* (2021.01)
  *A61M 60/81* (2021.01)
  *A61M 60/824* (2021.01)
  *A61M 60/841* (2021.01)

(52) U.S. Cl.
  CPC ........ *A61M 60/216* (2021.01); *A61M 60/226* (2021.01); *A61M 60/414* (2021.01); *A61M 60/416* (2021.01); *A61M 60/538* (2021.01); *A61M 60/585* (2021.01); *A61M 60/808* (2021.01); *A61M 60/81* (2021.01); *A61M 60/824* (2021.01); *A61M 60/841* (2021.01)

(56) References Cited

U.S. PATENT DOCUMENTS

| | | |
|---|---|---|
| 2003/0135086 A1 | 7/2003 | Khaw et al. |
| 2011/0071338 A1 | 3/2011 | McBride et al. |
| 2011/0257462 A1* | 10/2011 | Rodefeld ............ A61M 60/216 600/16 |
| 2013/0303831 A1* | 11/2013 | Evans ................. A61M 60/237 600/16 |
| 2016/0101224 A1 | 4/2016 | Akkerman et al. |
| 2021/0170081 A1 | 6/2021 | Kanz |

OTHER PUBLICATIONS

PCT Invitation to Pay Additional Fees in International Appln. No. PCT/US23/62417, mailed on May 23, 2023, 2 pages.

* cited by examiner

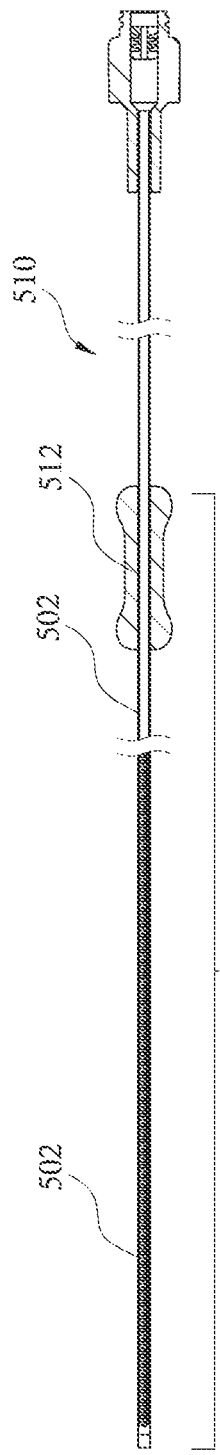
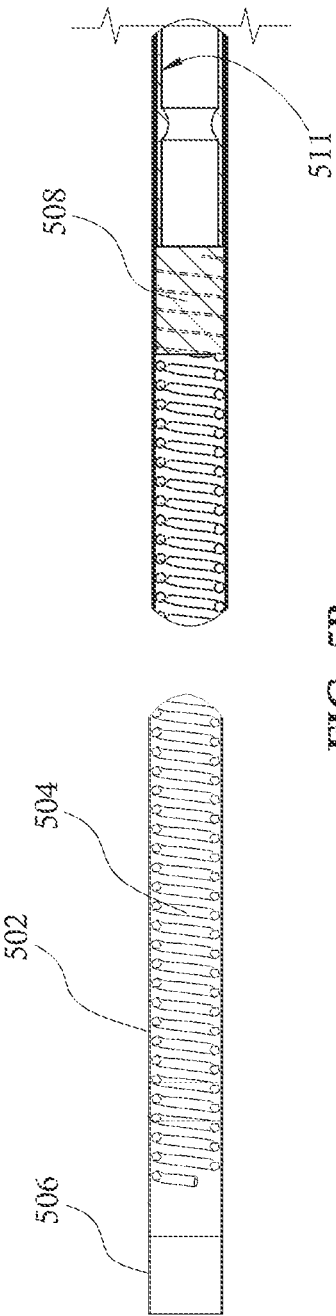

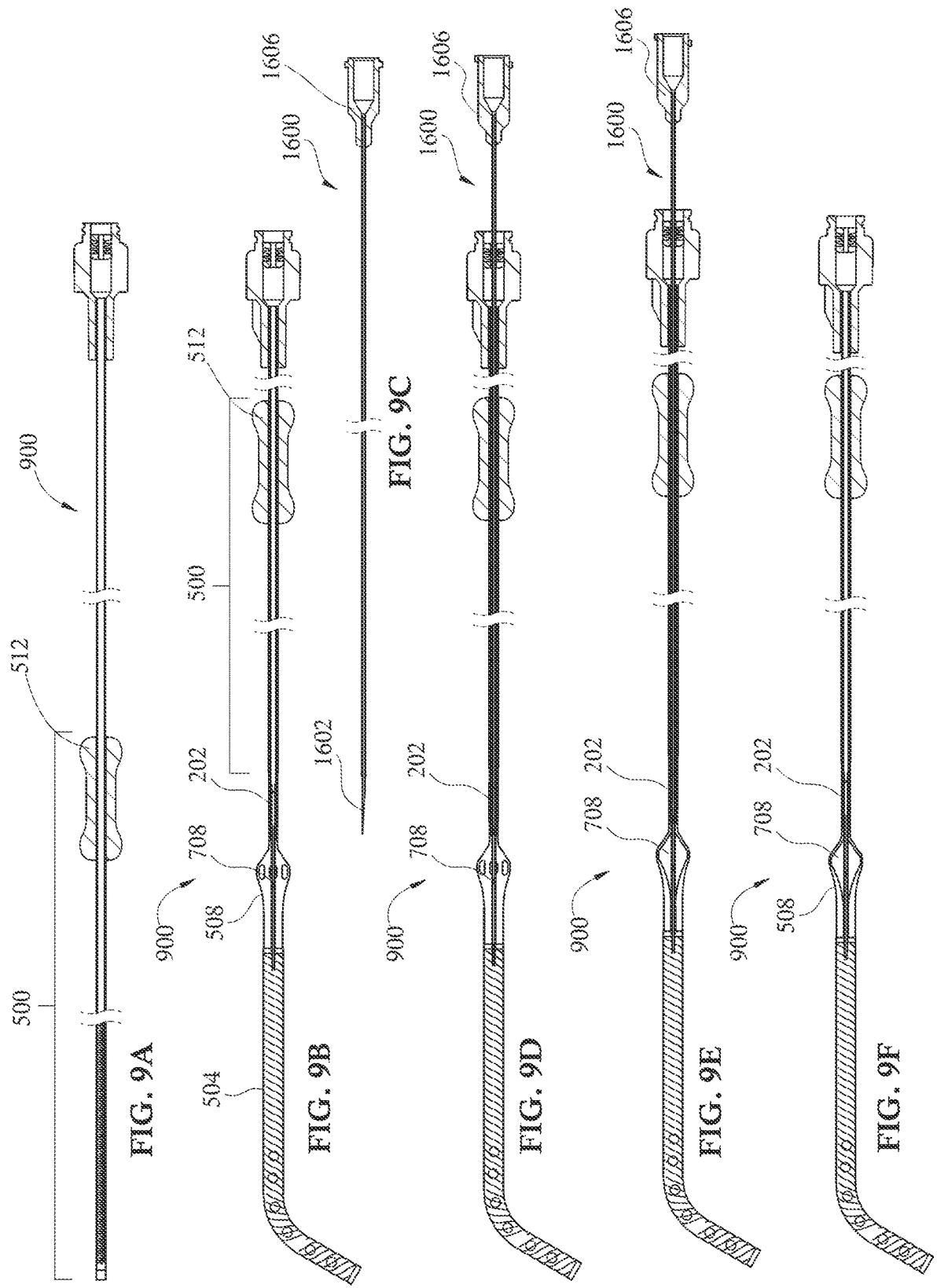

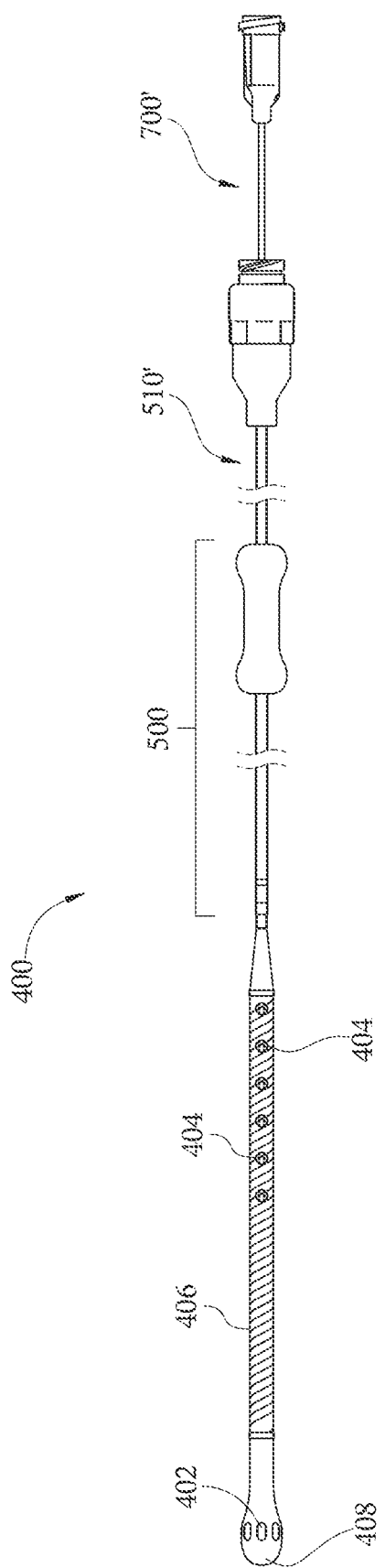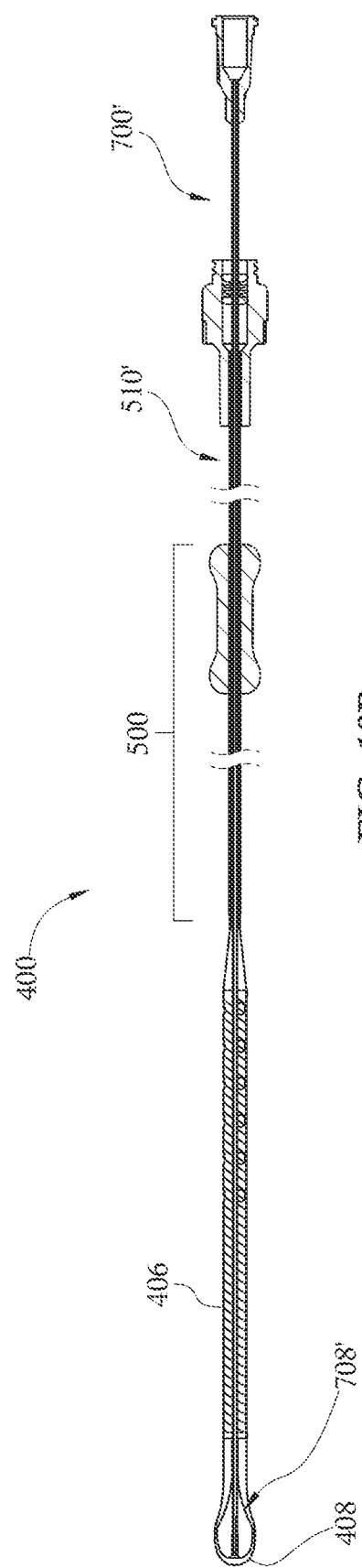
FIG. 10A
FIG. 10B

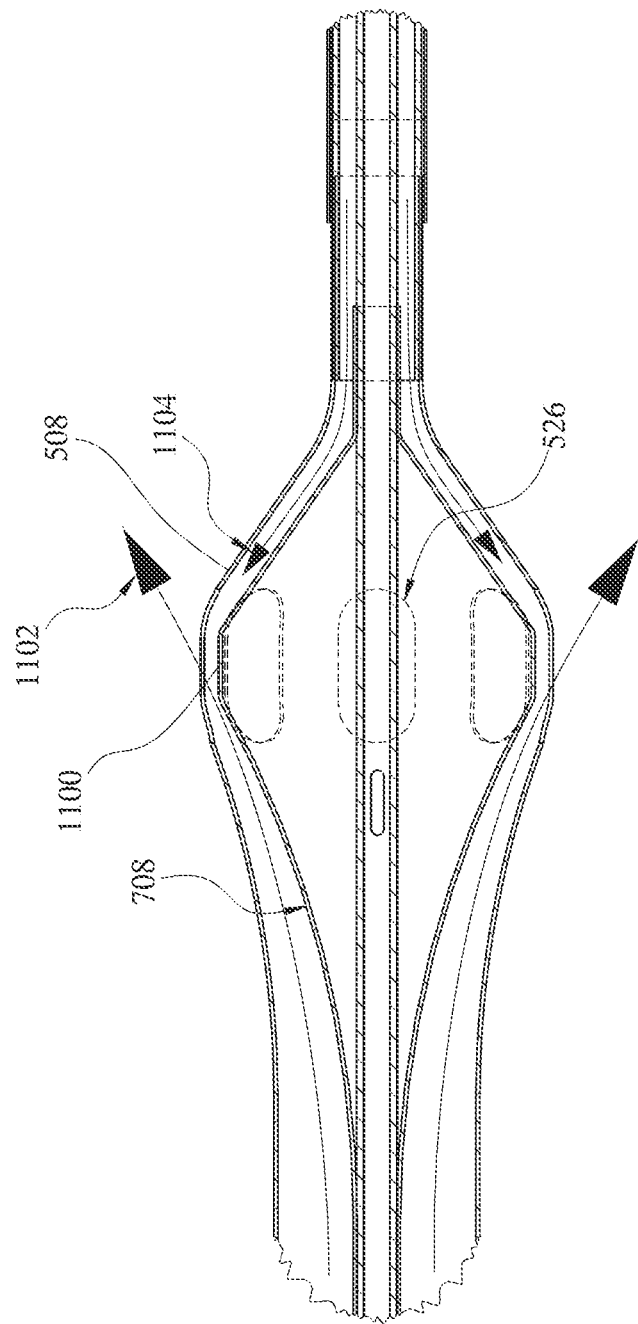

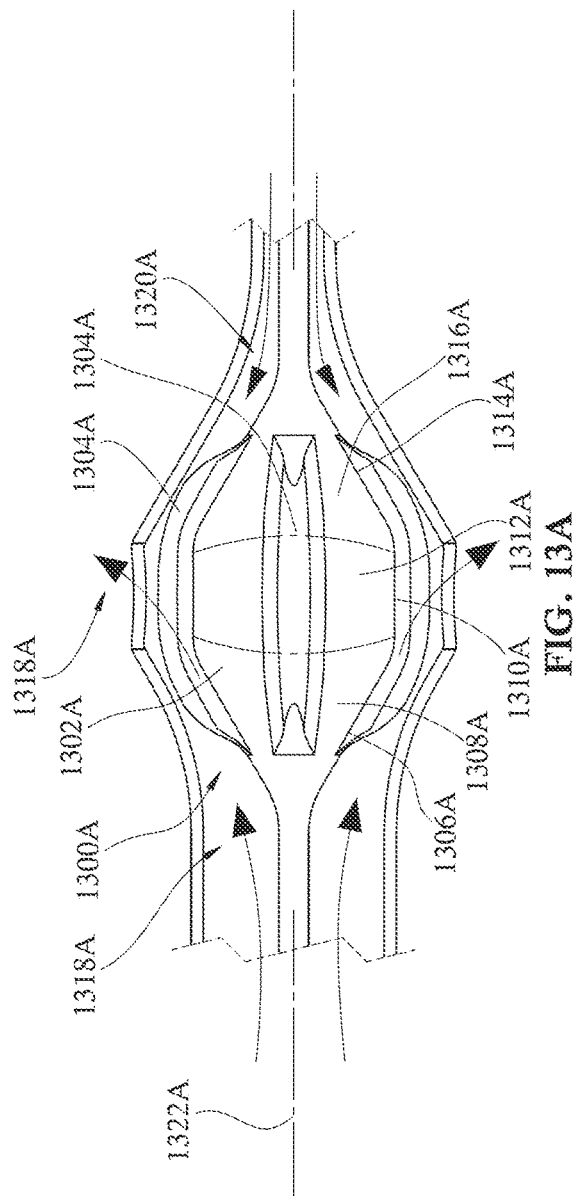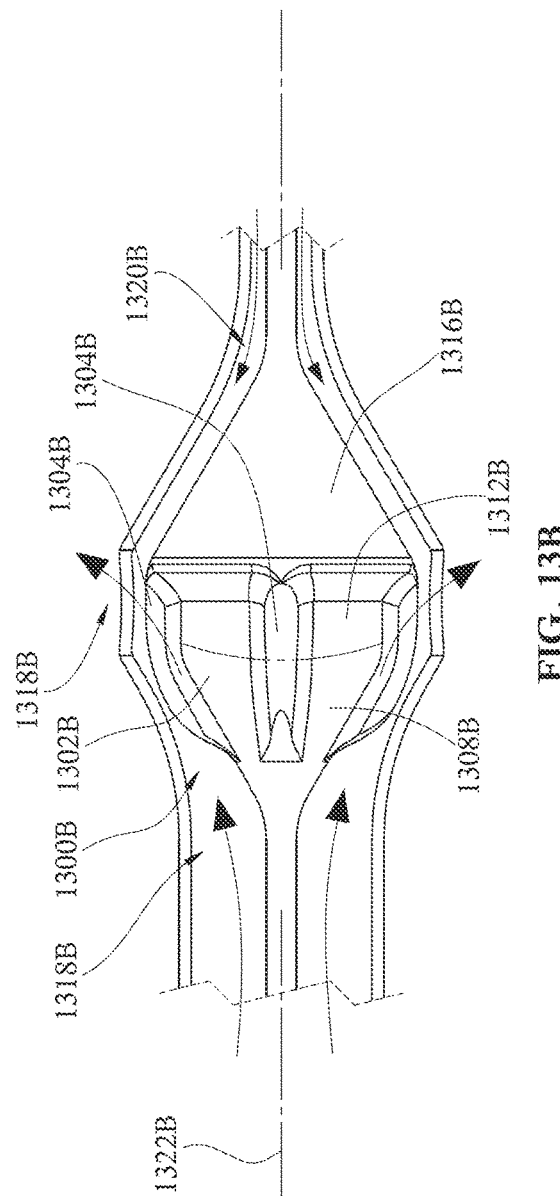

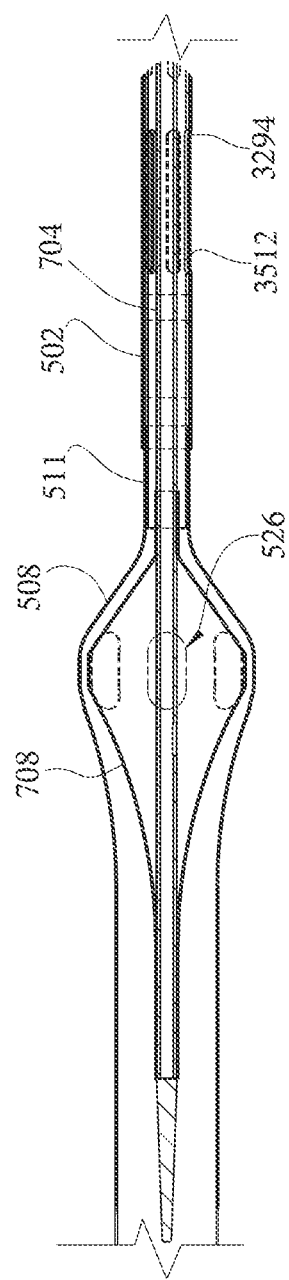
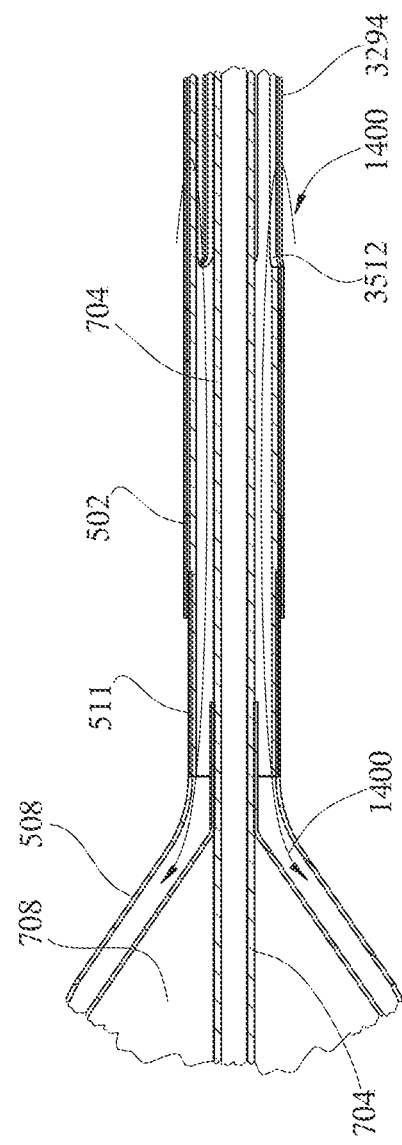
FIG. 14A
FIG. 14B

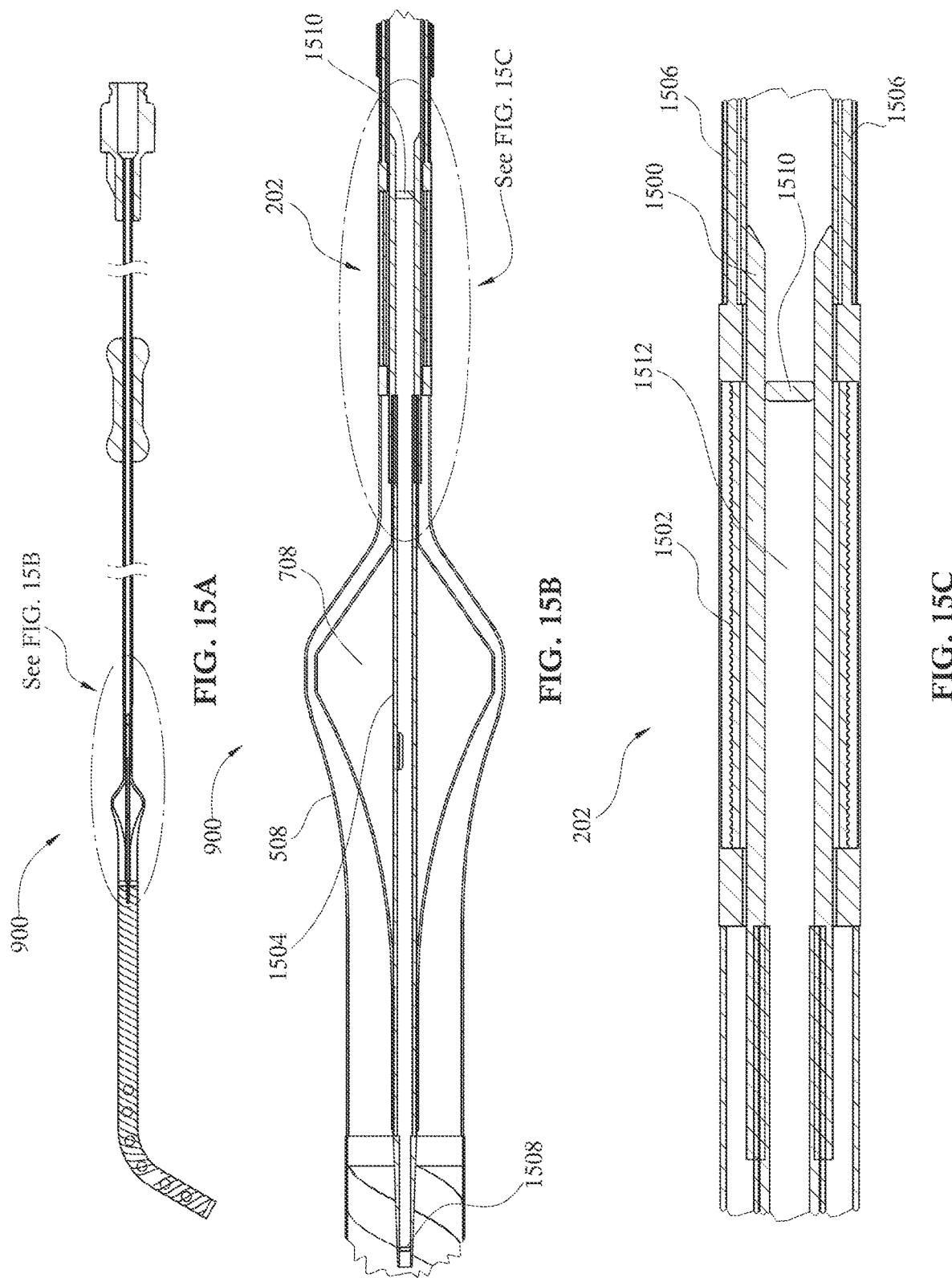

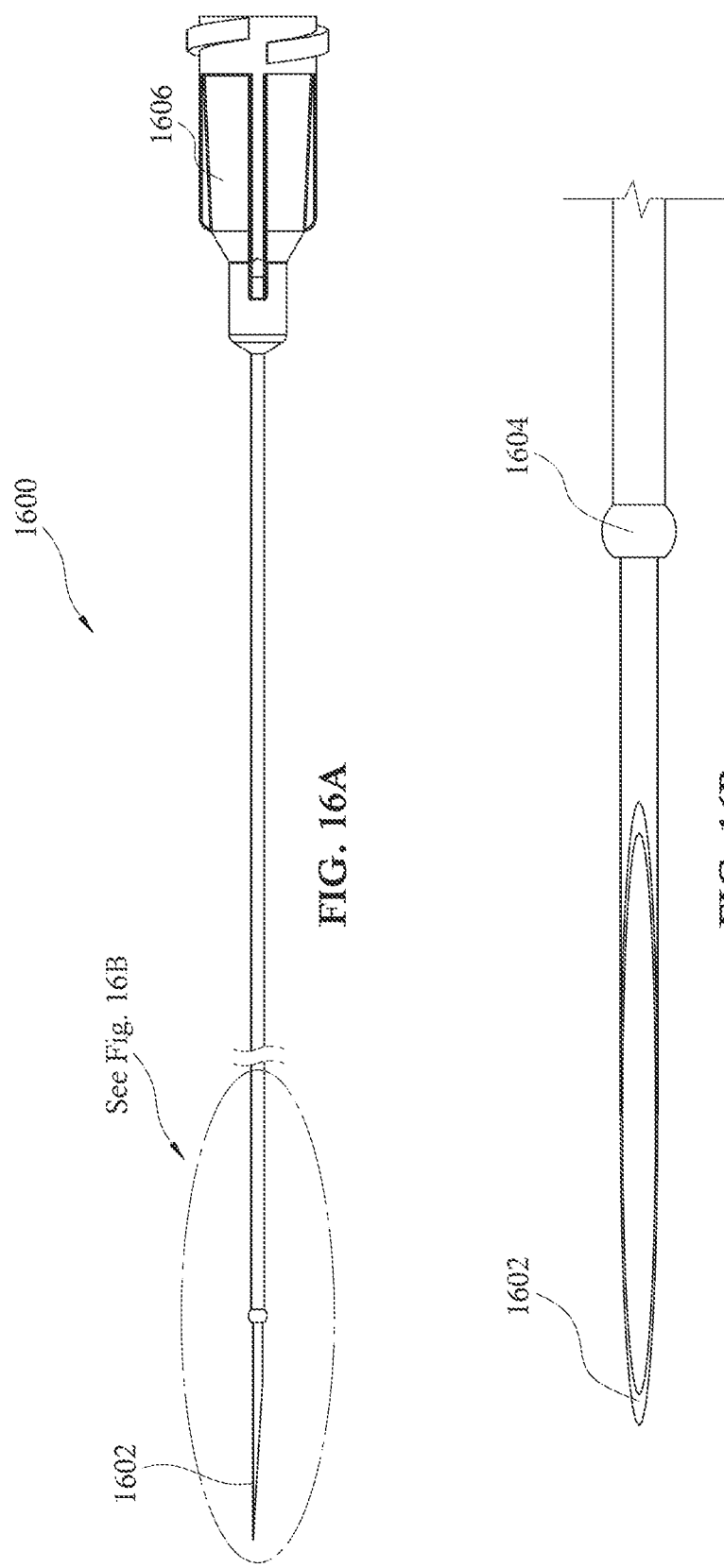

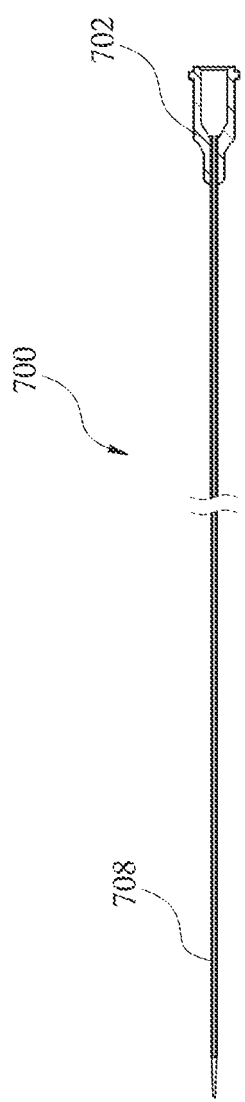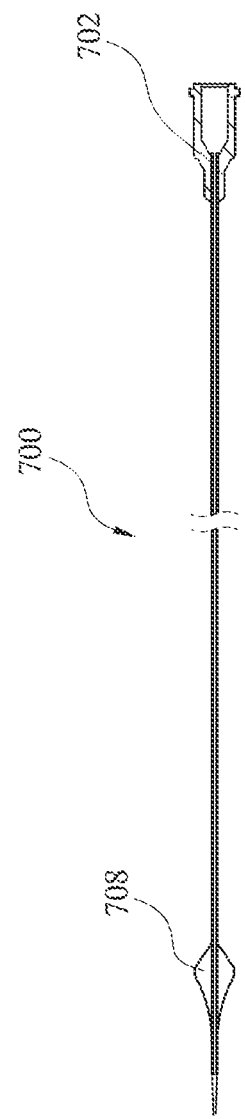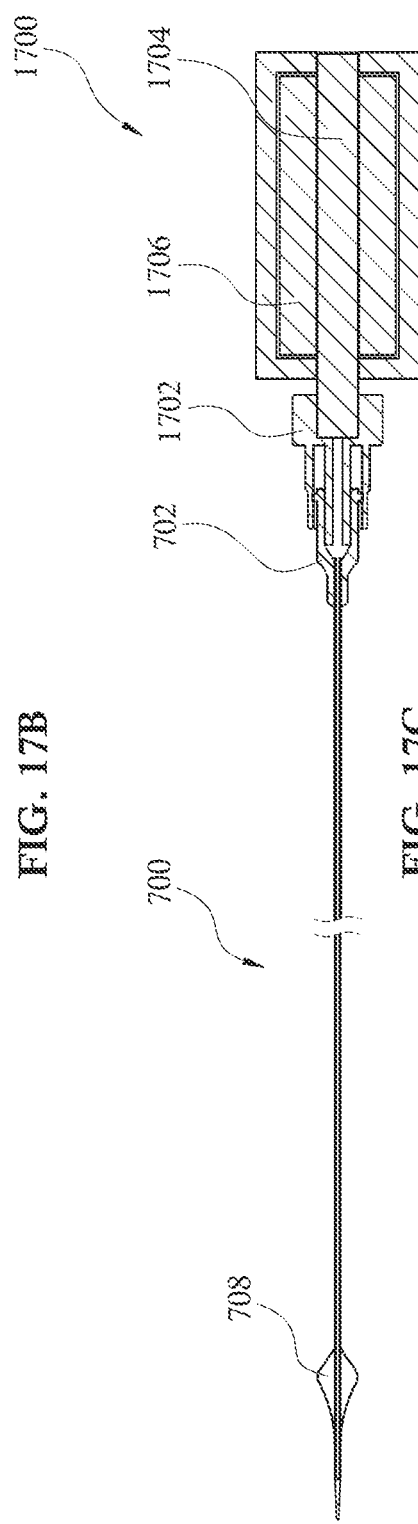

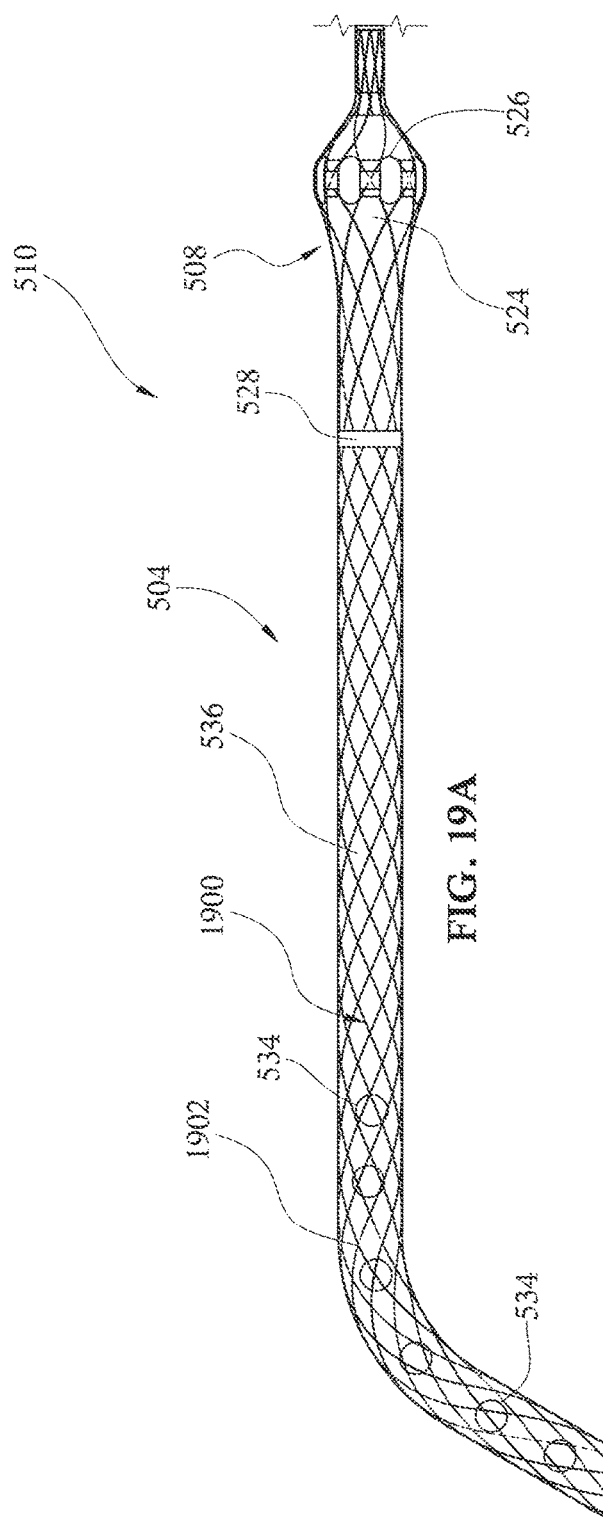
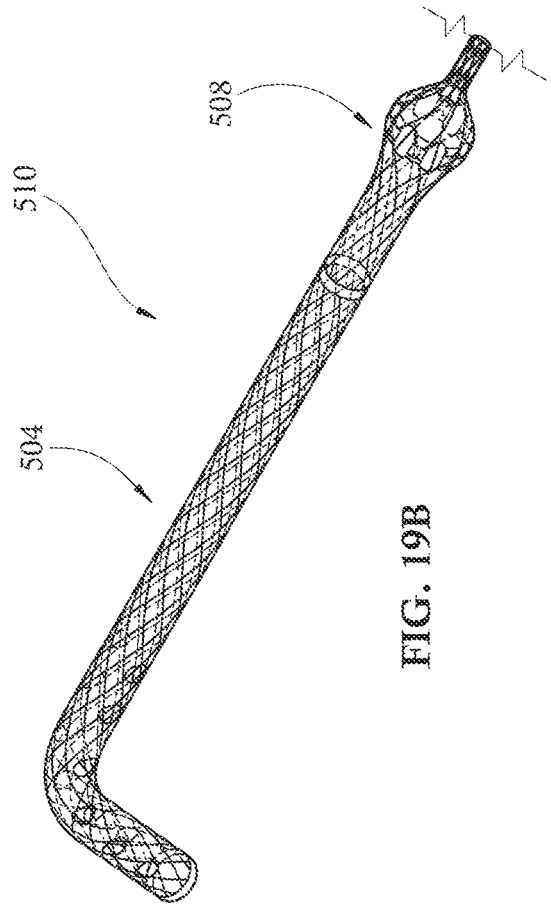
FIG. 19A
FIG. 19B

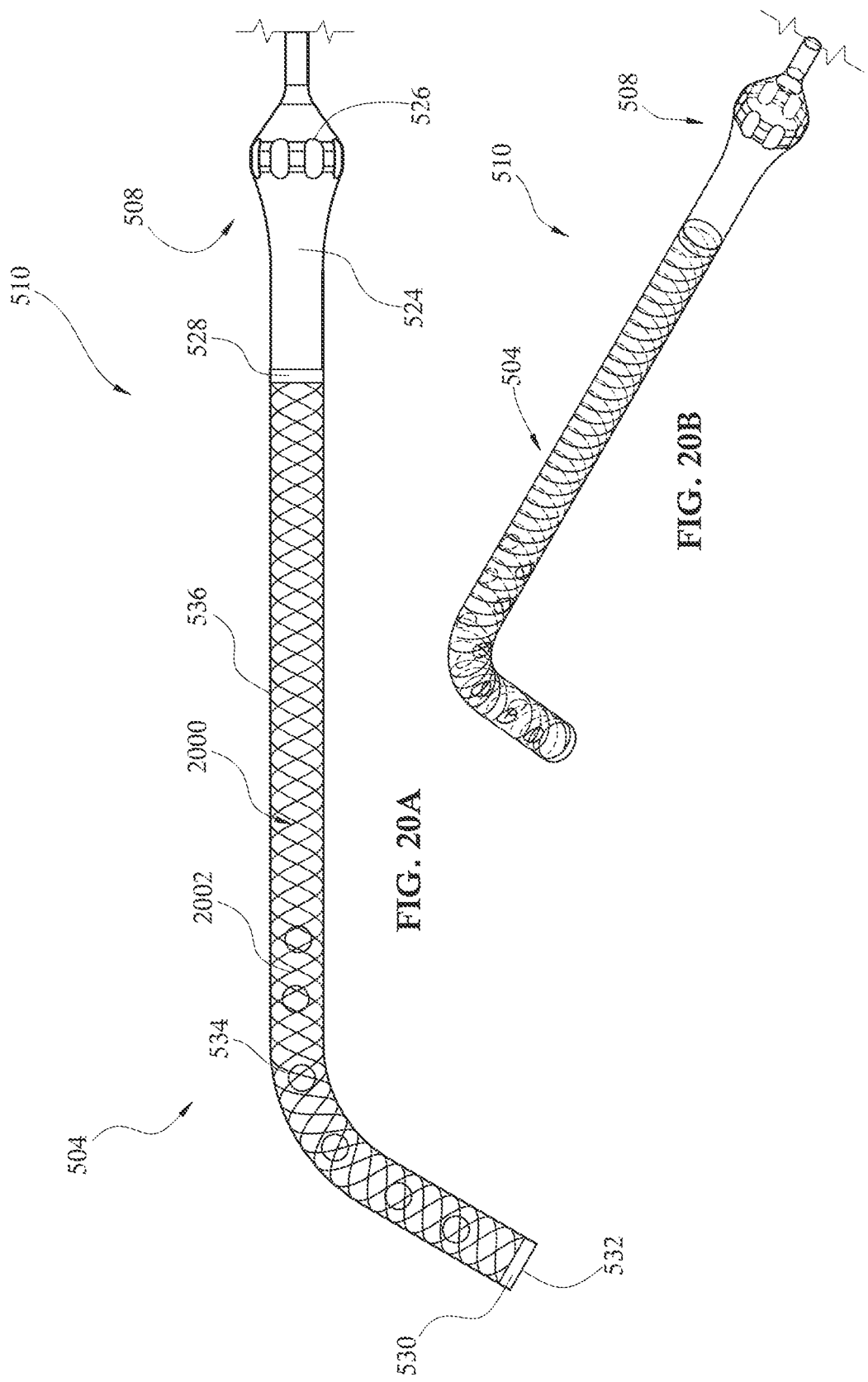

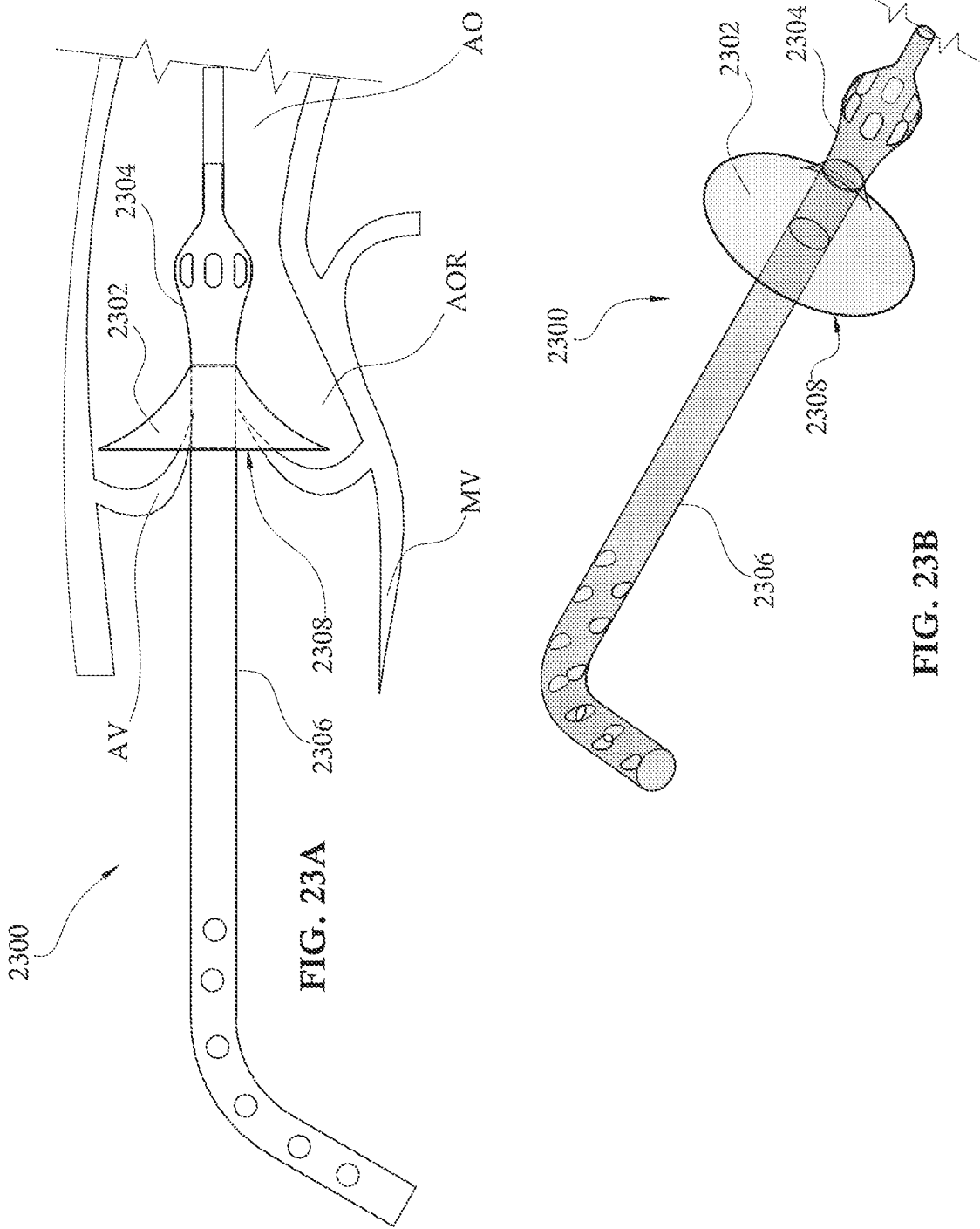

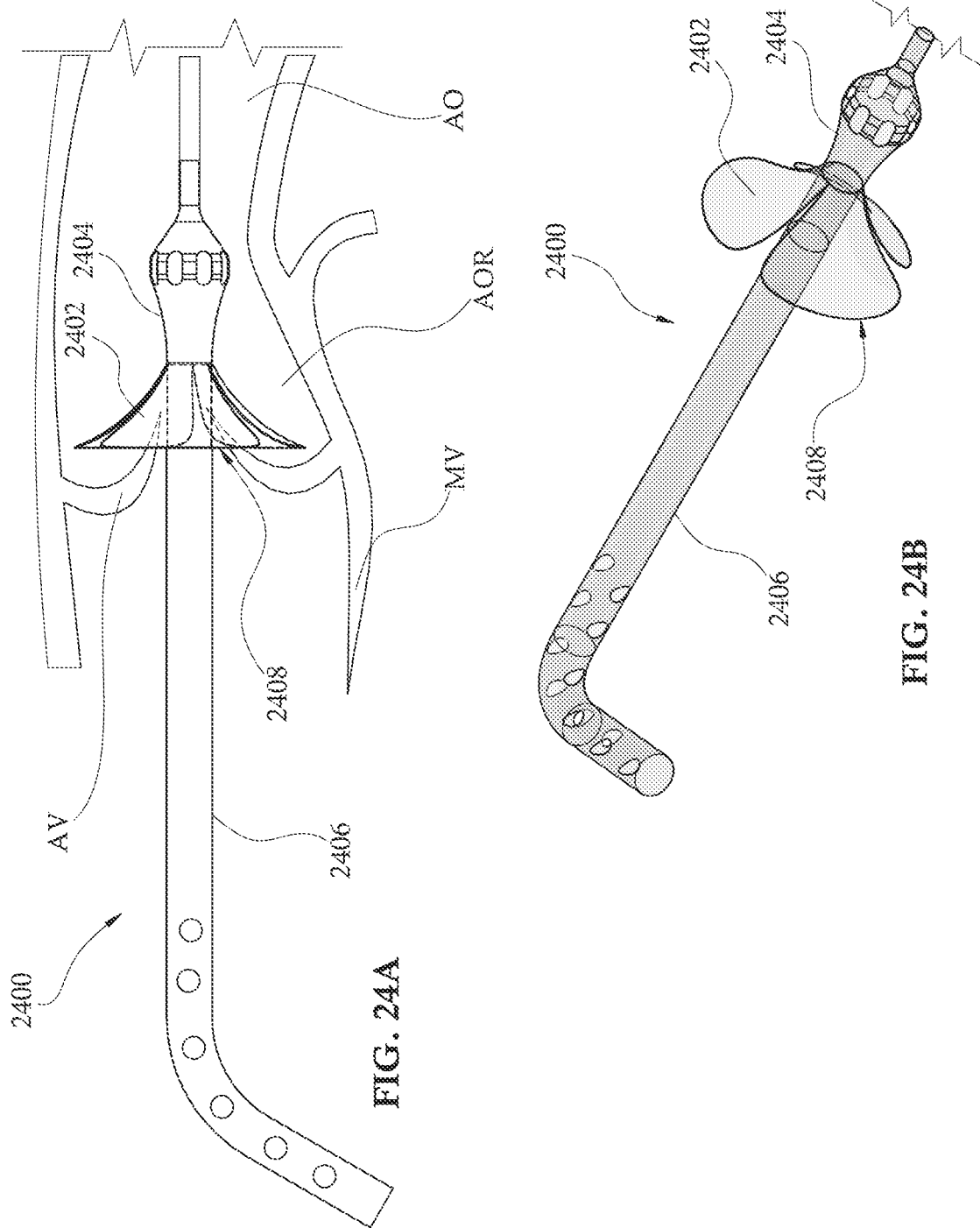

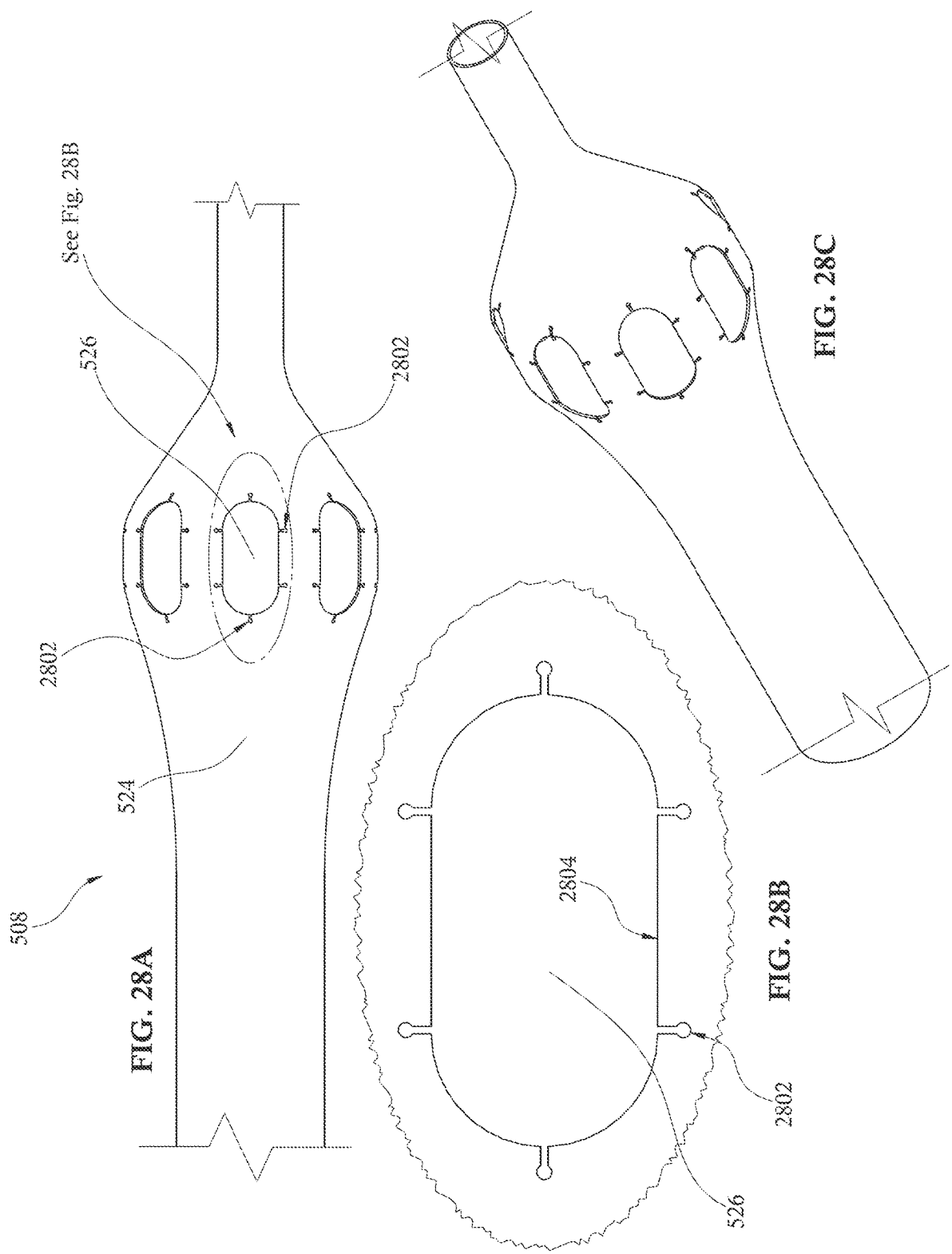

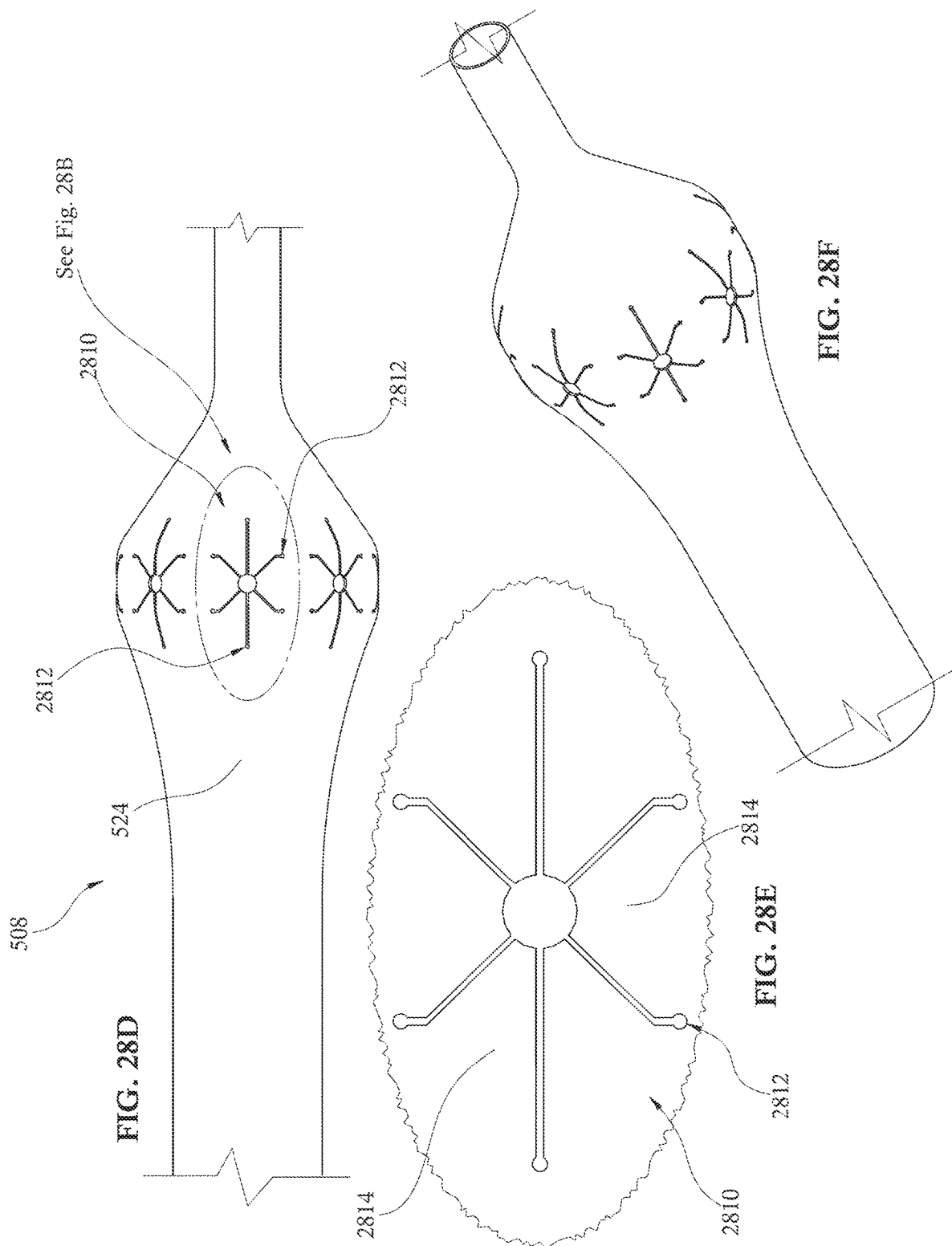

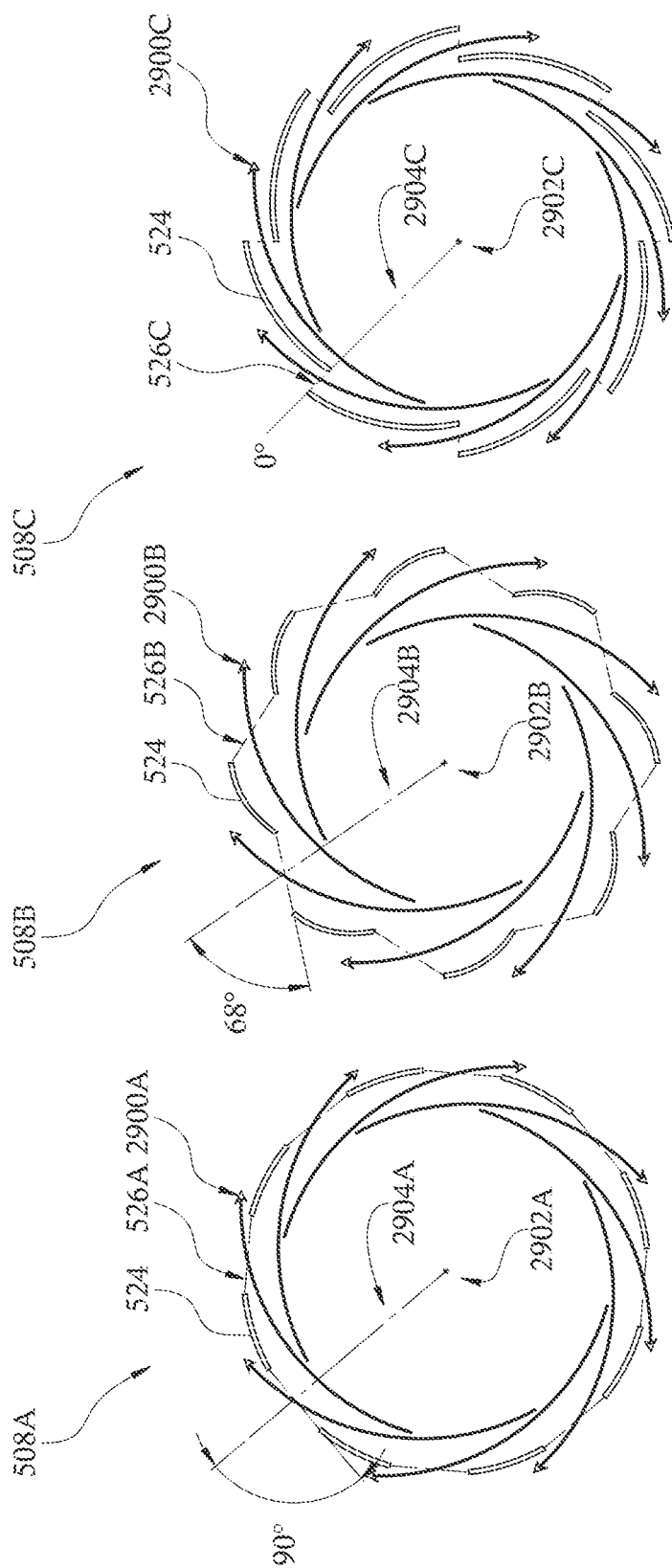

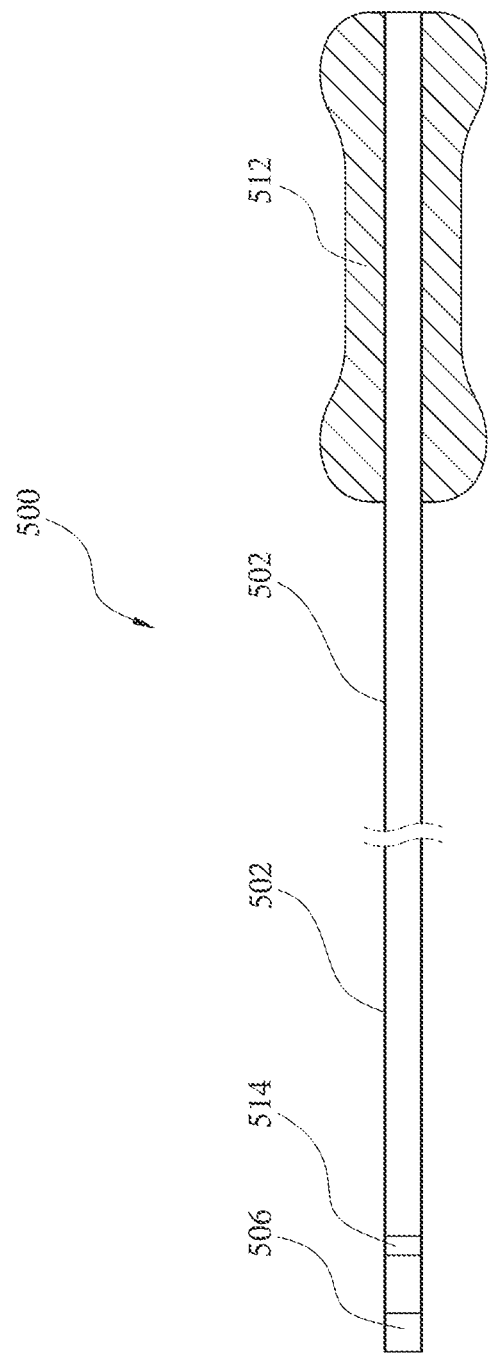

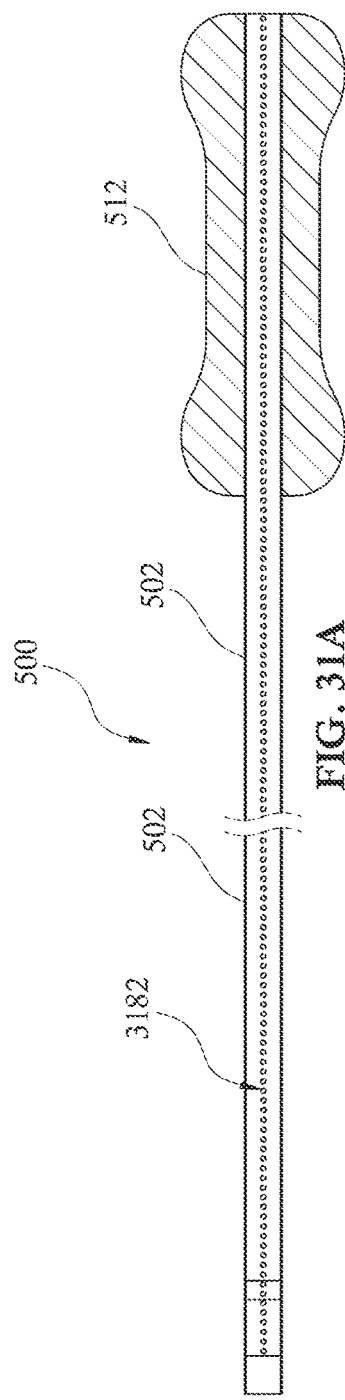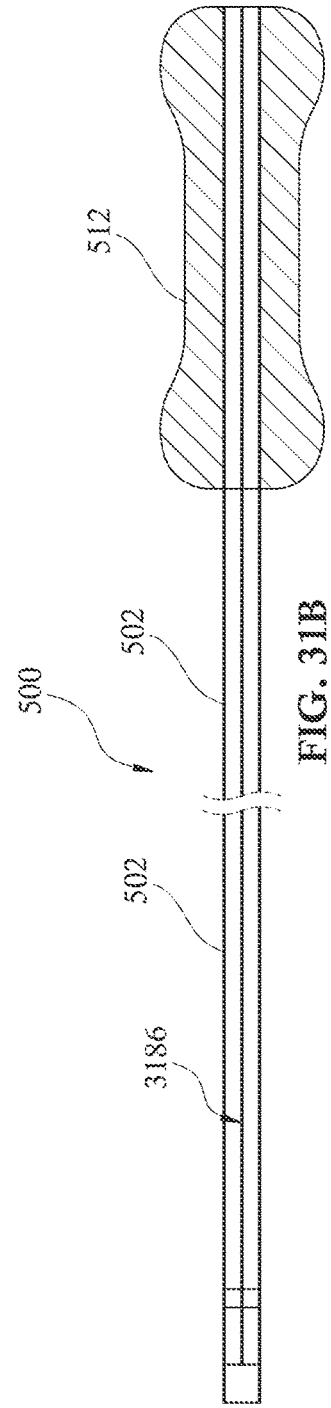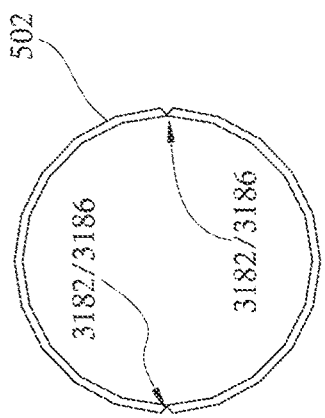

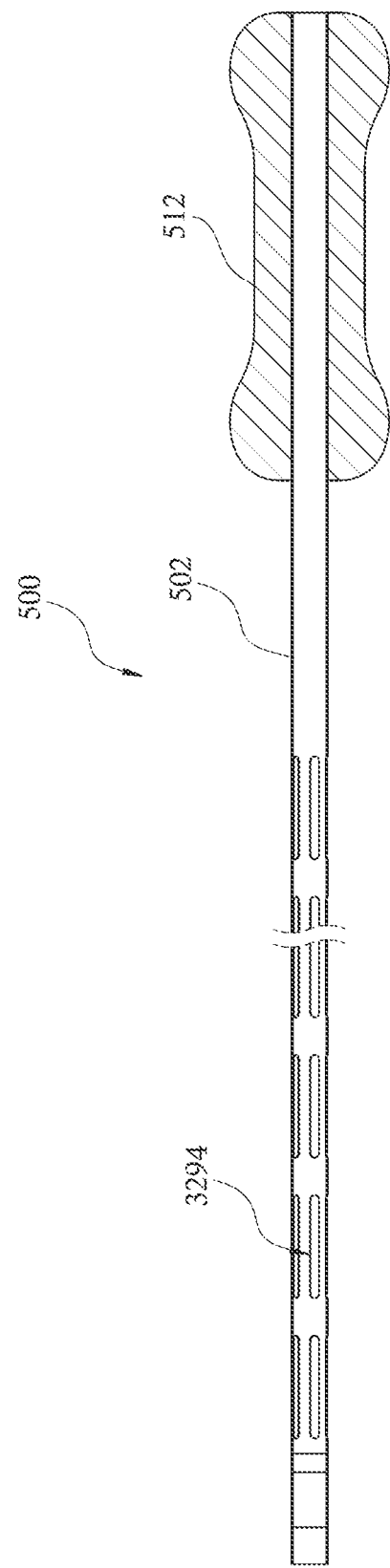

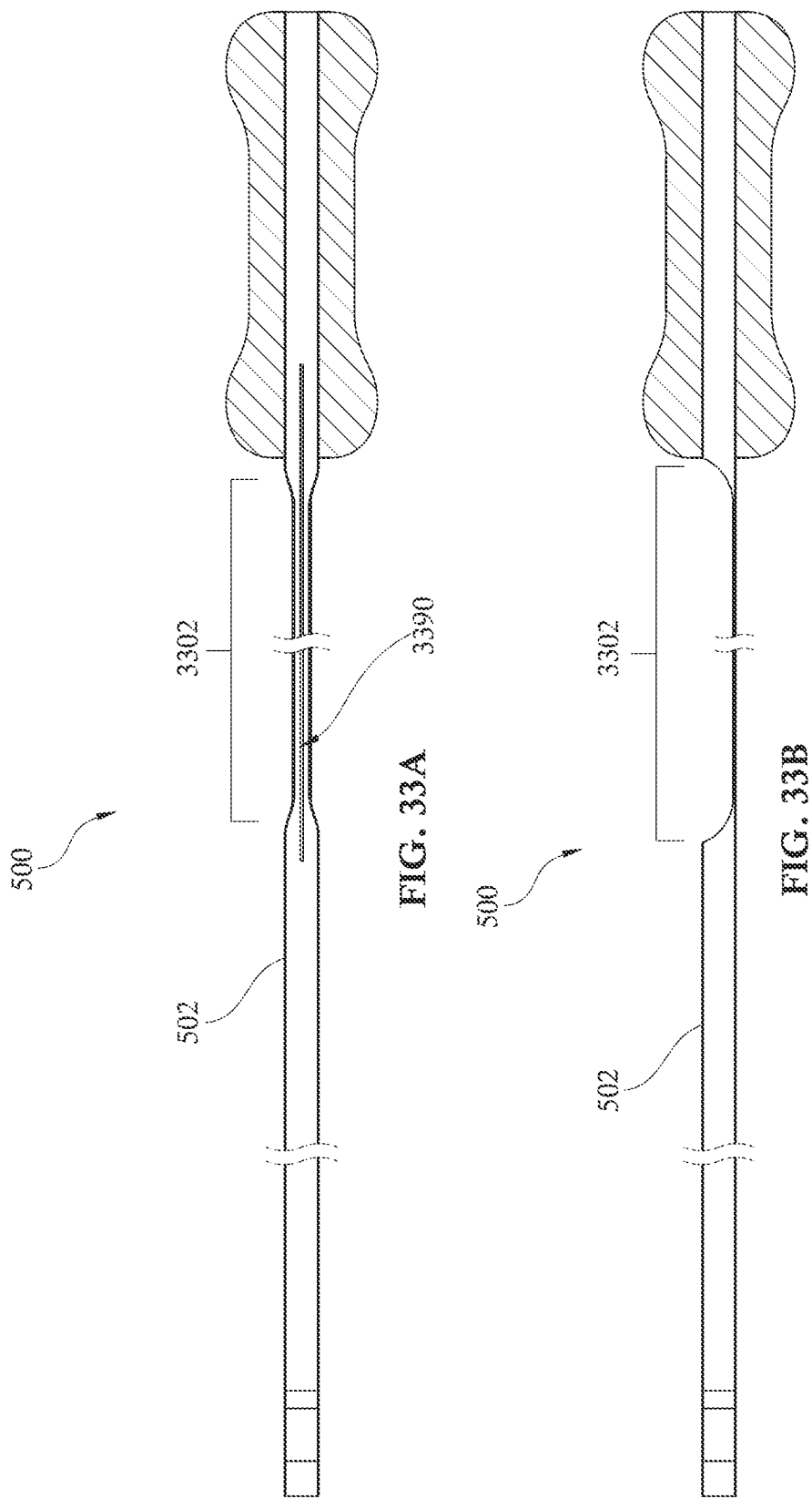

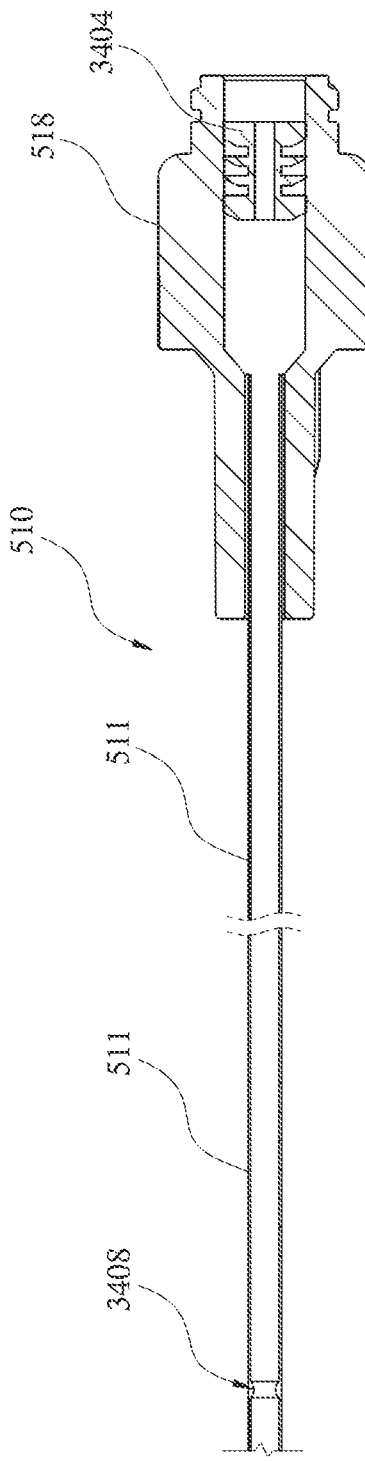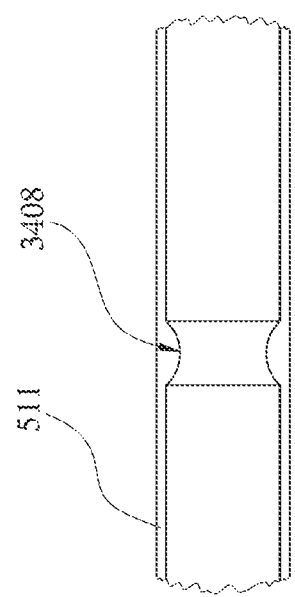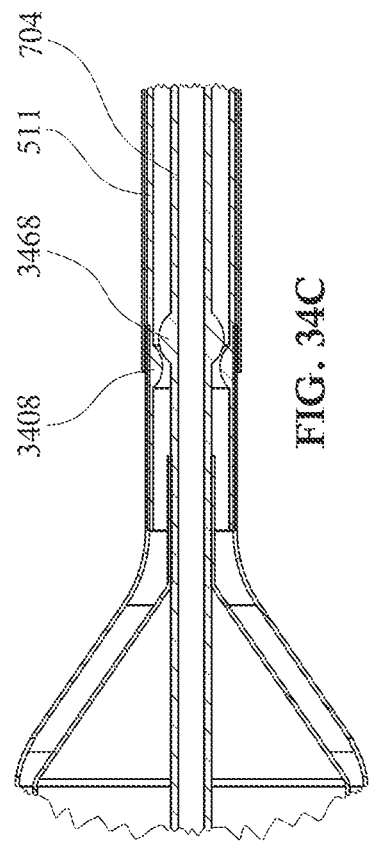

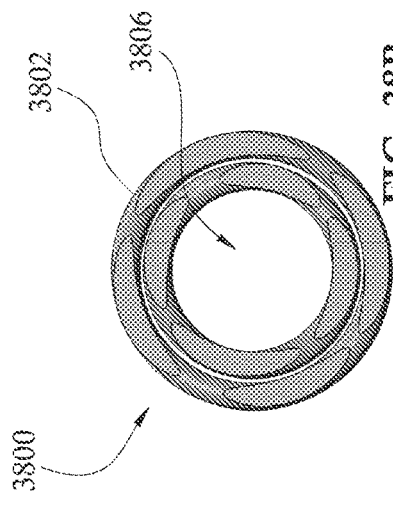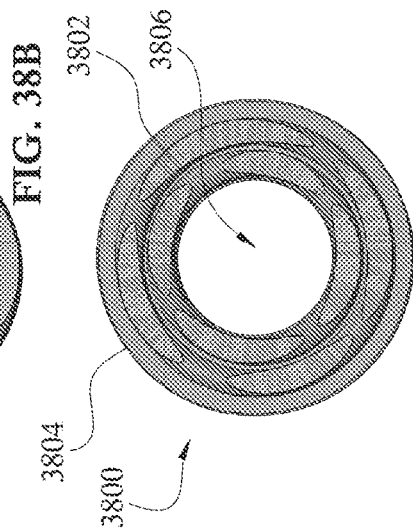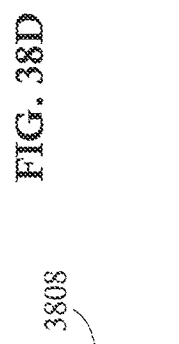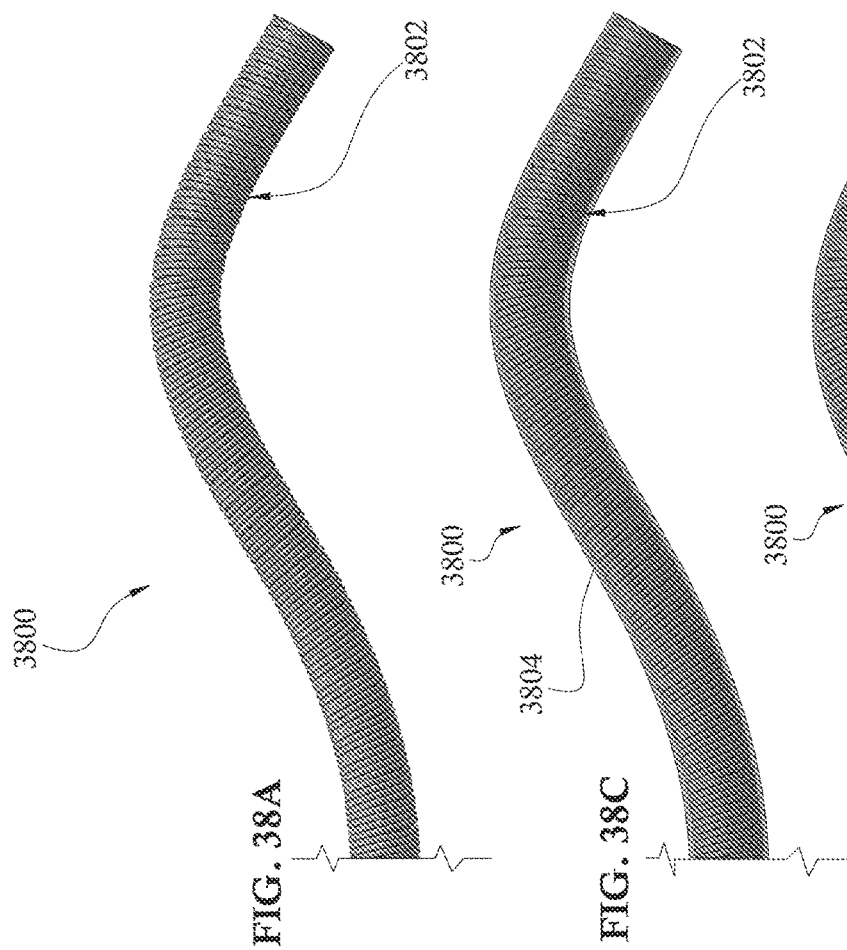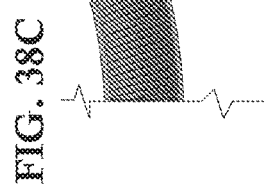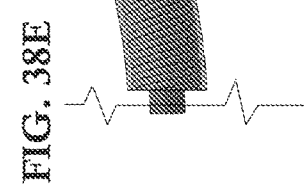

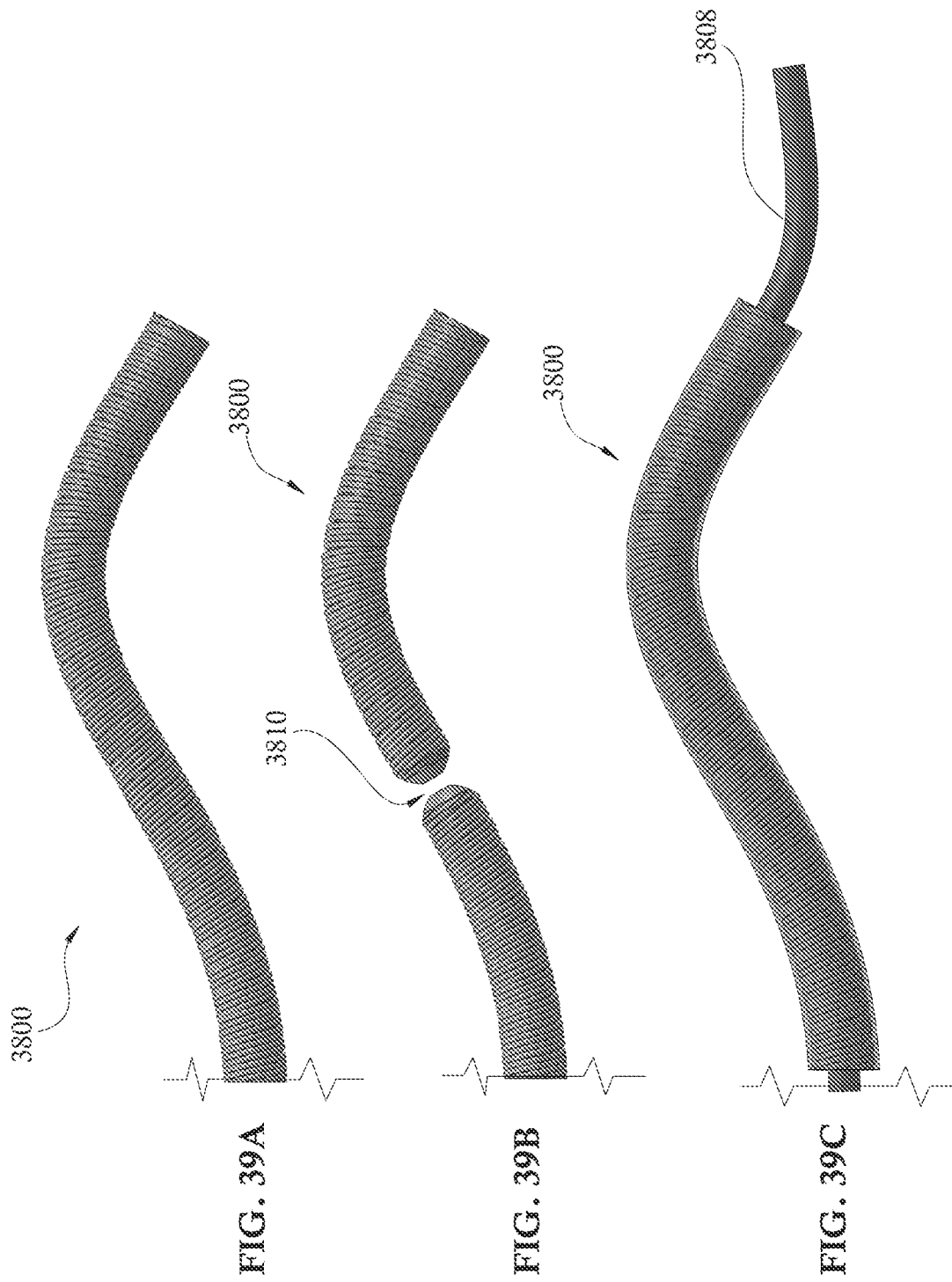

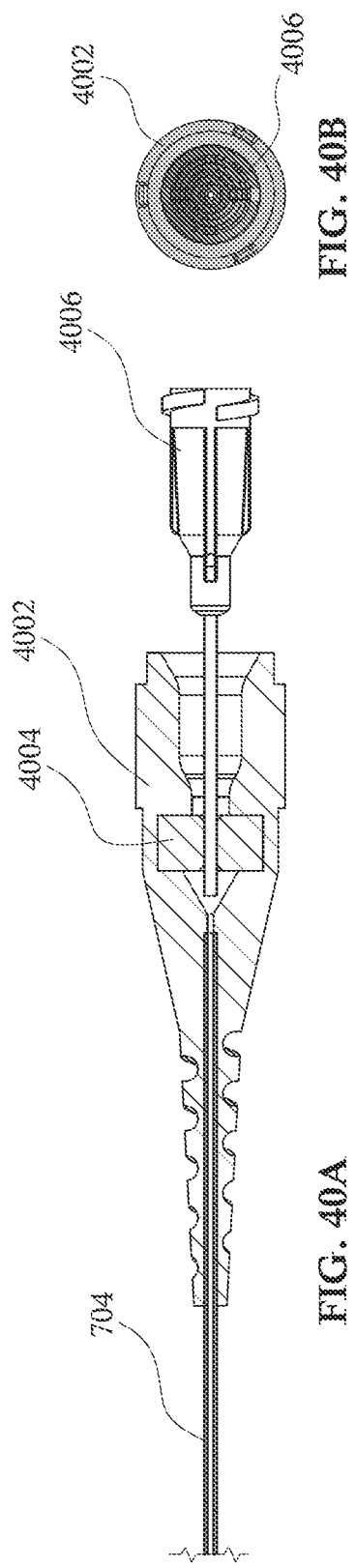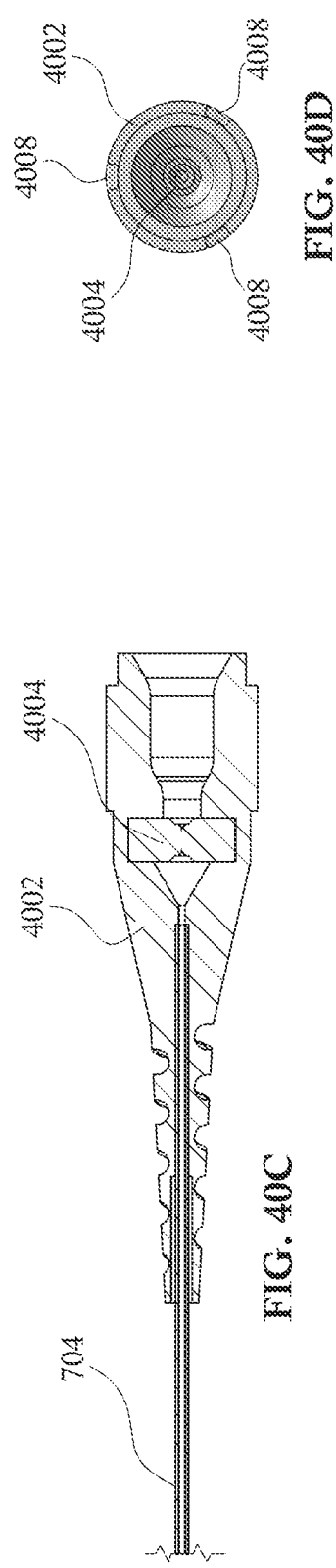

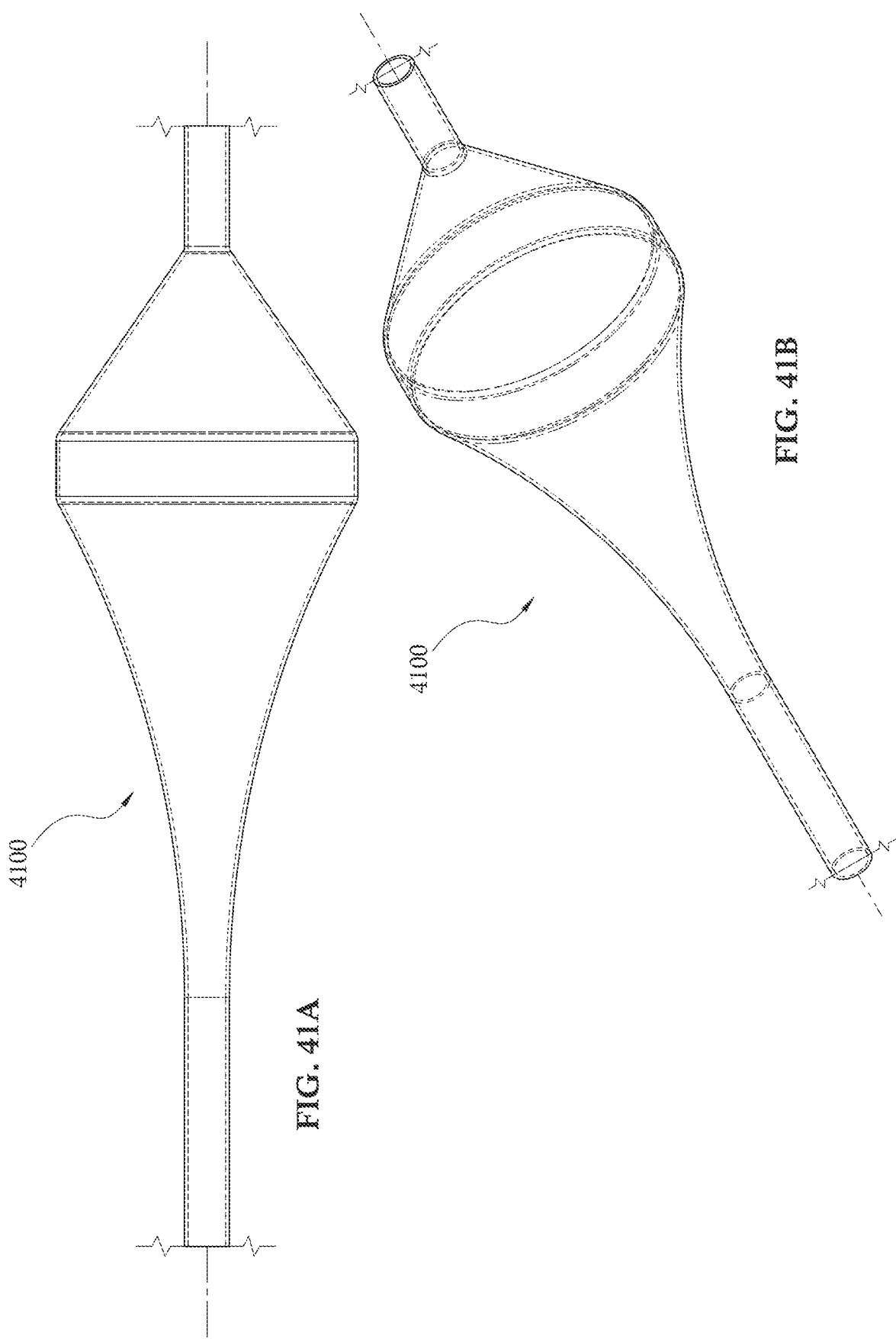

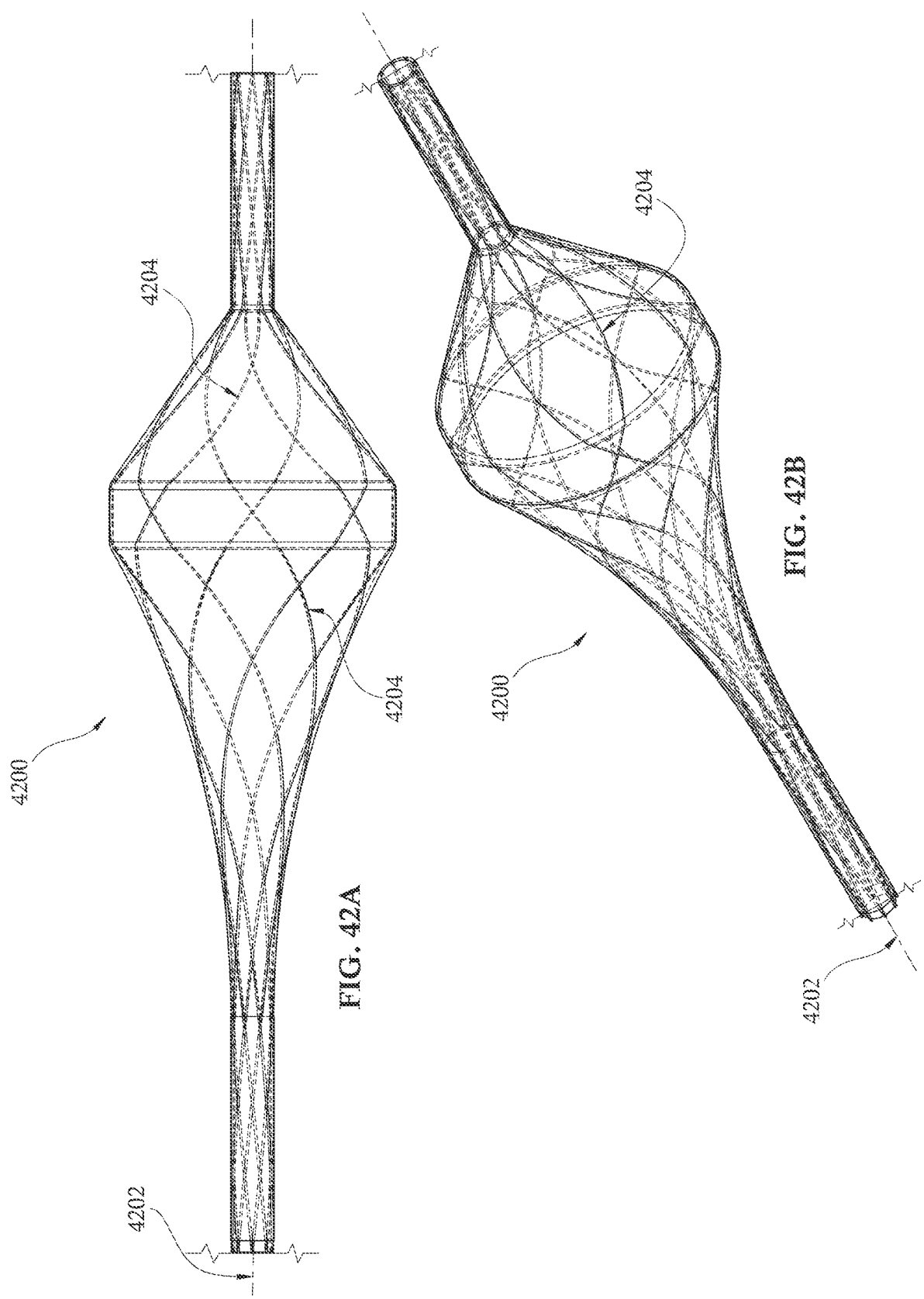

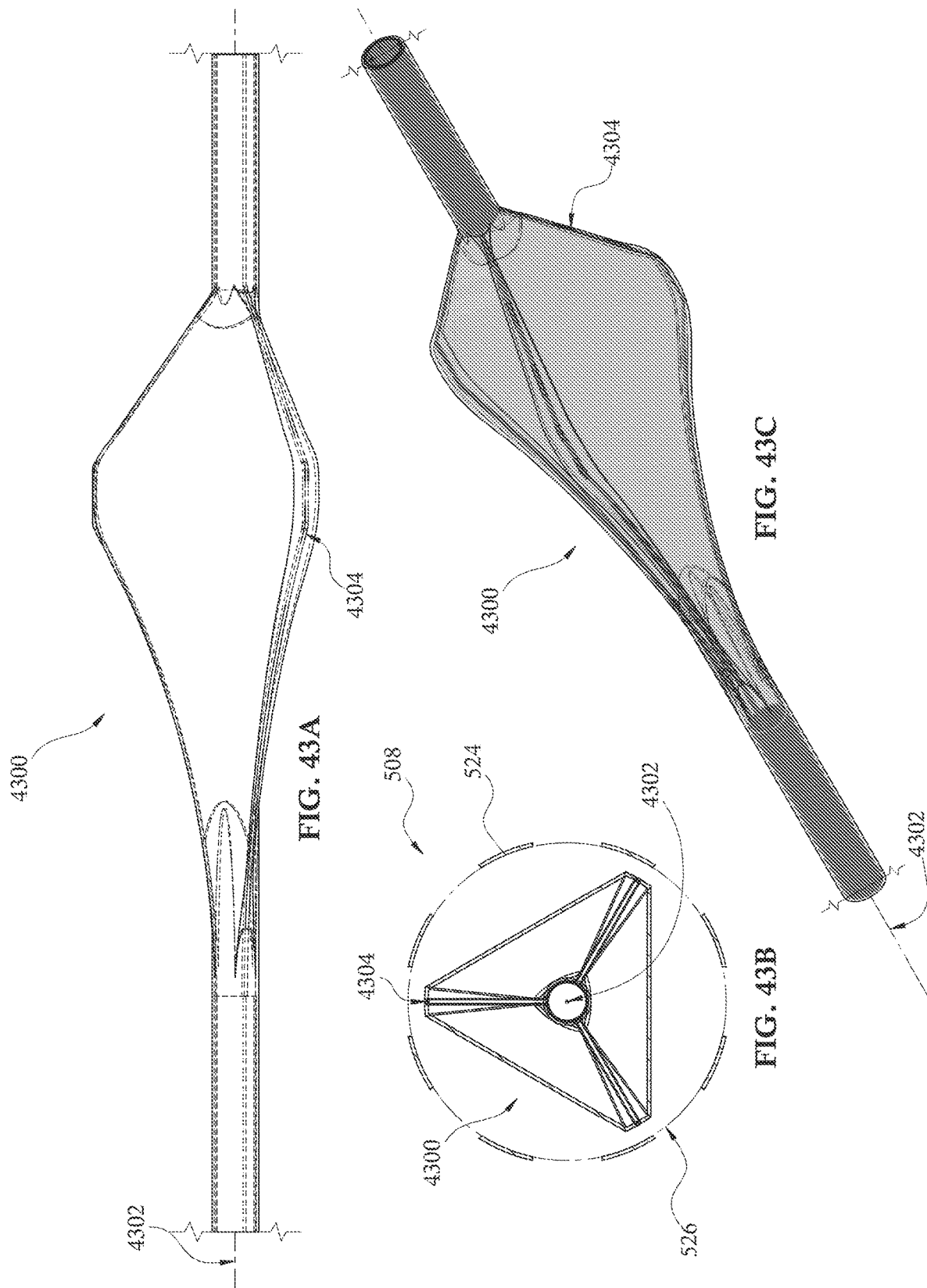

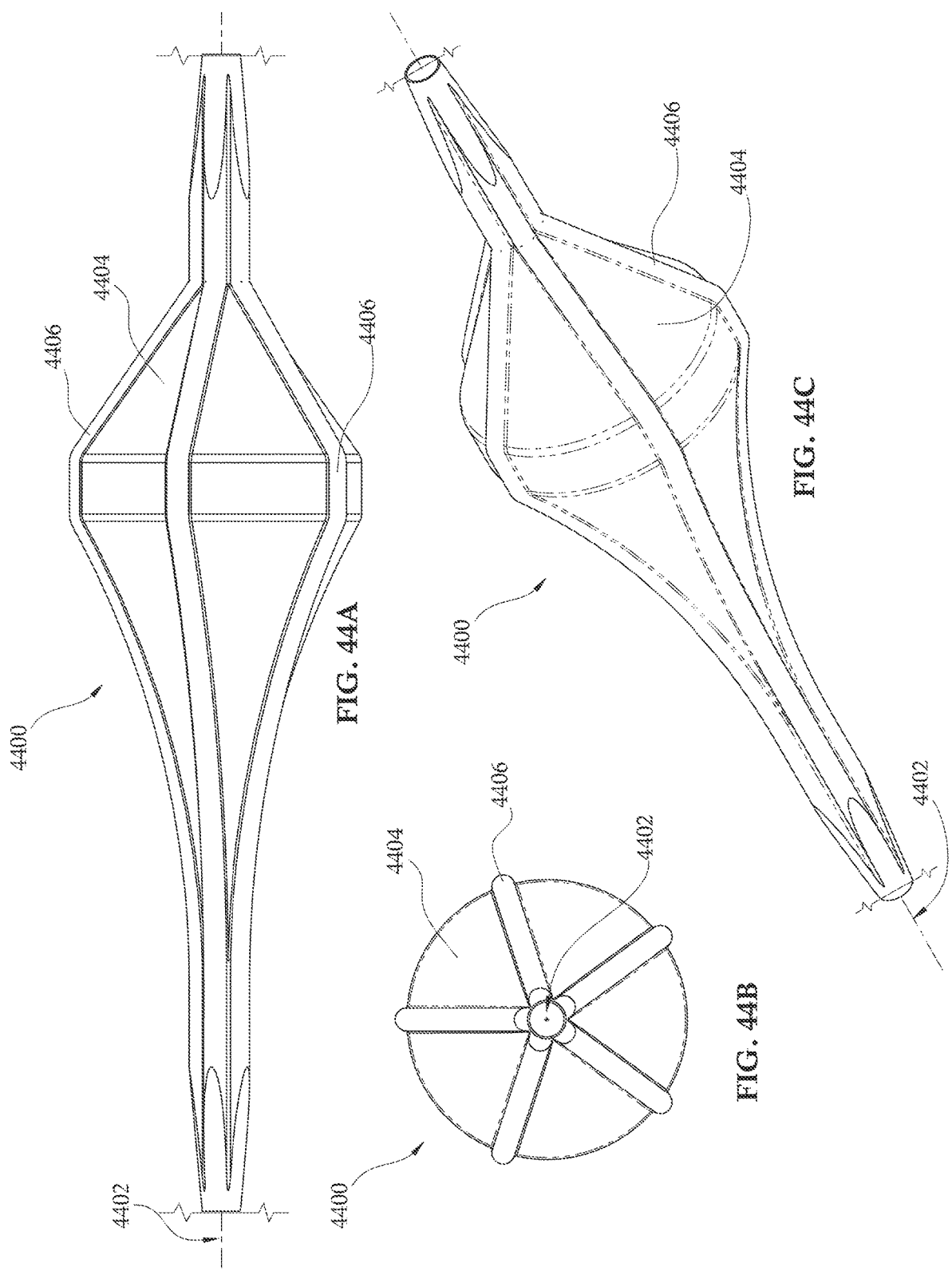

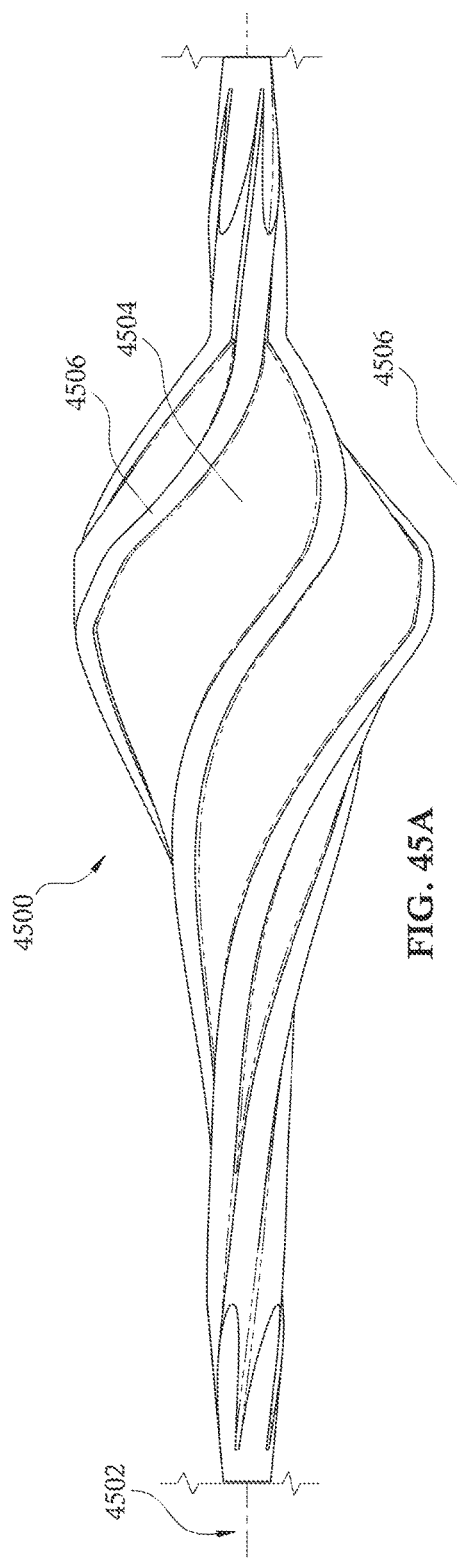
FIG. 45A
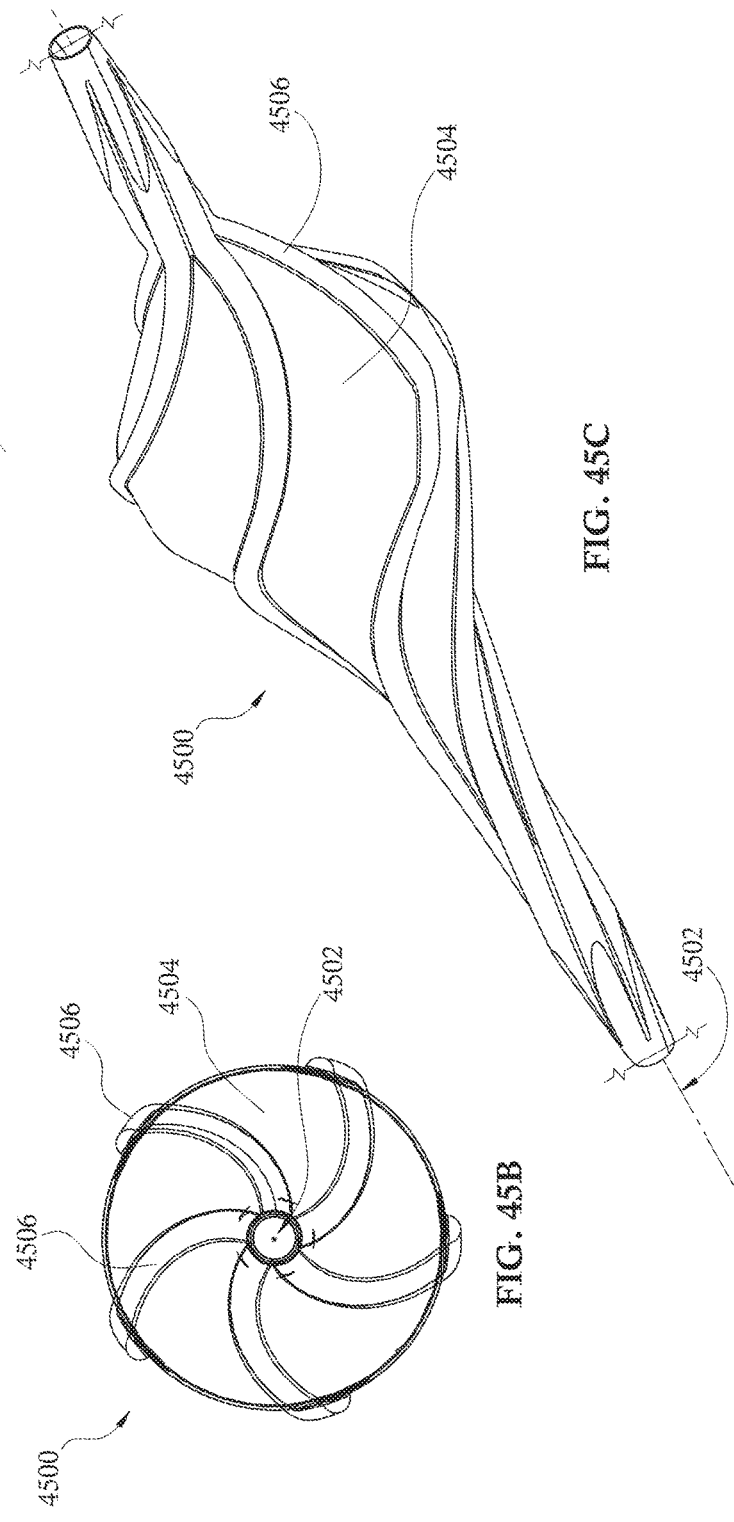
FIG. 45C
FIG. 45B

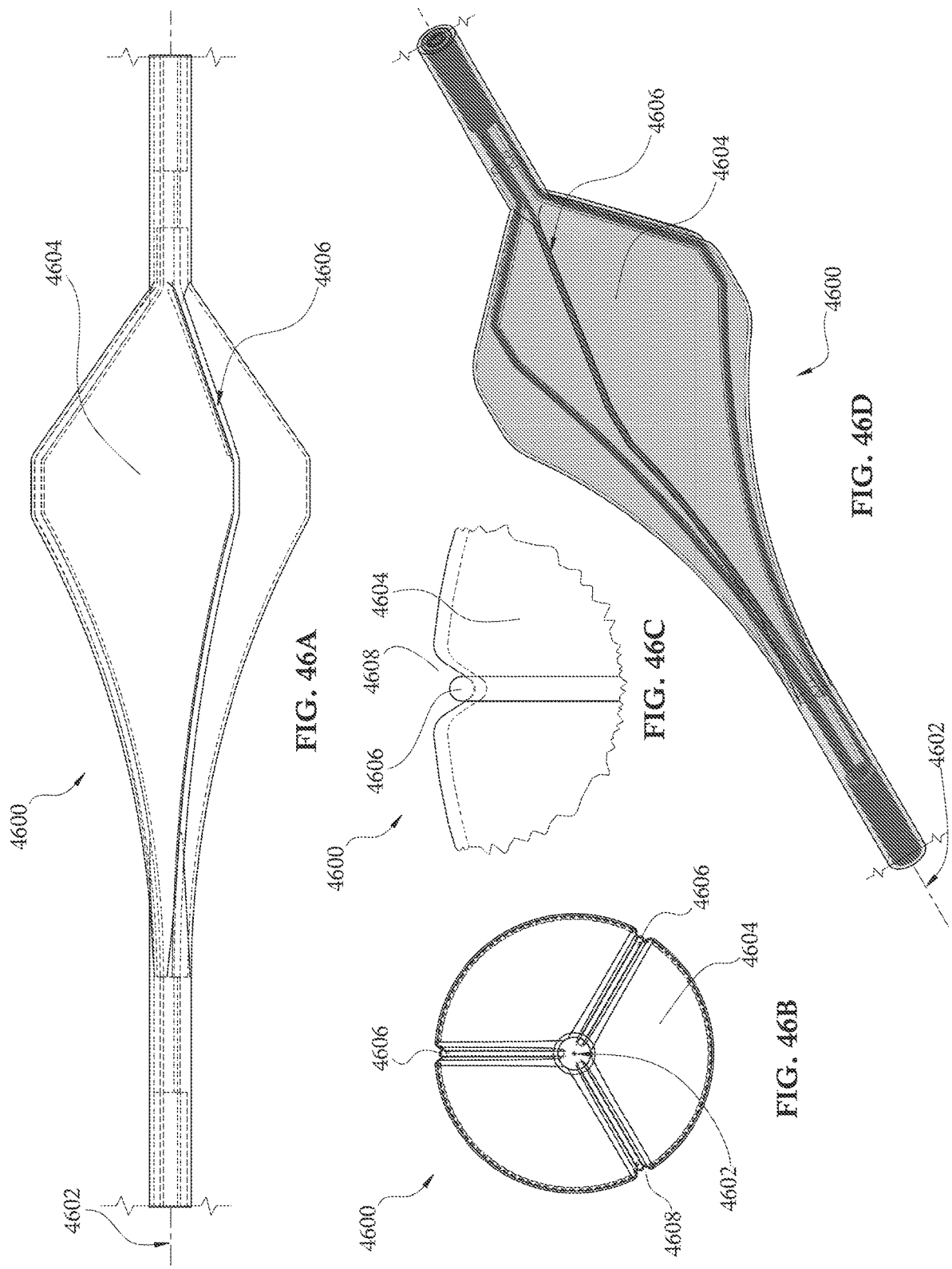

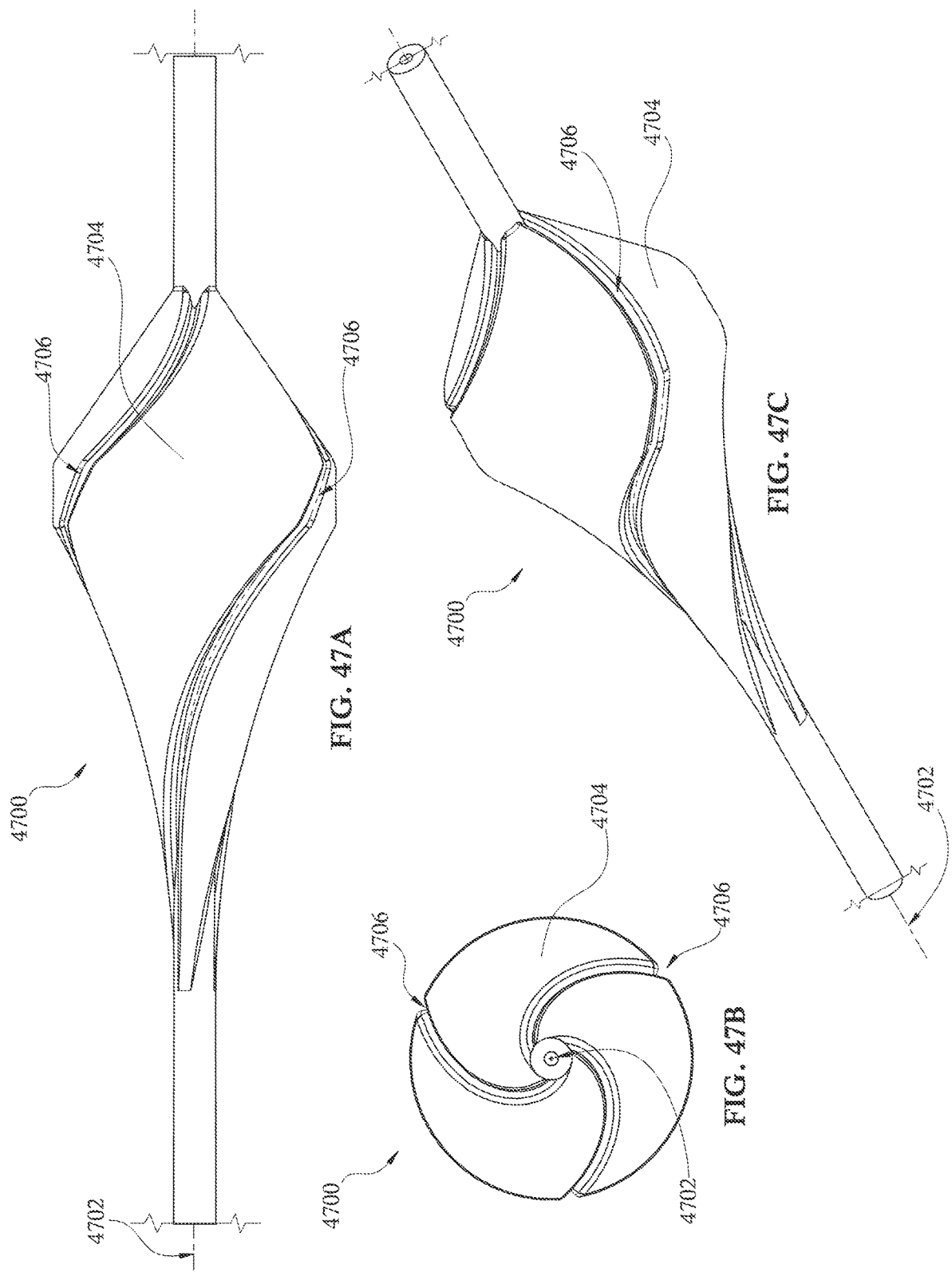

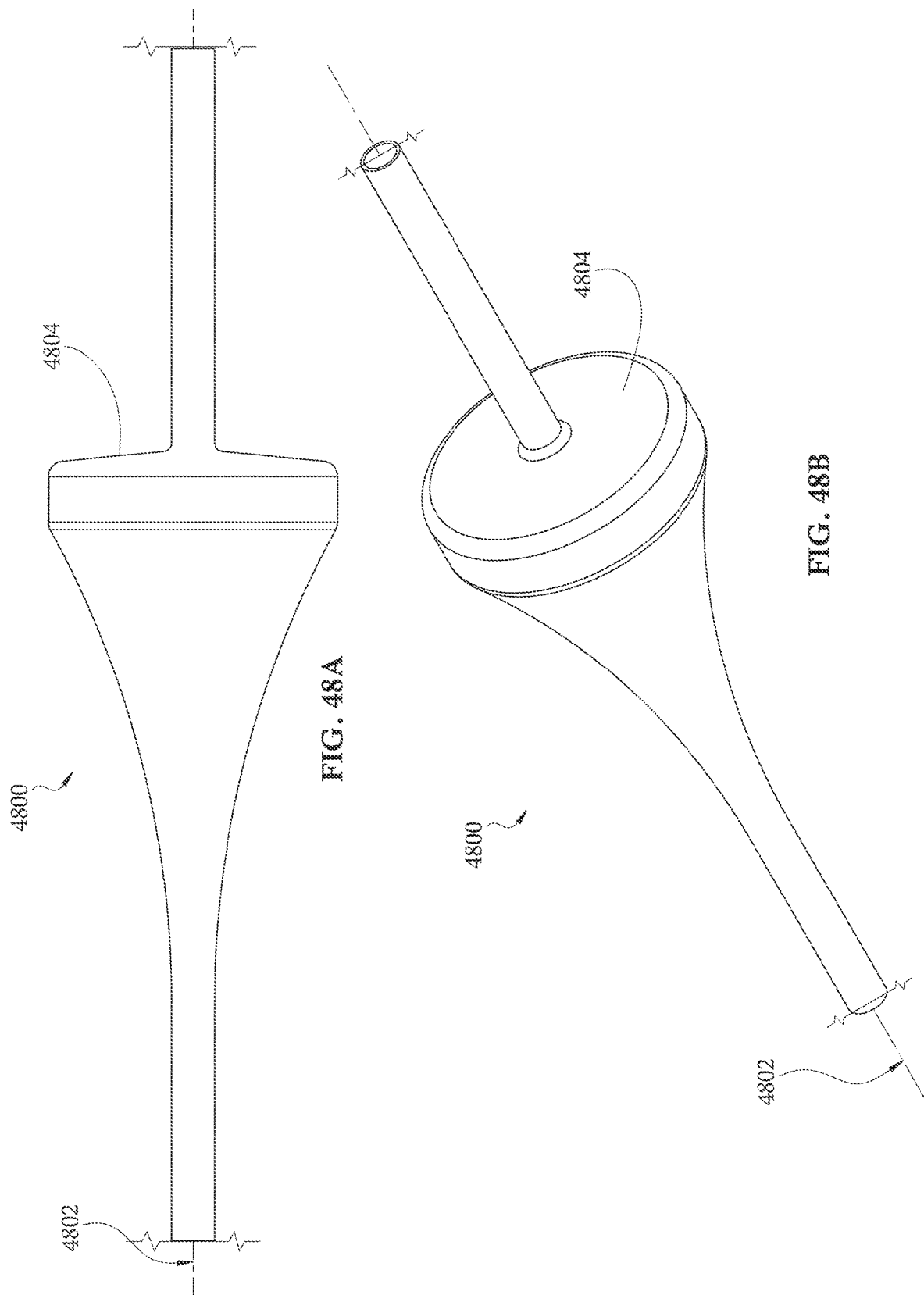

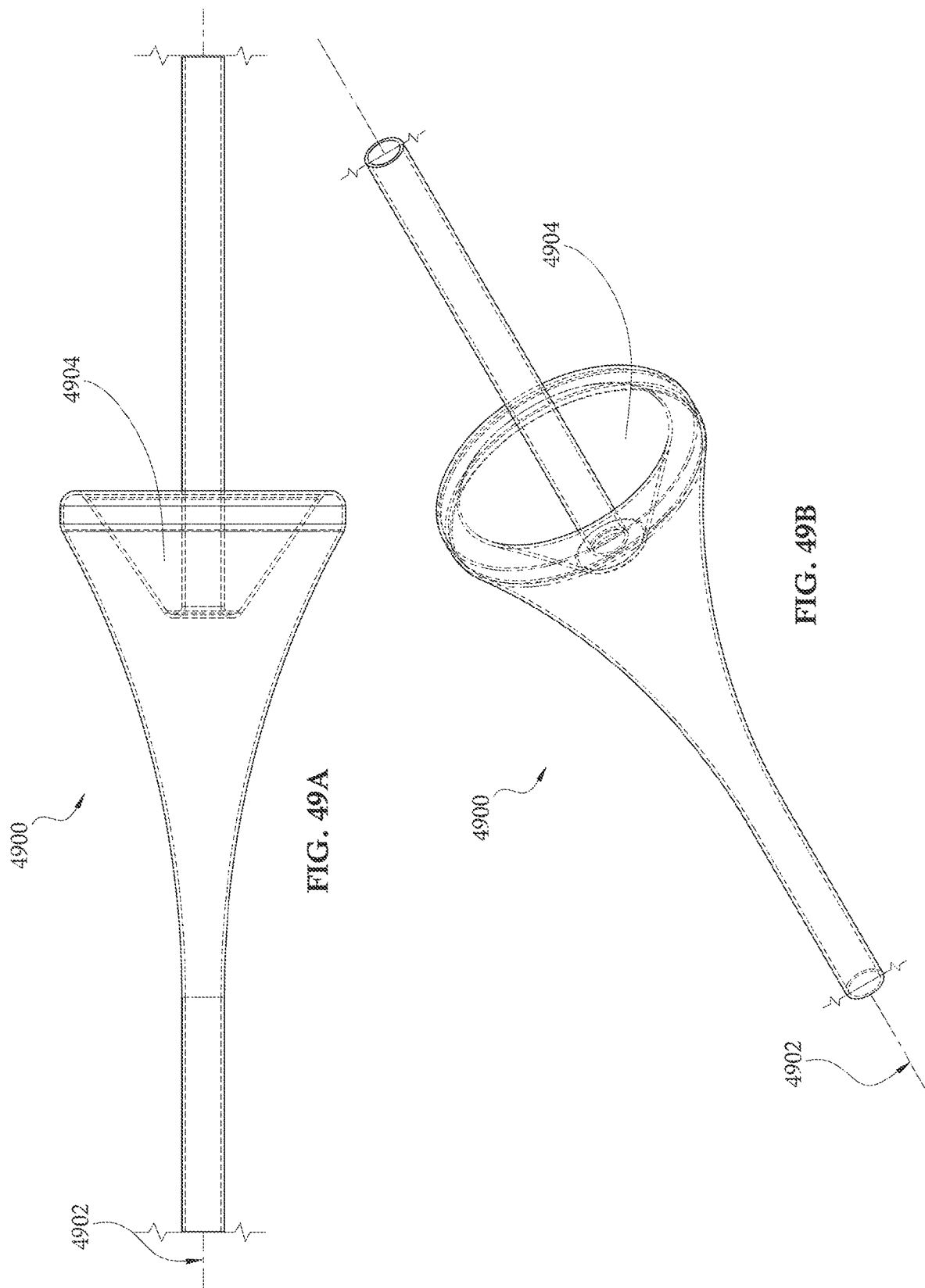

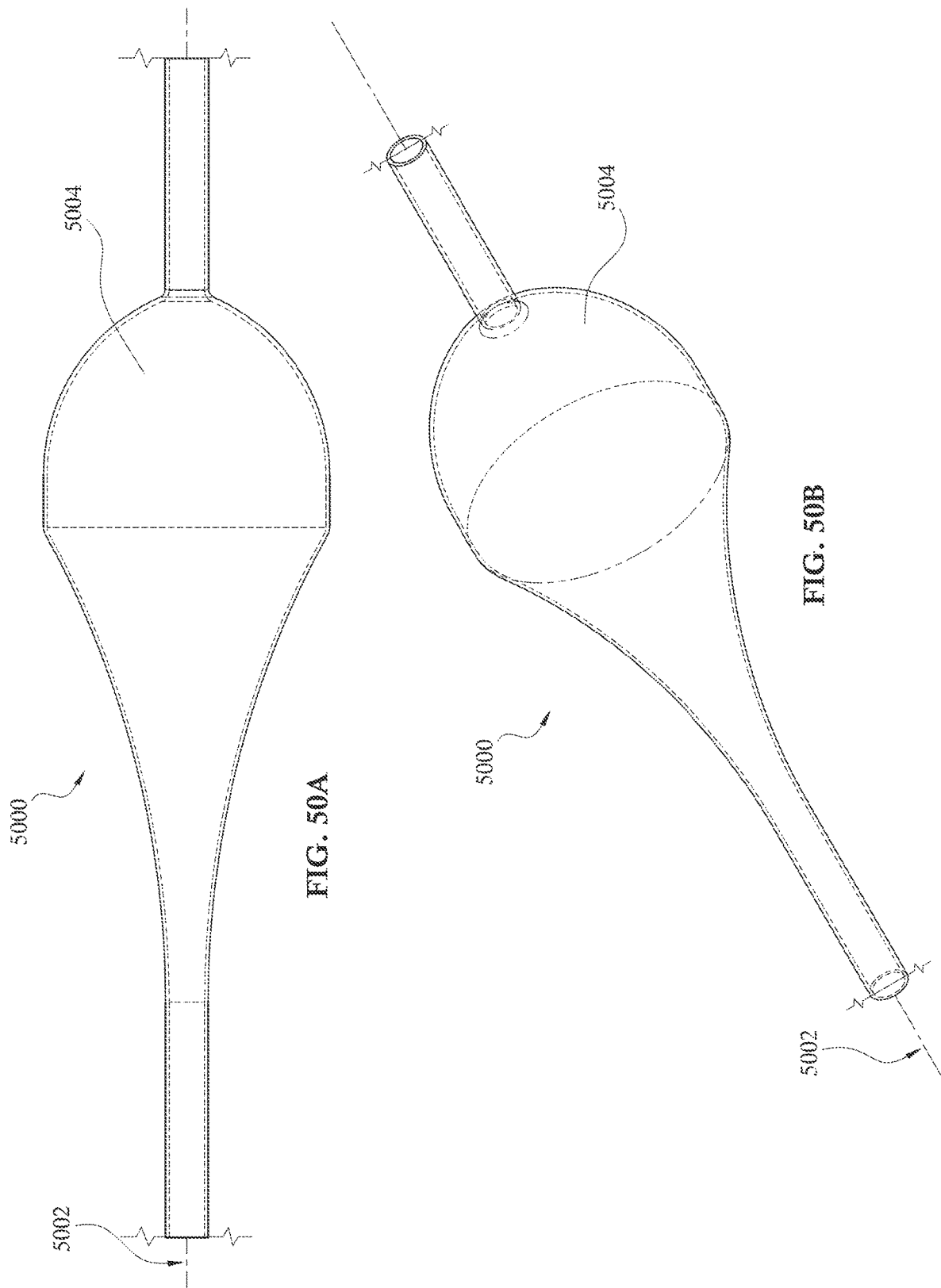

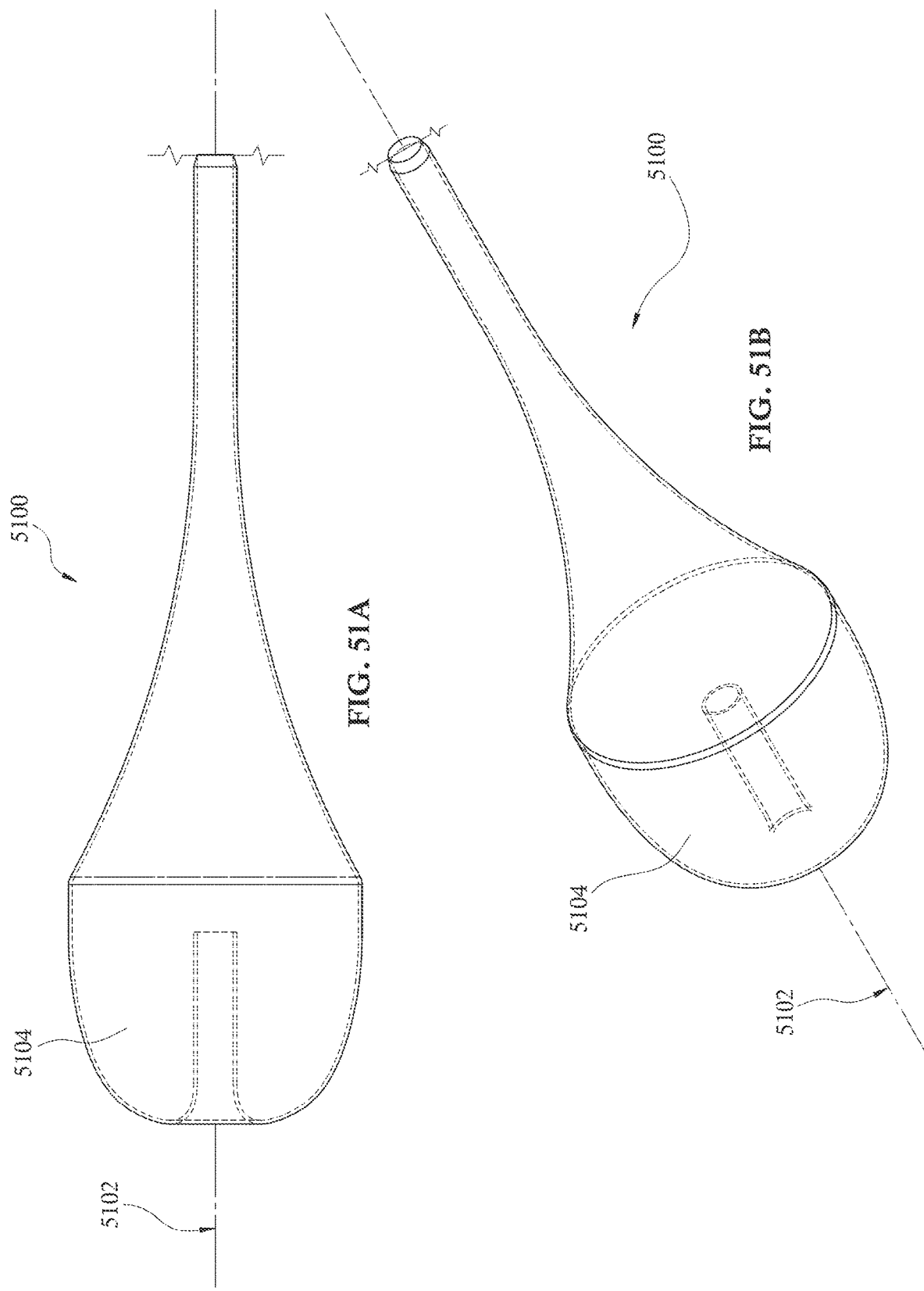

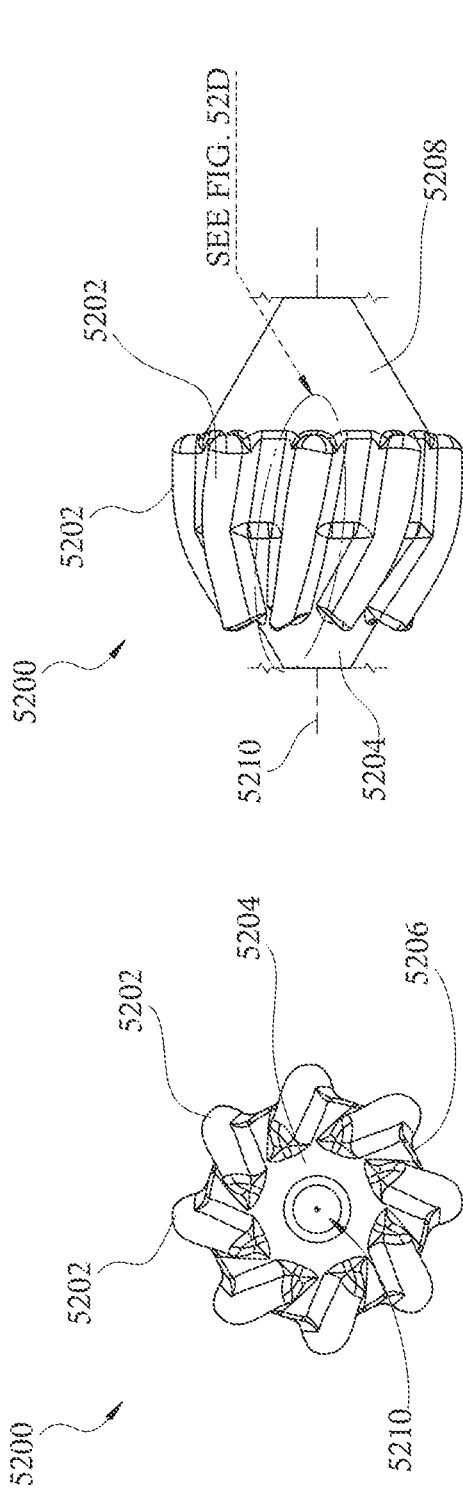
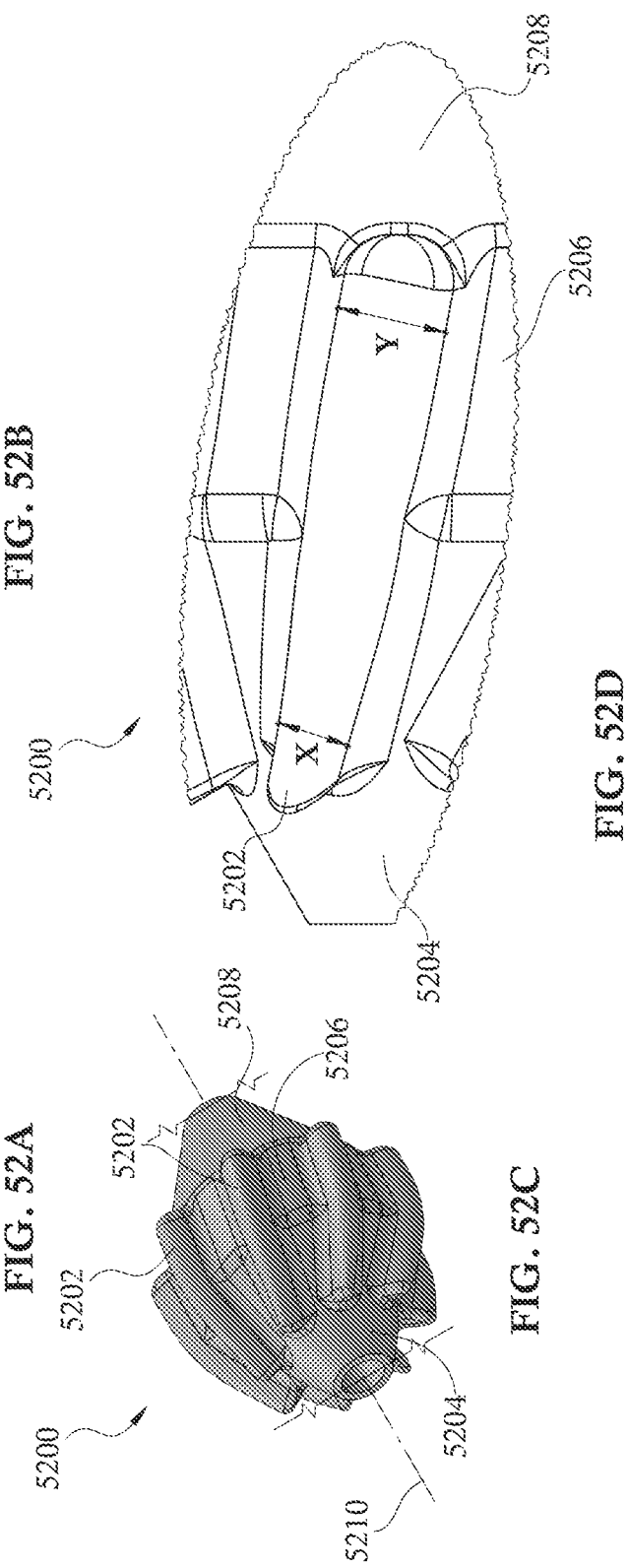
FIG. 52A
FIG. 52B
FIG. 52C
FIG. 52D

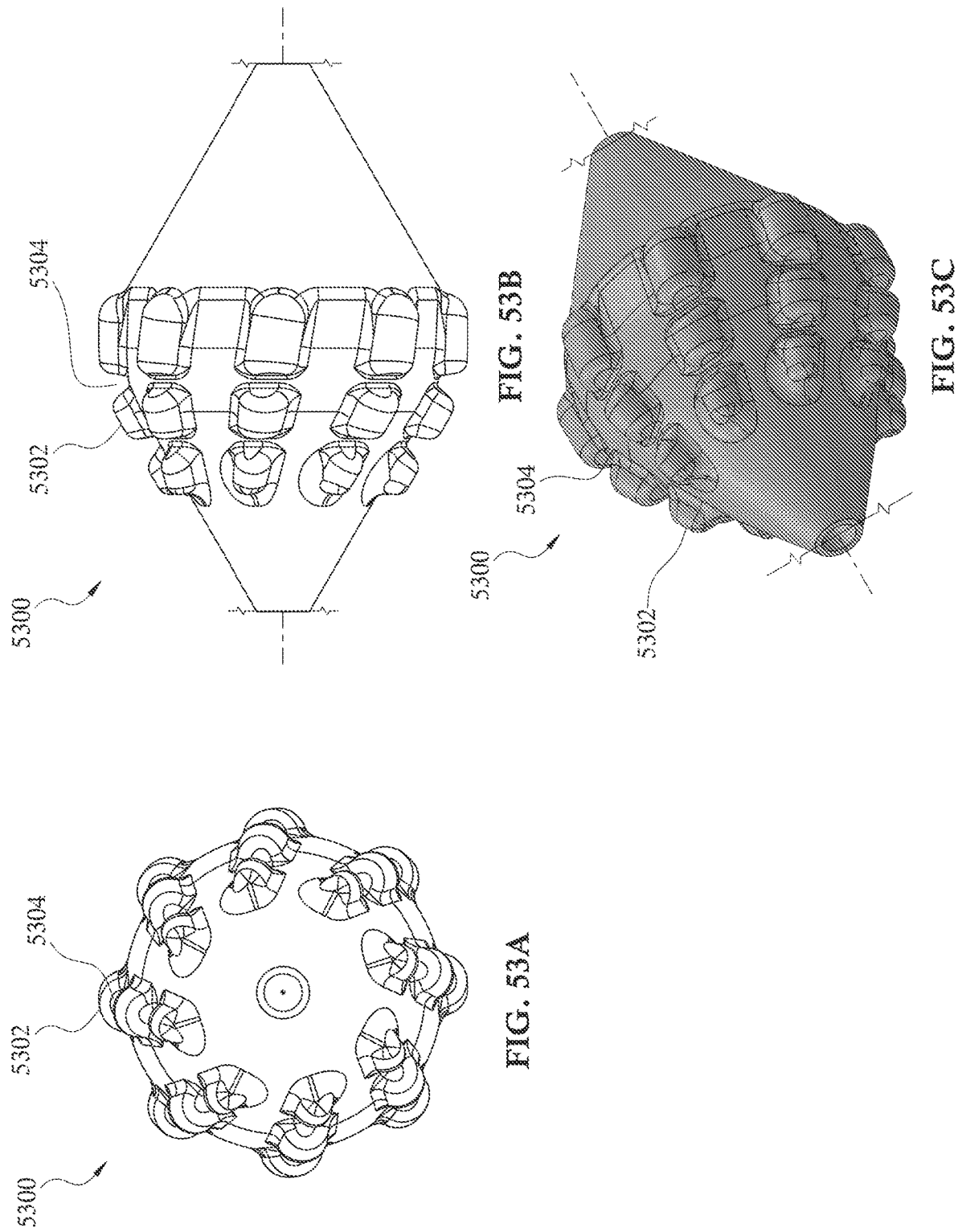

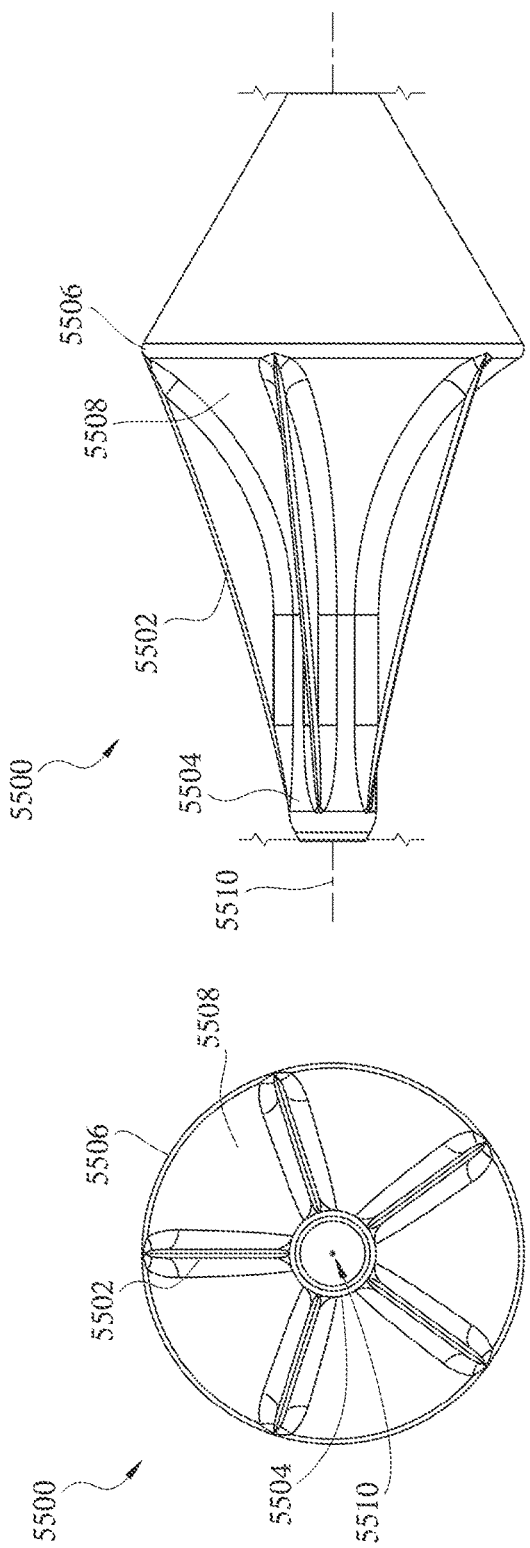
FIG. 55B
FIG. 55A
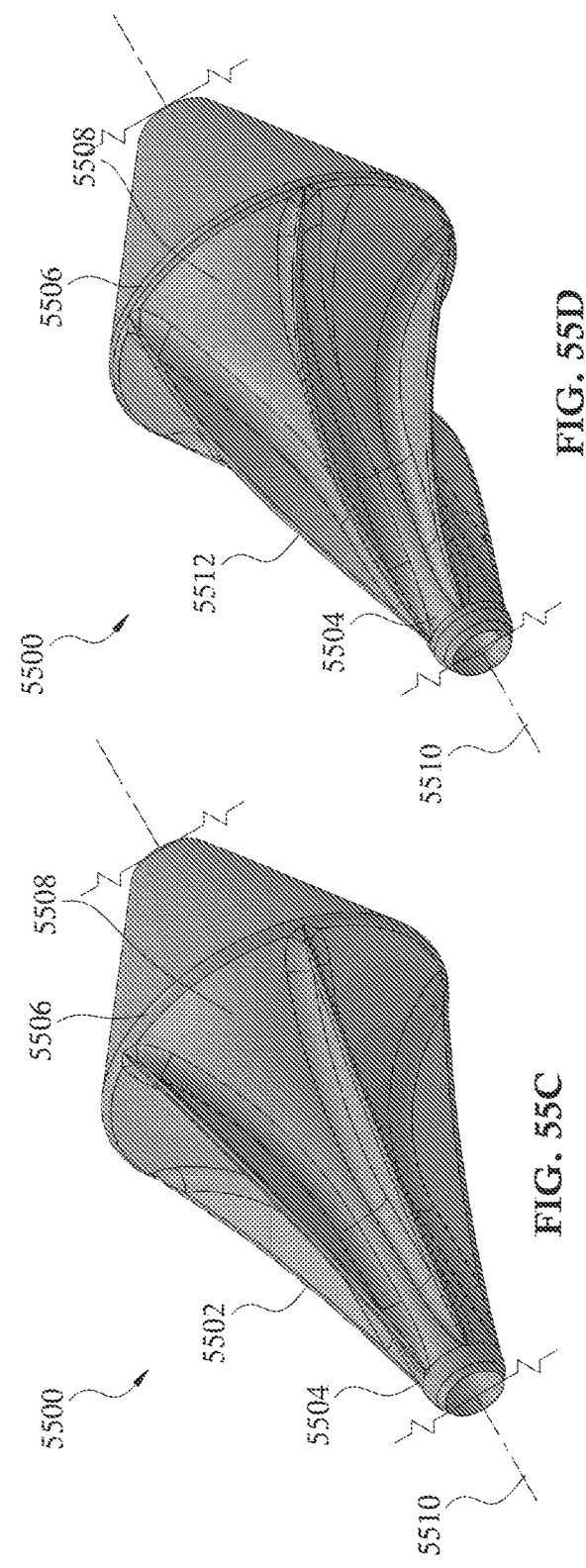
FIG. 55D
FIG. 55C

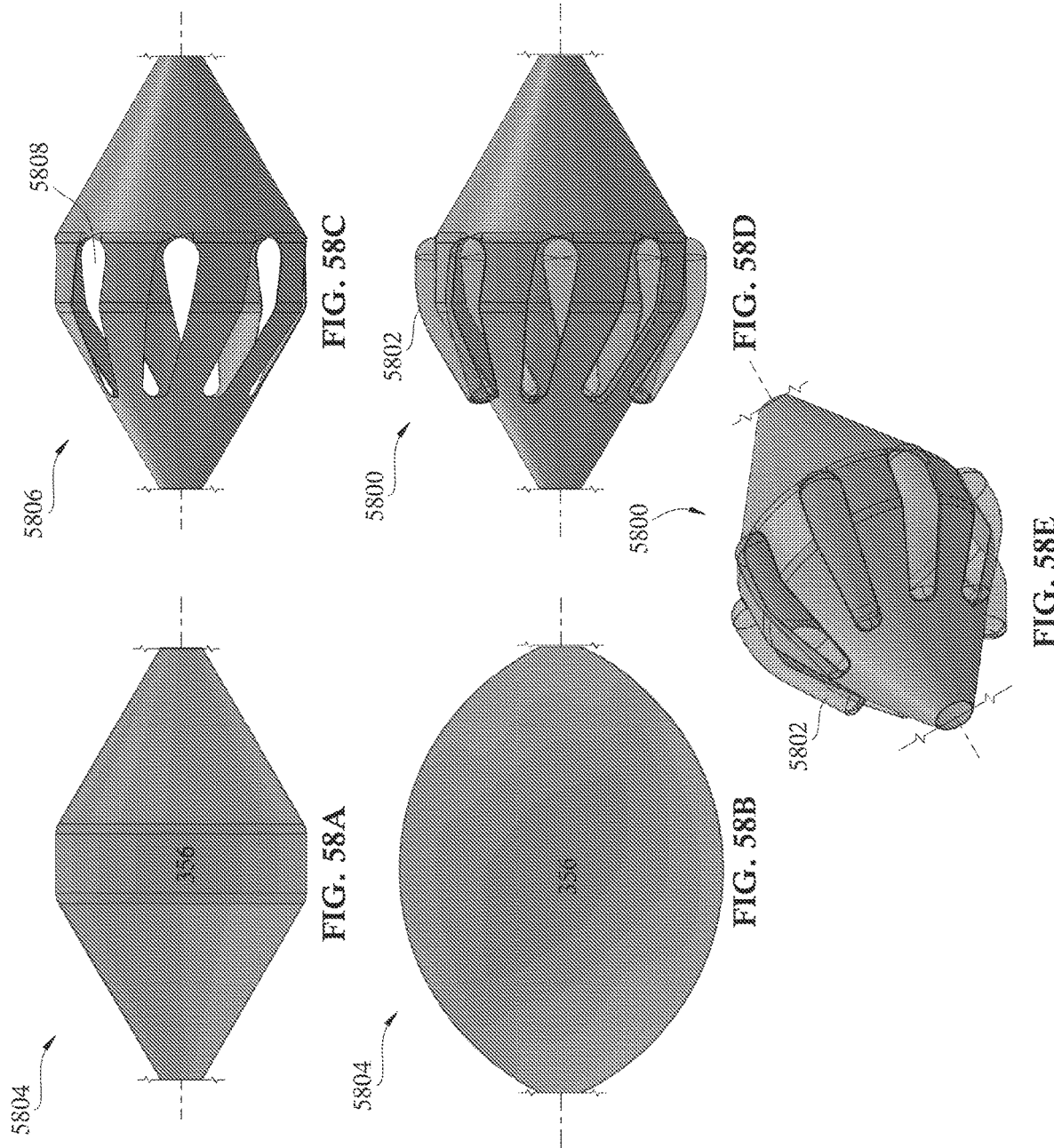

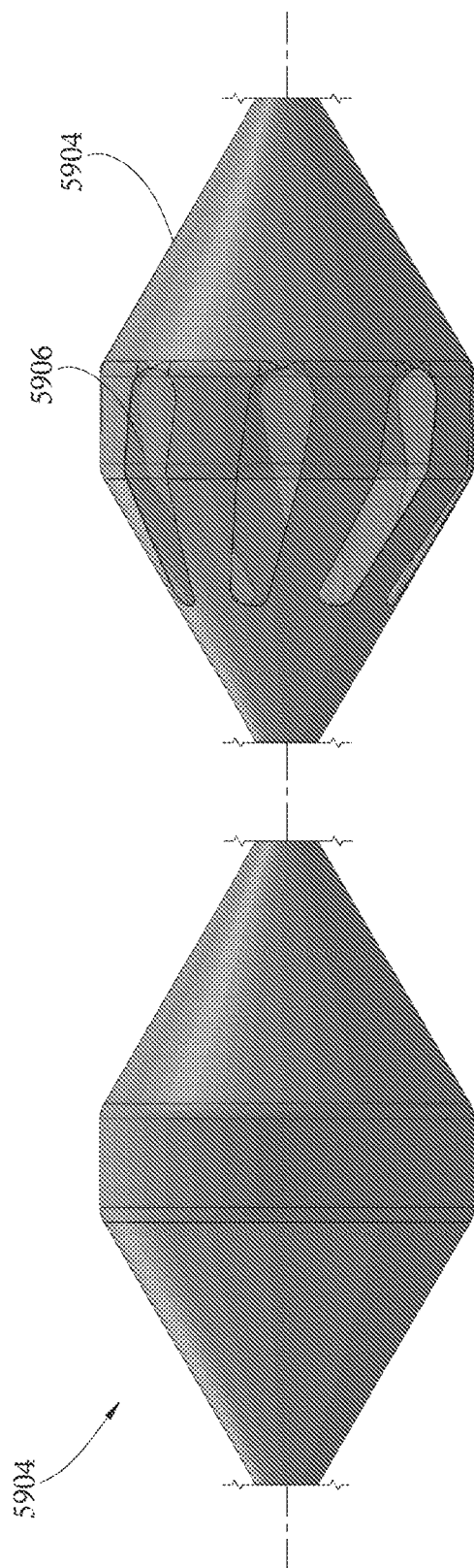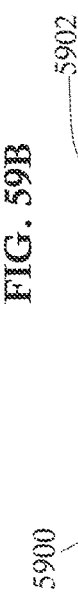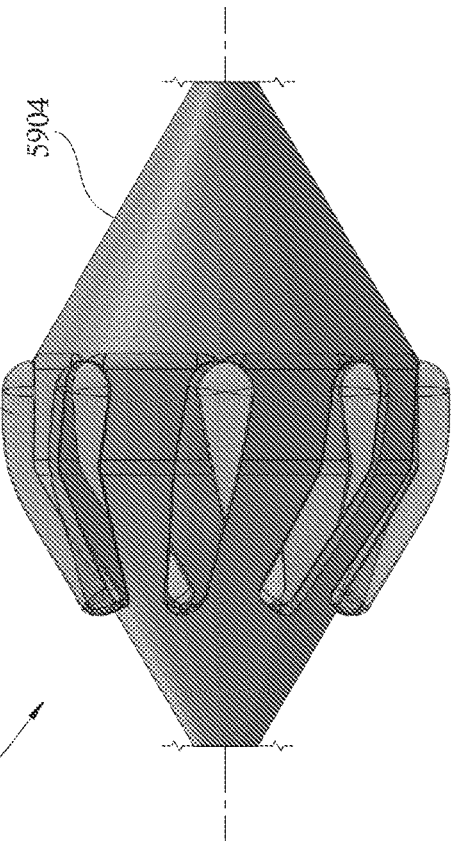
FIG. 59A
FIG. 59B
FIG. 59C

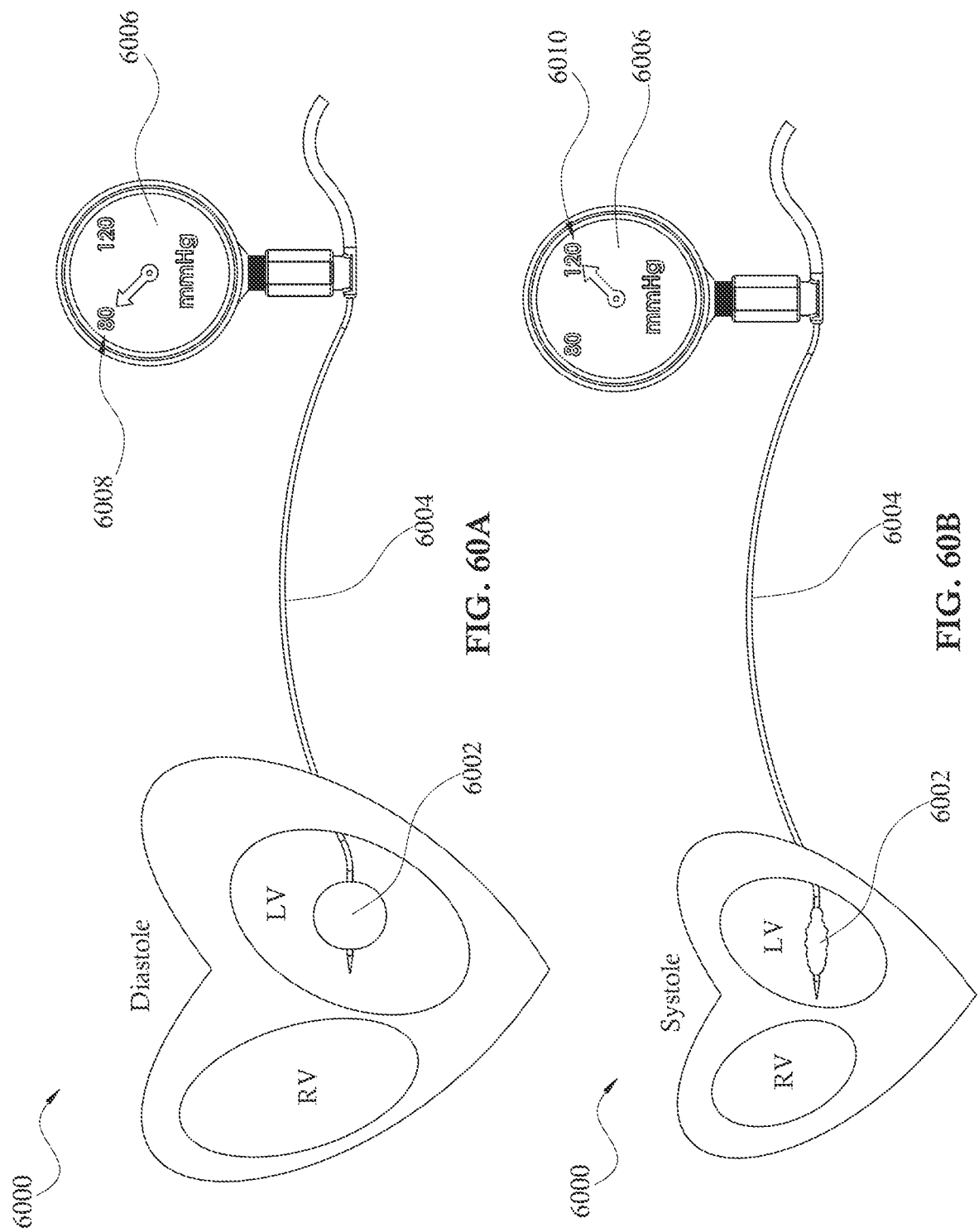

EXPANDABLE MECHANICAL HEMODYNAMIC SUPPORT SYSTEMS, DEVICES, AND METHODS

CROSS REFERENCE TO RELATED APPLICATIONS

This application claims priority to U.S. Provisional Application No. 63/309,829 filed Feb. 14, 2022, and U.S. Provisional Application No. 63/414,581 filed Oct. 10, 2022. Both prior applications are incorporated herein by reference in their entireties.

TECHNICAL FIELD

The present disclosure relates to mechanical hemodynamic support systems, devices, and methods, such as expandable percutaneous ventricular assist devices and usage methods.

BACKGROUND

Mechanical hemodynamic support devices, such as percutaneous ventricular assist devices ("pVADs") and other devices, are currently used in interventional cardiology to perform protected percutaneous coronary intervention ("PCI"). During such procedures, mechanical hemodynamic support is either placed prophylactically or readily available in the event of a complication. If a complication occurs, having hemodynamic support to continue circulating blood throughout the body while the complication is mitigated provides significant patient benefits.

Additionally, pVADs can be used to offload the heart prior to performing PCI. As a result, the work required by the heart to pump blood is reduced because the pVAD takes on a significant portion of the pumping load. There is clinical evidence showing that offloading the heart during a myocardial infarction has long-term beneficial effects for myocardial tissue viability.

Current pVADs require a relatively large access site to accommodate delivery. These devices are too large to be placed through a radial access site. These large access site requirements require vascular access via large vessels such as the femoral artery, the axillary artery, or in the venous system. Large access sites require longer patient follow-up and are more prone to bleeding complications than a radial access site.

Moreover, large access sites require some form of access site closure device or surgical cut down and suturing post-procedurally while smaller access sites can be managed with pressure alone.

Additionally, the sizes of current pVADs are too large for many patients throughout the world including children and people with smaller body structures. Accordingly, improved systems, devices, and methods would be beneficial.

SUMMARY

This disclosure describes blood pump systems such as percutaneous ventricular assist devices, and methods for their deployment and use. One example of such a system described herein includes an elongate flexible drive shaft defining a lumen, a pump impeller attached to a distal end portion of the drive shaft, and a pump housing. The pump impeller is expandable in response to receiving an inflation fluid supplied to the impeller via the lumen of the drive shaft. The system is configured to pump blood when: (i) the pump impeller is positioned in the pump housing, (ii) the pump impeller is expanded, and (iii) the drive shaft is rotated.

Such a blood pump system may optionally include one or more of at least the following features. The pump impeller may comprise a tapered body with an outer surface, and one or more of ridges extending from the outer surface. The one or more ridges may be expandable in response to receiving the inflation fluid supplied to the impeller via the lumen. The pump impeller may comprise a tapered body with an outer surface that defines one or more grooves extending along the outer surface. The pump impeller may comprise a tapered body with an outer surface and one or more non-expandable fins extending from the outer surface. The pump housing may be reconfigurable between a low-profile delivery configuration and a radially expanded configuration. The pump housing may define one or more outlet openings. The pump housing may define on or more relief cutouts around a periphery of each of the one or more outlet openings. The blood pump system may also comprise an inlet cannula extending from the pump housing. The inlet cannula may define one or more inlet openings. In some embodiments, the inlet cannula is reconfigurable between a low-profile delivery configuration and a radially expanded configuration. The blood pump system may also comprise a drive shaft housing extending proximally from the pump housing and defining a housing lumen configured to slidably receive the drive shaft and the pump impeller when the pump impeller is deflated.

Another example system described herein is a catheter-based blood pump. One example of such a system described herein includes a rotatable pump impeller attached to a flexible drive shaft. The pump impeller is reconfigurable between: (i) a deflated low-profile delivery arrangement configured for trans-vascular advancement to a target location within a patient and (ii) an inflated radially expanded arrangement. The pump impeller is configured to pump blood when rotated via the drive shaft in the inflated radially expanded arrangement.

Such a catheter-based blood pump may optionally include one of more of at least the following features. The pump impeller may comprise a tapered body with an outer surface, and one or more ridges extending from the outer surface, wherein the plurality of ridges are inflatable. The pump impeller may comprise a tapered body with an outer surface, and one or more non-expandable fins or ridges extending from the outer surface. The pump impeller may comprise a tapered body with an outer surface that defines one or more grooves extending along the outer surface. The catheter-based blood pump may also include a housing component. Such a housing component may include an elongate drive shaft housing defining a housing lumen, a pump housing disposed at a distal end portion of the drive shaft housing, and an inlet cannula extending from the pump housing. In some embodiments, the pump housing and the inlet cannula are radially reconfigurable between: (i) low-profile configurations when radially constrained in a sheath lumen of a delivery sheath device and (ii) radially expanded configurations when unconstrained by the delivery sheath device. The housing lumen may be configured to slidably receive the drive shaft and the pump impeller when the pump impeller is in the deflated low-profile delivery arrangement.

Another example system described herein includes a blood pump comprising a rotatable pump impeller. The rotatable pump impeller is inflatable from a low-profile delivery arrangement to a radially expanded arrangement. The pump impeller is configured to pump blood when rotated when in the radially expanded arrangement.

Such a blood pump may optionally include one or more of at least the following features. The pump impeller may comprise a tapered body with an outer surface, and one or more ridges extending from the outer surface. The one or more ridges may be inflatable. The pump impeller may comprise a tapered body with an outer surface that defines one or more grooves extending along the outer surface. The blood pump may also include an elongate flexible drive shaft. The pump impeller may be attached to a distal end portion of the drive shaft. The pump impeller may rotate in response to rotation of the drive shaft.

Another example system described herein includes a blood pump system that includes an elongate delivery sheath device defining a sheath lumen, a housing component slidably disposable in the sheath lumen, and a rotatable inner catheter. The housing component includes an elongate drive shaft housing defining a housing lumen, a pump housing disposed at a distal end portion of the drive shaft housing, and an inlet cannula extending from the pump housing. The pump housing and the inlet cannula are radially reconfigurable between: (i) low-profile configurations when radially constrained in the sheath lumen and (ii) radially expanded configurations when unconstrained by the delivery sheath device. The rotatable inner catheter is slidably disposable in the housing lumen. The rotatable inner catheter includes an elongate flexible drive shaft, and an impeller disposed at a distal end of the drive shaft. The impeller is slidably disposable within the housing lumen when in a radially collapsed configuration. The impeller is radially expandable to an operable configuration within the pump housing.

Such a blood pump system may optionally include one or more of at least the following features. The impeller may be movable relative to the pump housing in response to retraction or advancement of the drive shaft relative to the drive shaft housing. The drive shaft may define an inflation lumen. The impeller may be radially expandable in response to receiving an inflation fluid supplied to the impeller via the inflation lumen. The inner catheter may also include a drive shaft hub attached to a proximal end portion of the drive shaft. The drive shaft hub may have a drive shaft hub seal coupled with the hub. The drive shaft hub seal may seal a proximal end of the inflation lumen. The blood pump system may also include a motor. The inner catheter may also include a drive shaft hub attached to a proximal end portion of the drive shaft. The drive shaft hub may be configured to be coupled to the motor. The motor and the drive shaft hub may be configured to allow an inflation fluid to pass into the inflation lumen via the drive shaft hub while the drive shaft hub is coupled to the motor. The blood pump system may be configured to pump blood when: (i) the impeller is positioned in the pump housing at a target location within a patient, (ii) the impeller and the pump housing are expanded, and (iii) the drive shaft is rotated by a motor located external to the patient. The inlet cannula may define one or more inlet openings. The pump housing may define one or more outlet openings. The delivery sheath device and the drive shaft housing may each define one or more openings. The one or more openings of the delivery sheath device may at least partially align with the one or more openings of the drive shaft housing when the impeller is positioned in the pump housing. The blood pump system may be configured to pump blood by rotation of the impeller while the impeller is positioned in the pump housing and without any mechanical bearing or bushing between the impeller and the pump housing. The impeller may be configured to self-center relative to the pump housing when rotating within the pump housing.

Another example system described herein includes a percutaneous ventricular assist device. Such a percutaneous ventricular assist device may include an elongate drive shaft housing defining a lumen, a pump housing attached to a distal end portion of the drive shaft housing, and a pump impeller attached to a distal end portion of an elongate drive shaft. The pump housing may be attached to a distal end portion of the drive shaft housing. The pump housing may be radially reconfigurable between: (i) a low-profile configuration configured for trans-vascular advancement to a target location within a patient and (ii) a radially expanded configuration. The pump impeller may be slidably disposable within the lumen when in a radially collapsed configuration. The pump impeller may be radially expandable to an operable configuration when the pump impeller is within the radially expanded configuration of the pump housing in the target location within the patient.

Such a percutaneous ventricular assist device may optionally include one or more of at least the following features. The pump impeller may be movable relative to the pump housing in response to retraction or advancement of the drive shaft relative to the drive shaft housing. The drive shaft may define an inflation lumen. The pump impeller may be radially expandable in response to receiving an inflation fluid supplied to the pump impeller via the inflation lumen. The percutaneous ventricular assist device may be configured to pump blood by rotation of the pump impeller while the pump impeller is positioned in the pump housing and without any mechanical bearing or bushing between the pump impeller and the pump housing. The pump housing may be configured to self-expand to the radially expanded configuration.

Another example system described herein includes a mechanical hemodynamic support device. The mechanical hemodynamic support device includes a pump housing configured to be disposed in a patient and to permit blood flow from a pump housing inlet to a pump housing outlet, and a pump impeller positionable in the pump housing. The pump impeller is rotatable relative to the pump housing to cause blood flow from the pump housing inlet to the pump housing outlet. The pump impeller is configured to self-center relative to the pump housing when rotating relative to the pump housing.

Such a mechanical hemodynamic support device may optionally include one or more of at least the following features. The pump impeller may be attached to a flexible drive shaft. The pump impeller may be reconfigurable between: (i) a deflated low-profile delivery arrangement configured for trans-vascular advancement to a target location within a patient and (ii) an inflated radially expanded arrangement in which the pump impeller is configured to pump blood when rotated via the drive shaft. The pump housing may be reconfigurable between a low-profile delivery configuration and a radially expanded operable configuration. The pump impeller may be inflatable from a low-profile delivery arrangement to a radially expanded operable arrangement in which the pump impeller is configured to pump blood when rotating relative to the pump housing. The pump housing may be attached to a distal end portion of a drive shaft housing. The drive shaft housing may allow a purge fluid or blood to flow between the pump housing and the pump impeller to provide a hydrodynamic bearing between the pump housing and the pump impeller.

This disclosure also describes methods for deploying and operating blood pump systems such as percutaneous ventricular assist devices and mechanical hemodynamic support devices. In one example, such a method for deploying a percutaneous blood flow assist device to a target location within a patient includes advancing, through an incision of the patient, an elongate delivery sheath device. The delivery sheath device may define a sheath lumen that contains a housing component slidably disposed in the sheath lumen. Such a housing component may include an elongate drive shaft housing defining a housing lumen, a pump housing disposed at a distal end portion of the drive shaft housing, and an inlet cannula extending distally from the pump housing. The method may also include: retracting, when the pump housing is at the target location, the delivery sheath device relative to the housing component to express the inlet cannula and the pump housing out from the sheath lumen; inserting a rotatable inner catheter into the housing lumen of the drive shaft housing; advancing the inner catheter relative to the housing component to position the pump impeller within the pump housing; and inflating, by supplying an inflation fluid, the pump impeller to a radially expanded operable configuration while the pump impeller is within the pump housing. The pump housing and the inlet cannula may be radially reconfigurable between: (i) low-profile configurations when radially constrained in the sheath lumen and (ii) radially expanded configurations when unconstrained by the delivery sheath device. The inner catheter may comprise an elongate flexible drive shaft, and a pump impeller disposed at a distal end of the drive shaft. The pump impeller may be in a radially collapsed configuration when within the housing lumen.

Such a method for deploying a percutaneous blood flow assist device to a target location within a patient may optionally include one or more of at least the following features. The incision may provide access to a femoral artery of the patient, and the delivery sheath device may be advanced to the target location via the femoral artery. The incision may provide access to a radial artery of the patient, and the delivery sheath device may be advanced to the target location via the radial artery. The incision may provide access to a thoracic cavity of the patient, and the delivery sheath device may be advanced to the target location via the thoracic cavity. The method may also include rotating, while the pump impeller is in the radially expanded operable configuration and within the pump housing, the drive shaft using a motor positioned external to the patient. The rotating the drive shaft may cause the pump impeller to rotate relative to the pump housing. The pump impeller may self-center relative to the pump housing while rotating relative to the pump housing. The delivery sheath device and the drive shaft housing may each define one or more openings. The one or more openings of the delivery sheath device may at least partially align with the one or more openings of the drive shaft housing when the pump impeller is positioned in the pump housing. In some embodiments of the method, blood flows through the aligned one or more openings of the delivery sheath device and the drive shaft housing and distally toward the pump impeller to provide a hydrodynamic bearing between the pump impeller and the pump housing. In particular embodiments, the motor and a system controller are portable and mobile with the patient such that the patient is freely ambulatory while receiving circulatory support from the percutaneous blood flow assist device. The target location may be an aortic valve region of the patient.

In another example, a method for deploying a percutaneous blood flow assist device to a target location within a patient includes advancing, through a skin opening and into a radial artery of the patient, a housing component. The housing component may include an elongate drive shaft housing defining a housing lumen, and a pump housing disposed at a distal end portion of the drive shaft housing. The pump housing may be radially reconfigurable between a low-profile configuration and a radially expanded configuration. The method may also include inserting, while the pump housing is at the target location, a rotatable inner catheter into the housing lumen of the drive shaft housing. The inner catheter may include an elongate flexible drive shaft, and a pump impeller disposed at a distal end of the drive shaft. The pump impeller may be in a radially collapsed configuration when within the housing lumen. The method may also include inflating, by supplying an inflation fluid, the pump impeller to a radially expanded operable configuration while the pump impeller is within the pump housing.

Such a method for deploying a percutaneous blood flow assist device to a target location within a patient may optionally include one or more of at least the following features. The target location may be an aortic valve region of the patient. The method may include rotating, while the pump impeller is in the radially expanded operable configuration and within the pump housing, the drive shaft using a motor positioned external to the patient. The rotating the drive shaft may cause the pump impeller to rotate relative to the pump housing. The pump impeller may tend to self-center relative to the pump housing while rotating relative to the pump housing. In some embodiments, the inflating the pump impeller comprises supplying the inflation fluid to the pump impeller via an inflation lumen of the drive shaft.

In another example, a method for deploying a percutaneous blood flow assist device to a target location within a patient includes: (i) advancing, through a skin opening and into a radial artery of the patient, one or more components of the percutaneous blood flow assist device; and (ii) expanding, at the target location, a pump impeller of the percutaneous blood flow assist device to a radially expanded operable configuration.

Such a method for deploying a percutaneous blood flow assist device to a target location within a patient may optionally include one or more of at least the following features. The target location may be an aortic valve region of the patient. The pump impeller may be attached to a distal end portion of an elongate flexible drive shaft. The method may also include rotating, while the pump impeller is at the aortic valve region and in the radially expanded operable configuration, the pump impeller by rotating the drive shaft using a motor positioned external to the patient. In some embodiments, the rotating the pump impeller causes pumping of blood from a left ventricle of the patient, across the aortic valve, and to an aorta of the patient. In particular embodiments, the pump impeller is attached to a distal end portion of an elongate flexible drive shaft. The expanding the pump impeller may be performed by supplying an inflation fluid to the pump impeller via an inflation lumen of the drive shaft.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5A illustrates an example outer sheath and housing component catheter of a mechanical hemodynamic support system in a collapsed configuration, in accordance with embodiments of the subject matter disclosed herein.

FIG. 5B illustrates a sheath of the outer catheter of FIG. 5A, in accordance with embodiments of the subject matter disclosed herein.

FIGS. 9A-9F illustrate steps for assembling and/or deploying a mechanical hemodynamic support system, in accordance with embodiments of the subject matter disclosed herein.

FIGS. 10A-10B illustrate an assembled mechanical hemodynamic support device of FIGS. 4A and 4B, in accordance with embodiments of the subject matter disclosed herein.

FIG. 11 illustrates interaction between an example pump impeller and an example pump housing, in accordance with embodiments of the subject matter disclosed herein.

FIGS. 13A-13B illustrate example pump impellers, example pump housings, and blood flow characteristics, in accordance with embodiments of the subject matter disclosed herein.

FIGS. 14A-14B illustrate example pump impellers, example pump housings, and blood flow characteristics, in accordance with embodiments of the subject matter disclosed herein.

FIGS. 15A-15C illustrate example pump impellers, example pump housings, and a miniature implantable motor, in accordance with embodiments of the subject matter disclosed herein.

FIGS. 16A-16B illustrate an example inflation needle used for expanding certain pump impellers, in accordance with embodiments of the subject matter disclosed herein.

FIGS. 17A-17C illustrate steps for expanding a pump impeller and coupling the drive shaft to an external motor, in accordance with embodiments of the subject matter disclosed herein.

FIGS. 19A-19B illustrate an example braid supported inlet cannula and pump housing, in accordance with embodiments of the subject matter disclosed herein.

FIGS. 20A-20B illustrate an example coil supported inlet cannula and a non-supported pump housing, in accordance with embodiments of the subject matter disclosed herein.

FIGS. 23A-23B illustrate an example mechanical hemodynamic support device including an aortic valve-engaging skirt, in accordance with embodiments of the subject matter disclosed herein.

FIGS. 24A-24B illustrate an example mechanical hemodynamic support device including aortic valve-engaging petals, in accordance with embodiments of the subject matter disclosed herein.

FIGS. 28A-28F illustrate an example pump housing and blood exit ports, in accordance with embodiments of the subject matter disclosed herein.

FIGS. 29A-29C illustrate example pump housing and blood exit port angles, in accordance with embodiments of the subject matter disclosed herein.

FIG. 30 illustrates an example catheter delivery sheath, in accordance with embodiments of the subject matter disclosed herein.

FIGS. 31A-31C illustrate example tear-away catheter delivery sheaths, in accordance with embodiments of the subject matter disclosed herein.

FIG. 32 illustrates an example catheter delivery sheath with blood perfusion holes, in accordance with embodiments of the subject matter disclosed herein.

FIGS. 33A-33B illustrate an example catheter delivery sheath with a proximal cutout, in accordance with embodiments of the subject matter disclosed herein.

FIGS. 34A-34C illustrate an example housing component, in accordance with embodiments of the subject matter disclosed herein.

FIGS. 38A-38E illustrate example drive shafts of a mechanical hemodynamic support system, in accordance with embodiments of the subject matter disclosed herein.

FIGS. 39A-39C further illustrate the drive shafts of FIGS. 38A-38E and potential failure modes thereof.

FIGS. 40A-40D illustrate an example drive shaft and drive shaft hub of a mechanical hemodynamic support system, in accordance with embodiments of the subject matter disclosed herein.

FIGS. 41A-41B illustrate an example expandable impeller of a mechanical hemodynamic support device, in accordance with embodiments of the subject matter disclosed herein.

FIGS. 42A-42B illustrate an example braid supported expandable impeller of a mechanical hemodynamic support device, in accordance with embodiments of the subject matter disclosed herein.

FIGS. 43A-43C illustrate an example triangular, structure supported expandable impeller of a mechanical hemodynamic support device, in accordance with embodiments of the subject matter disclosed herein.

FIGS. 44A-44C illustrate an example expandable impeller with ridges of a mechanical hemodynamic support device, in accordance with embodiments of the subject matter disclosed herein.

FIGS. 45A-45C illustrate an example expandable impeller with spiraling ridges of a mechanical hemodynamic support device, in accordance with embodiments of the subject matter disclosed herein.

FIGS. 46A-46D illustrate an example expandable impeller with valleys of a mechanical hemodynamic support device, in accordance with embodiments of the subject matter disclosed herein.

FIGS. 47A-47C illustrate an example expandable impeller with spiraling valleys of a mechanical hemodynamic support device, in accordance with embodiments of the subject matter disclosed herein.

FIGS. 48A-48B illustrate an example expandable impeller with a variation of the proximal surface profile of a mechanical hemodynamic support device, in accordance with embodiments of the subject matter disclosed herein.

FIGS. 49A-49B illustrate an example expandable impeller with a variation of the proximal surface profile of a mechanical hemodynamic support device, in accordance with embodiments of the subject matter disclosed herein.

FIGS. 50A-50B illustrate an example expandable impeller with a variation of the proximal surface profile of a mechanical hemodynamic support device, in accordance with embodiments of the subject matter disclosed herein.

FIGS. 51A-51B illustrate an example expandable impeller with a variation of the distal end for a blood pushing configuration of a mechanical hemodynamic support device, in accordance with embodiments of the subject matter disclosed herein.

FIGS. 52A-52D illustrate another example expandable impeller of a mechanical hemodynamic support device, in accordance with embodiments of the subject matter disclosed herein.

FIGS. 53A-53C illustrate another example expandable impeller of a mechanical hemodynamic support device, in accordance with embodiments of the subject matter disclosed herein.

FIGS. 55A-55D illustrate another example expandable impeller of a mechanical hemodynamic support device, in accordance with embodiments of the subject matter disclosed herein.

FIGS. 58A-58C illustrate components and steps of an example method for manufacturing another expandable impeller, in accordance with embodiments of the subject matter disclosed herein.

FIGS. 58D-58E illustrate an expandable impeller created by the method illustrated in FIGS. 58A-58C, in accordance with embodiments of the subject matter disclosed herein.

FIGS. 59A-59B illustrate components and steps of an example method for manufacturing another expandable impeller, in accordance with embodiments of the subject matter disclosed herein.

FIG. 59C illustrates an expandable impeller created by the method illustrated in FIGS. 59A-59B, in accordance with embodiments of the subject matter disclosed herein.

FIGS. 60A-60B illustrate an example method of using a pressurized balloon in a patient's cardiovascular system to act as a pressure transducer and thereby provide measurements of the patient's systolic and diastolic pressure.

Figure 1:
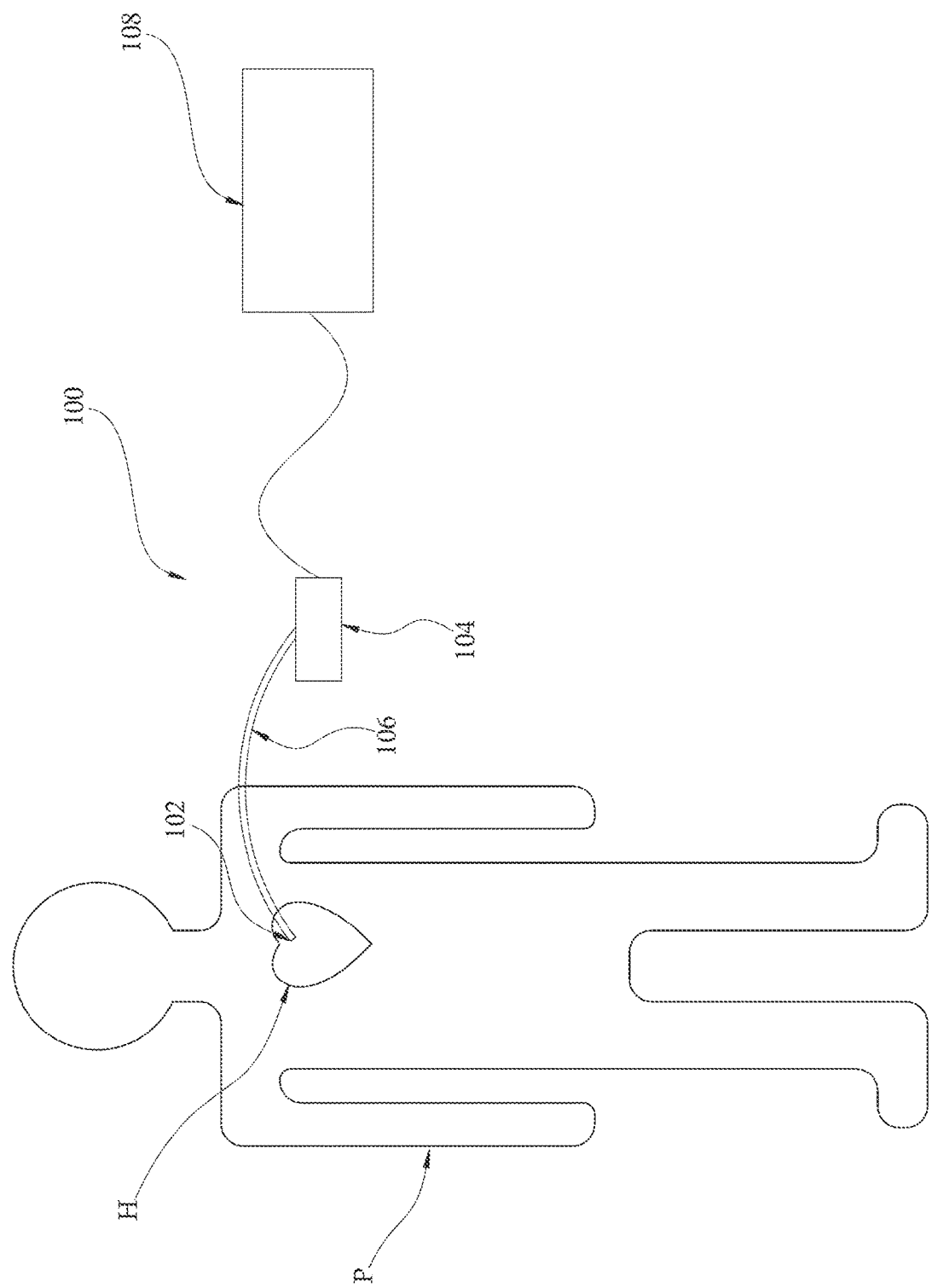
FIG. 1 schematically illustrates an example mechanical hemodynamic support system providing hemodynamic support to a patient, in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Mechanical hemodynamic support devices, such as percutaneous ventricular assist devices ("pVADs") according to embodiments of the present disclosure, are capable of unloading or assisting the heart of a patient for a period of time during, for example, a myocardial infarction, cardiogenic shock, a surgical or interventional procedure, and the like.

In some embodiments, the pVAD devices described herein have a sufficiently small profile to facilitate deployment through a sheath placed in a radial artery access site. Some such embodiments of the pVAD devices described herein have an innovative two-part design that allows very small delivery profiles as required by the radial artery access site, for example. The pVAD devices described herein can also be deployed via other vascular access sites such as, but not limited to, the femoral artery, the axillary artery, and the venous system, to provide a few non-limiting examples.

After the device has been advanced to a desired location, or a target location, for example within the heart of a patient, it is radially expanded from its entry profile, also referred to as a low-profile or collapsed configuration, to its functional pumping size, also referred to as an expanded or operable configuration. Devices according to embodiments of the present disclosure can be configured to provide various flow outputs based upon factors such as, but not limited to, size, impeller design, and impeller rotational speed.

As used herein, the terms "proximal" and "distal" pertain to the orientation of the devices, not the patient. For example, proximal portions of the devices described herein may reside outside of the patient for manipulation by a clinician operator, while distal portions of the devices are residing within the patient.

In some cases, the pump devices described herein are referred to have a blood "pushing" configuration or a blood "pulling" configuration. In this disclosure, "pushing" is used to describe a pumping arrangement by which blood is caused to flow in a direction from proximal to distal. In this disclosure, "pulling" is used to describe a pumping arrangement by which blood is caused to flow in a direction from distal to proximal.

FIG. 1 schematically illustrates an example mechanical hemodynamic support system 100 (or pVAD 100) providing hemodynamic support to a patient P, in accordance with some embodiments of the subject matter disclosed herein. The system 100 includes a mechanical hemodynamic support device 102 (also referred to herein as a "pump device" or "blood pump") that can be positioned at least partially in the patient's heart H. In the illustrated embodiment, the system 100 includes an external motor 104 (located external to the patient P) that is coupled to the device 102 to drive the device 102 using a torque-transmitting elongate flexible drive shaft 106. The proximal end of the drive shaft 106 is coupled to the motor 104 and the distal end of the drive shaft 106 is coupled to the pump device 102. In other words, the drive shaft 106 is partially external to the patient P and partially internal to the patient P.

The motor 104 is controlled by a system controller 108, which controls the speed of the motor 104 and monitors performance of the motor 104. The controller 108 also provides an interface of the system 100 for a clinician operator to set-up and operate the system 100. The system controller 108 may be a separate system (as shown) or may be an integrated system that also houses the motor 104.

Figure 2:
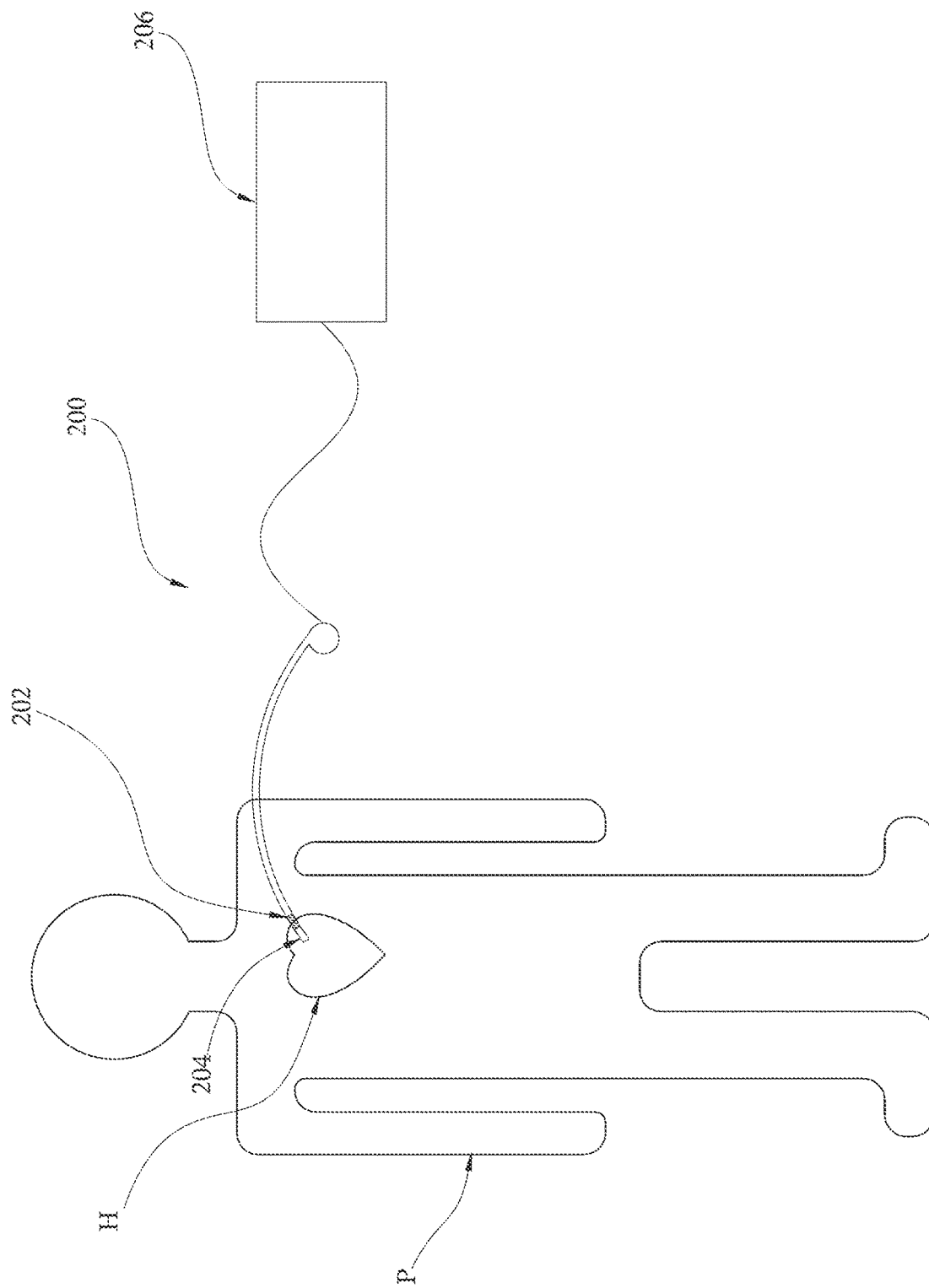
FIG. 2 schematically illustrates another example mechanical hemodynamic support system providing hemodynamic support to a patient, in accordance with embodiments of the subject matter disclosed herein.

FIG. 2 illustrates another example mechanical hemodynamic support system 200 providing hemodynamic support to a patient P, in accordance with embodiments of the subject matter disclosed herein. In this embodiment, the system 200 includes an internal motor 202 (positioned internally within the patient P) that is coupled to and drives a mechanical hemodynamic support device 204 positioned at least partially in the patient's heart H. The motor 202 is controlled by a system controller 206, which controls the speed of the motor 202 and monitors the performance of the motor 202. The controller 206 also provides an interface of the system 200 for a clinician operator to set-up and operate the system 200.

With general reference to FIGS. 1 and 2, the motors used to drive the pump may be any motor capable of high speed rotation, such as but not limited to, a brushless motor, a brushed DC motor, or a pneumatically driven turbine.

Figure 3:
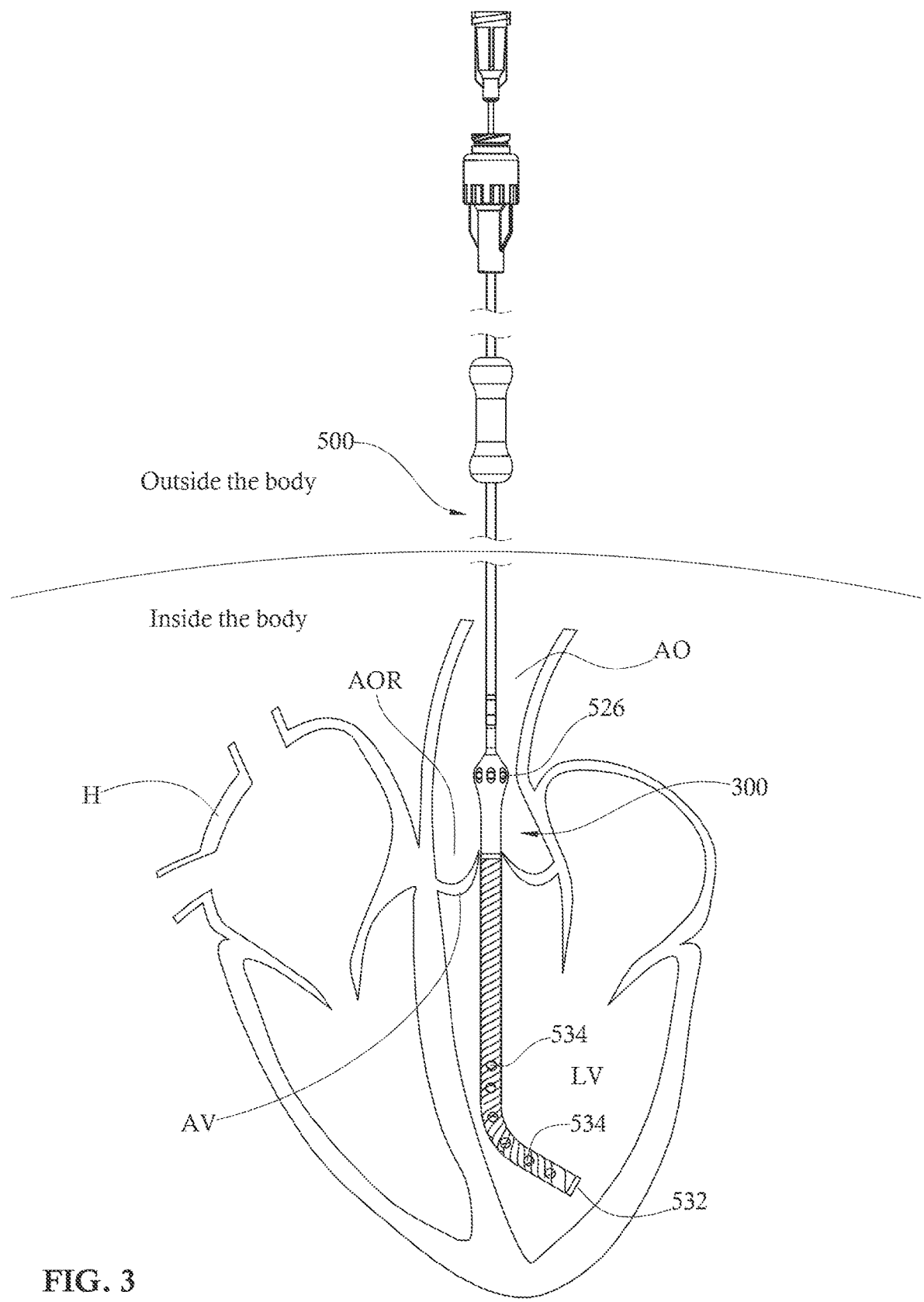
FIG. 3 illustrates an example mechanical hemodynamic support device positioned in the heart of a patient in a blood pulling arrangement, in accordance with embodiments of the subject matter disclosed herein.

FIG. 3 illustrates an example mechanical hemodynamic support device 300 (or "pump device 300") positioned in the heart H of a patient in a blood pulling arrangement, in accordance with some embodiments of the subject matter disclosed herein. The pump device 300 may represent, for example, the device 102 of the system 100 (FIG. 1) or the device 204 of the system 200 (FIG. 2).

In the illustrated arrangement, the pump device 300 reaches the heart H by advancing it via a vascular access site and the vasculature of the patient while a housing component of the pump device 300 is contained in a low-profile delivery configuration within a delivery sheath component 500 (or sheath 500), as described further below. In the depicted example, the sheath 500 containing the housing component of the pump device 300 is advanced into the aorta AO, and then partially across the aortic valve AV to the position as shown. In that position, the sheath 500 is then pulled proximally by a clinician to express the housing component of the pump device 300. The housing component will expand when expressed from the sheath 500. Then, as described further below, a separate inner catheter comprising a pump impeller and flexible drive shaft is advanced by the clinician into the housing component to construct or assemble the two-part pump device 300 in vivo.

In the depicted embodiment, the distal tip portion of the pump device 300 defines one or more blood inlets 534 through the sidewall of the housing component of the pump device 300 and one or more end inlets 532 through the distal tip of the housing component of the pump device 300. The pump device 300 draws blood out of the ventricle LV via the inlets 532/534 and then delivers the blood at a higher pressure to the aortic root AOR via one or more blood outlets 526 positioned in the aortic root AOR. The plurality of sidewall blood inlets 534 may be located distal of the AV when positioned properly within the anatomy, thereby eliminating the potential for blood from the aorta to enter the inlet cannula and pump through the sidewall blood inlets 534. The blood is then circulated throughout the body of the patient by the vasculature of the patient.

Figure 4A:
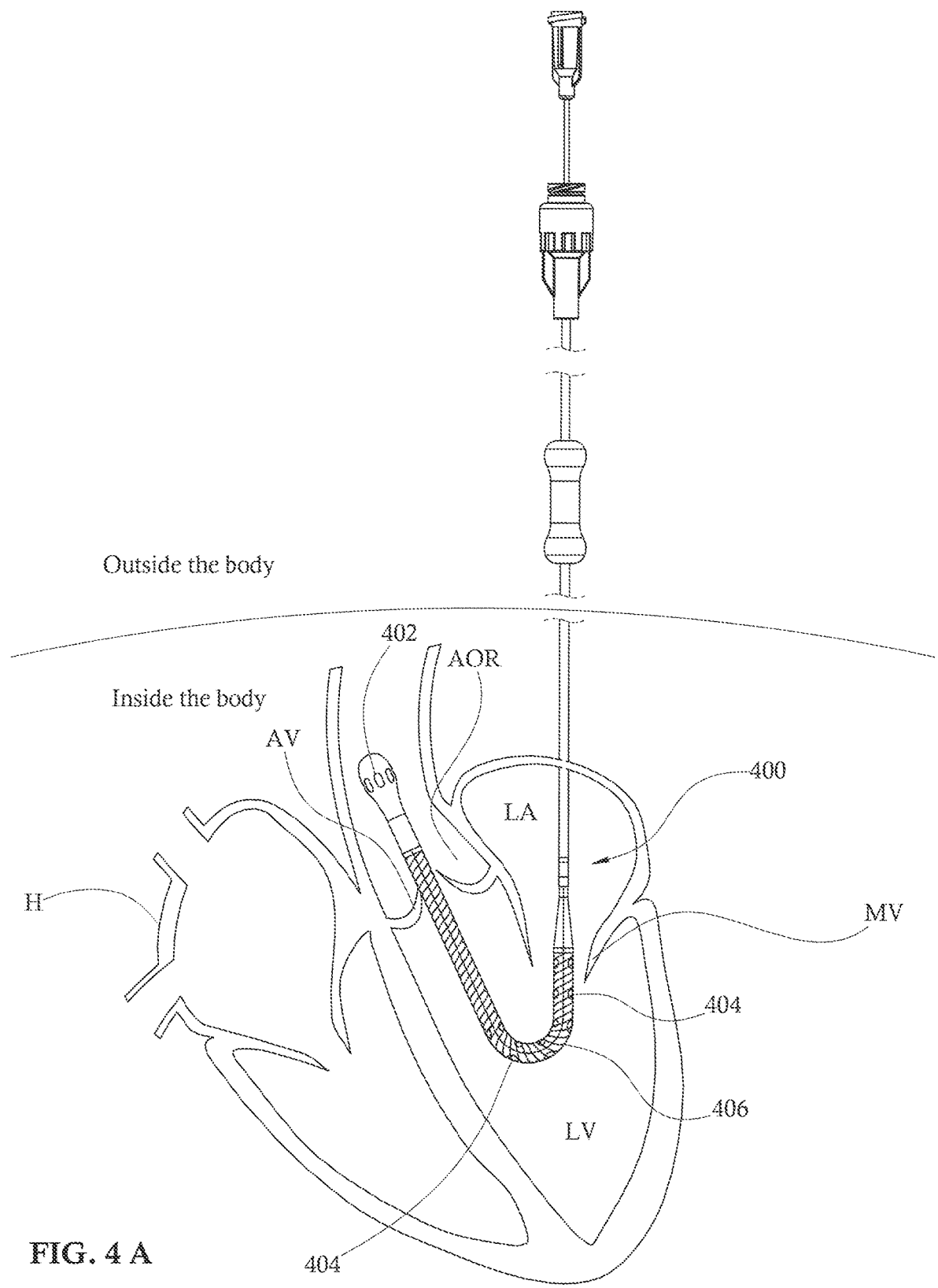
FIG. 4A illustrates another example mechanical hemodynamic support device positioned in the heart of a patient in a blood pushing arrangement, in accordance with embodiments of the subject matter disclosed herein.

FIG. 4A illustrates another example mechanical hemodynamic support device 400 (or "pump device 400") positioned in the heart H of a patient in a blood pushing arrangement, in accordance with embodiments of the subject matter disclosed herein. The device 400 may represent, for example, the device 102 of the system 100 (FIG. 1) or the device 204 of the system 200 (FIG. 2). In the illustrated arrangement, the device 400 reaches the heart H by advancing it through a trans-septal pathway, into the left atrium LA, across the mitral valve MV, and then across the aortic valve AV to the position as shown. The distal tip portion of the device 400 defines one or more blood outlets 402 positioned in the aortic root AOR. The one or more blood inlets 404 of the device 400 are positioned in the left ventricle LV, and may comprise one or more fenestrations or openings defined through the sidewall of an inlet cannula 406 of the device 400.

FIG. 4B illustrates the mechanical hemodynamic support device 400 positioned in the heart H of a patient in another blood pushing arrangement, in accordance with embodiments of the subject matter disclosed herein. The device 400 may represent, for example, the device 102 of the system 100 (FIG. 1) or the device 204 of the system 200 (FIG. 2). In the illustrated arrangement, the device 400 reaches the heart H by advancing it via a thoracic cavity of the patient, through the apex of the heart H, into the left ventricle LV, and across the aortic valve AV to the position as shown. The distal tip portion of the device 400 defines the one or more blood outlets 402 positioned in the aortic root AOR. The one or more blood inlets 404 of the device 400 are positioned in the left ventricle LV and may comprise one or more fenestrations or openings defined through the sidewall of an inlet cannula 406 of the device 400.

FIG. 5A illustrates an example delivery sheath device 500 that can be used to deliver the housing components of the pump devices described herein while the housing components of the pump devices are in a low-profile radially collapsed configuration. The delivery sheath 500 includes a handle 512 and a sheath 502 that distally extends from the handle 512. The sheath 502 defines a lumen in which the housing component of the pump devices described herein can be slidably disposed while radially constrained by the sheath 502 in the low-profile radially collapsed configuration.

A housing component 510 is also shown in FIG. 5A. The housing component 510 is a first portion of the two-part pump devices described herein, and is described further below. A distal end portion of the housing component 510 is disposed within the lumen of the sheath 502 in a low-profile radially collapsed configuration. The housing component 510 is configured to receive a separate pump impeller and associated drive shaft as described below.

FIG. 5B illustrates a longitudinal cross-sectional view of a distal portion of the sheath 502 containing the distal end portion of the housing component 510 in its low-profile radially collapsed configuration. The distal end portion of the housing component 510 includes an inlet cannula 504, a pump housing 508, and a drive shaft housing 511.

The sheath 502 of the delivery sheath device 500 holds the expandable inlet cannula 504 and pump housing 508 in a collapsed configuration during delivery to a target location within a patient. In the depicted embodiment, the distal tip portion of the sheath 502 includes an atraumatic bumper tip 506 to inhibit injury to the patient's vasculature and/or heart when the device is advanced through the patient's anatomy.

The proximal end of the pump housing 508 is coupled to the distal end of the drive shaft housing 511. After the delivery sheath device 500 is advanced to the target location, the sheath handle 512 may be pulled proximally by the clinician, thereby unsheathing the inlet cannula 504 and pump housing 508 to allow those components to expand to their enlarged operational configurations.

Figure 6:
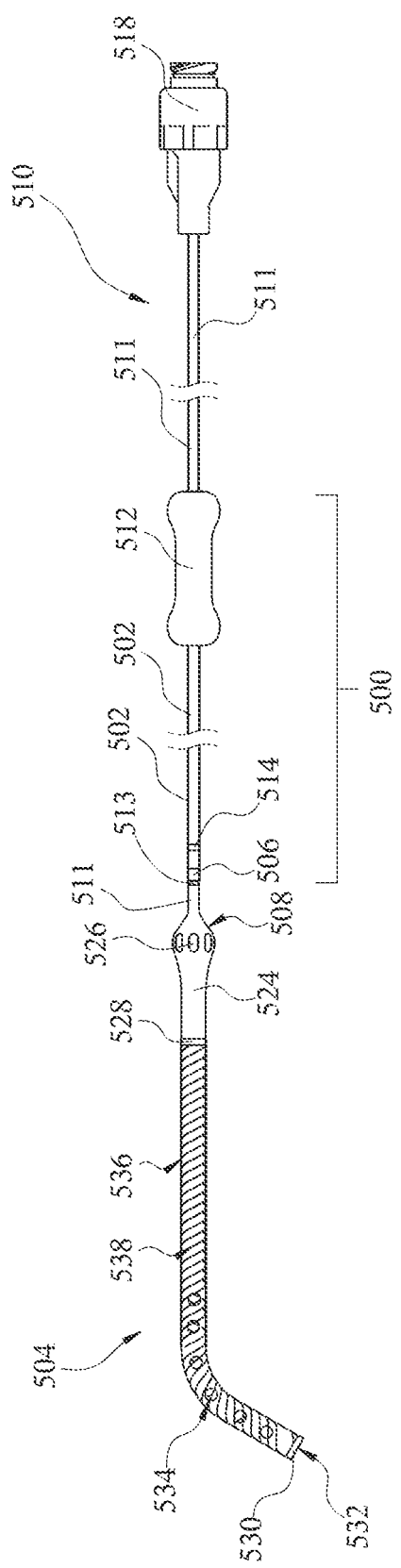
FIG. 6 illustrates the housing component catheter of FIG. 5 in an expanded configuration.

FIG. 6 illustrates the delivery sheath device 500 and the housing component 510 after the delivery sheath device 500 has been pulled proximally in order to express the inlet cannula 504 and the pump housing 508 of the housing component 510 from the lumen of the sheath 502. When expressed from the sheath 502, the inlet cannula 504 and the pump housing 508 can expand to reconfigure to their expanded configurations as shown. The housing component 510 is an example of the first part of the two-part pump devices described herein.

In some embodiments, the clinician operator may stop retracting the delivery sheath device 500 based on an indication that a radiopaque distal marker band 514 on a distal portion of the sheath 502 has moved proximally of a radiopaque marker 513 located on the drive shaft housing 511.

A drive shaft housing hub 518 may be disposed on a proximal end of a drive shaft housing 511. The pump housing 508 may be disposed on the distal end of the drive shaft housing 511. The drive shaft housing 511 can include a multi-filar coil or braid on the inside wall, or embedded within the wall, of a polymeric tube that comprises the drive shaft housing 511. In some embodiments, the inner wall of the drive shaft housing 511 includes an abrasion resistant material to withstand contact with the rapidly rotating drive shaft.

In some embodiments, the pump housing 508 is or comprises a volute. The pump housing 508 includes a flexible wall 524 that defines one or more blood flow outlets 526.

The inlet cannula 504 may include a radiopaque marker at its proximal end 528 and/or at its distal end 530. The inlet cannula 504 may include one or more end inlets 532 and/or one or more side inlets 534 to permit blood flow into the inlet cannula 504. The inlet cannula 504 may include a flexible wall 536 with a support structure 538, such as a coil, embedded within the wall 536 or disposed circumferentially around the wall 536. The radiopaque marker at the proximal end 528 of the cannula 504 may be aligned with the aortic valve within the anatomy, which facilitates positioning the pump housing 508 within the aortic root/ascending aorta, and positioning the inlet cannula 504 in the left ventricle.

The inlet cannula 504 and the pump housing 508 may have sufficient structural support to maintain their shape and facilitate efficient pumping while also being sufficiently supple and flexible to ensure the device can navigate the vasculature and reach the target vasculature without causing vessel damage, as well as being deployed and pumping blood for an extended period of time without causing damage to the targeted anatomy such as the heart, valves, or greater vessels.

Figure 4:
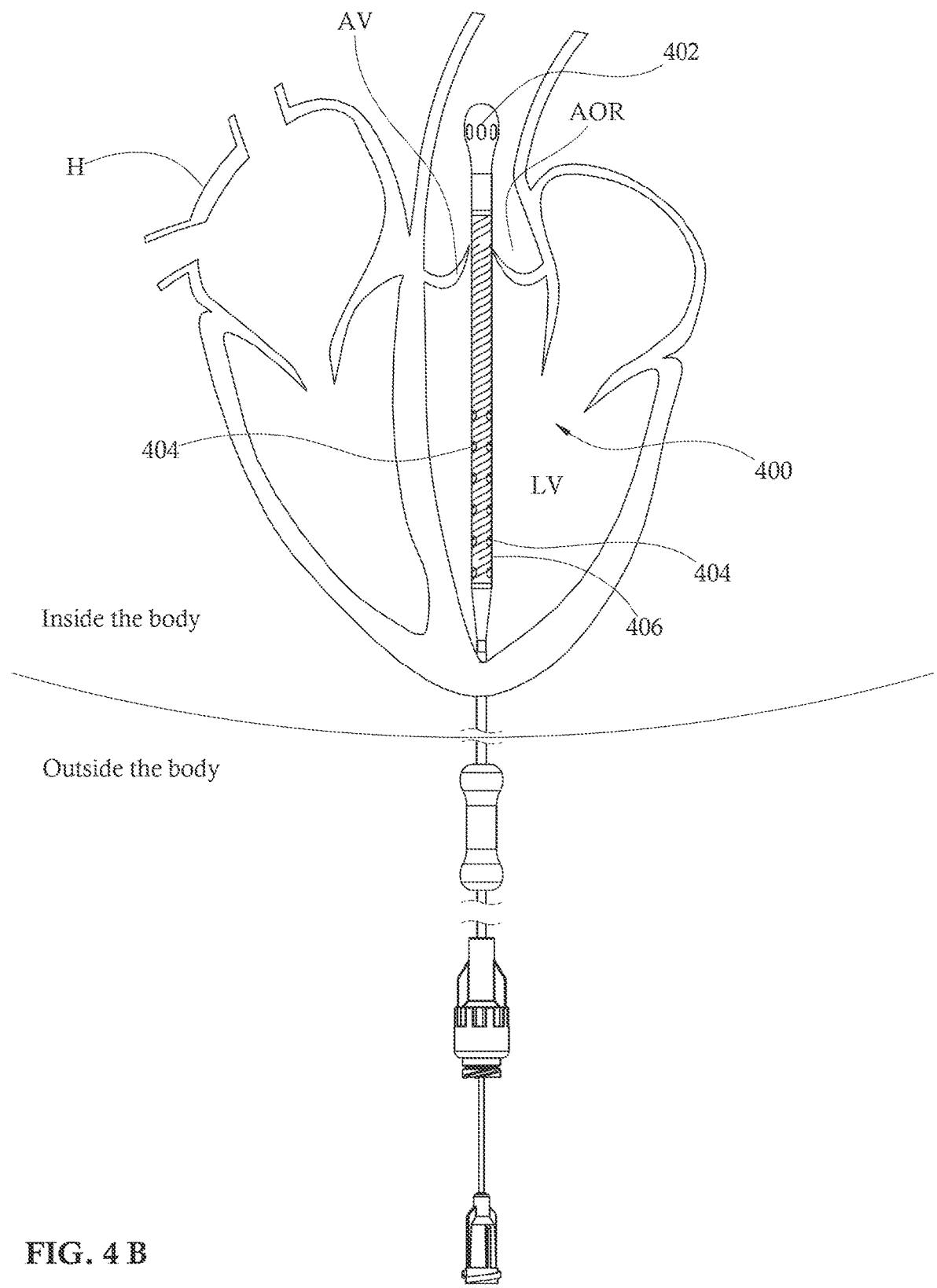
FIG. 4B illustrates another example mechanical hemodynamic support device positioned in the heart of a patient in a blood pushing arrangement, in accordance with embodiments of the subject matter disclosed herein.
Figure 7:
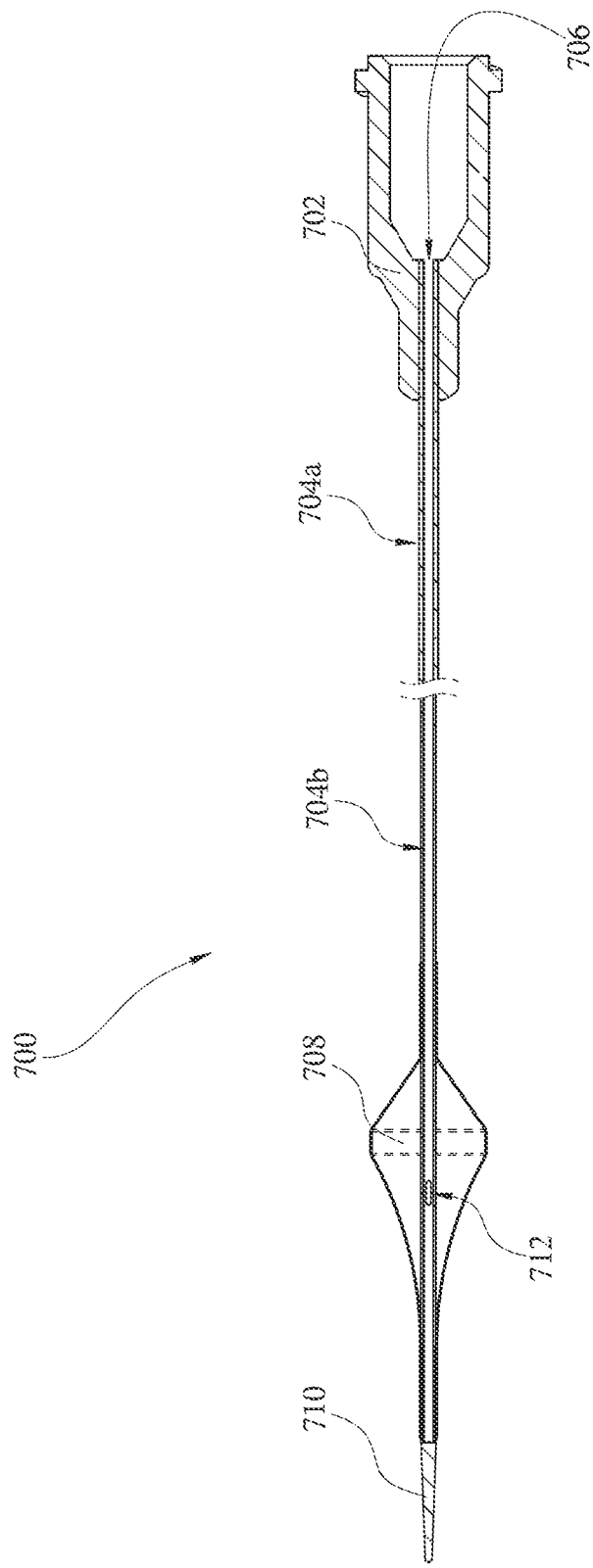
FIG. 7 illustrates an example rotatable inner catheter of a mechanical hemodynamic support system in an expanded configuration, in accordance with embodiments of the subject matter disclosed herein.

FIG. 7 illustrates an example rotatable inner catheter 700 in an expanded configuration, in accordance with embodiments of the subject matter disclosed herein. The inner catheter 700 is an example of the second part of the two-part pump systems described herein. The inner catheter 700 may be, for example, part of a blood pulling pump device, such as the pump device 300 (FIG. 3), and may be positionable in the housing component 510, as described further below. However, it is understood that other types of rotatable inner catheters with similar features may be, for example, part of a blood pushing pump device, such as the device 400 (FIG. 4).

The inner catheter 700 is slidably disposable in a lumen defined by the housing component 510. As described further below, the inner catheter 700 can be inserted in the lumen defined by the housing component 510 after the inlet cannula 504 and the pump housing 508 of the housing component 510 have been positioned in the heart and aorta (or other target location) and radially expanded as a result of pulling back the delivery sheath device 500.

The inner catheter 700 includes an elongate flexible drive shaft that, in this example, includes a proximal drive shaft portion 704*a* and a distal drive shaft portion 704*b*. In the depicted embodiment, the proximal drive shaft portion 704*a* has a larger diameter than the distal drive shaft portion 704*b*, although this is not required in all embodiments. The combination of the proximal drive shaft portion 704*a* and the distal drive shaft portion 704*b* can be referred to as a drive shaft 704.

As depicted, the inner catheter 700 may also include a drive shaft hub 702 disposed at a proximal end portion of the proximal drive shaft portion 704*a*. An expandable pump impeller 708 is disposed at a distal end portion of the distal drive shaft portion 704*b*.

In some embodiments, the expandable pump impeller 708 is inflatable and deflatable. In some such embodiments, the drive shaft hub 702 and lumen defined by the drive shaft 704 permits delivery of an inflation fluid, such as saline, via an inflation lumen 706 to the inflatable impeller 708. The distal drive shaft portion 704b can define one or more sidewall openings 712 via which the inflation fluid can pass between the lumen 706 and the interior of the inflatable impeller 708.

In some embodiments, such as the depicted embodiment, the drive shaft 704 extends through the pump impeller 708 to a drive shaft tip portion 710 that extends distally from the pump impeller 708. In some embodiments, the drive shaft tip portion 710 may be fully or partially radiopaque to facilitate identification under fluoroscopy.

With general reference to both FIGS. 6 and 7, after the delivery sheath device 500 (containing the housing component 510 in its low-profile radially constrained configuration) is positioned at the target location within the patient, the delivery sheath device 500 can be pulled proximally relative to the housing component 510 to allow the housing component 510 to reconfigure to its expanded configuration. After that, the inner catheter 700 can be advanced through the drive shaft housing 511 until the impeller 708 is positioned in the pump housing 508. The impeller 708 may then be inflated to the expanded configuration (as shown), which is its operational fluid pumping configuration. The inner catheter 700 may then be connected to the motor 104 (e.g., see FIG. 1) and rotated to create a fluid pressure gradient and thereby cause blood flow into the inlet cannula 504, to the pump housing 508, and out through the outlets 526 of the pump housing 508.

FIGS. 8A-8E illustrate exemplary sequential steps for delivering and assembling, in vivo, a blood pulling mechanical hemodynamic support device within a patient, for use as part of the system 100 (e.g., FIG. 1), in accordance with embodiments of the subject matter disclosed herein. The illustrated example blood pulling two-part pump device 300 includes the housing component 510 (e.g., see FIGS. 5A, 5B, and 6) and the separate inner catheter (e.g., see FIG. 7). The housing component 510 can be delivered to the target location using the delivery sheath device 500 (e.g., see FIGS. 5A, 5B, and 6).

First, an access site, such as a radial access site, femoral access site, or other, is formed in the patient. In some embodiments, a guidewire is advanced within the patient's vasculature to the target location (e.g., across the aortic valve). In some embodiments, no such guidewire is used.

Figure 8A:
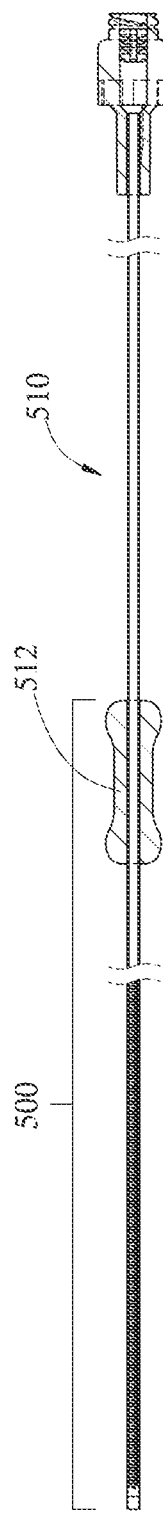
FIGS. 8A-8E illustrate steps for assembling and/or deploying a mechanical hemodynamic support system, in accordance with embodiments of the subject matter disclosed herein.

Next, and as illustrated in FIG. 8A, the delivery sheath device 500 containing the distal portion of the housing component 510 is advanced through the access site and tracked to the target location within the patient's anatomy (for example, using fluoroscopic or other imaging guidance in some embodiments).

Figure 8B:
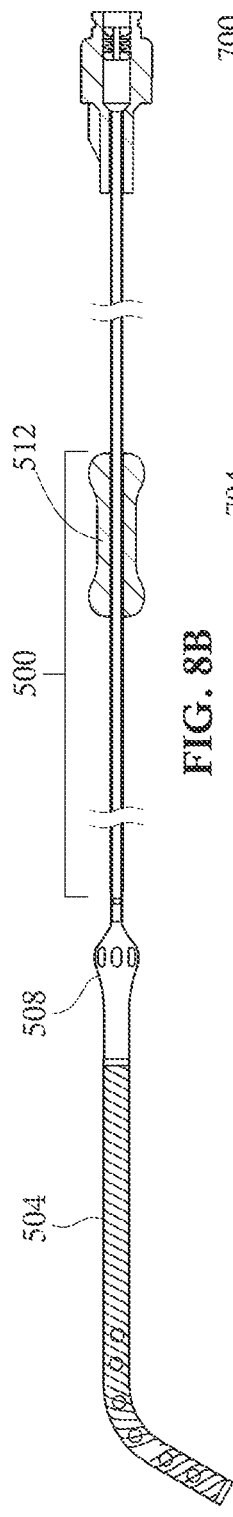

Next, and as illustrated in FIG. 8B, the delivery sheath device 500 is retracted by pulling proximally on the sheath handle 512, thereby expressing the inlet cannula 504 and pump housing 508. This is the first part of the two-part blood pump system. When the inlet cannula 504 and the pump housing 508 are expressed from the delivery sheath device 500, the inlet cannula 504 and the pump housing 508 expand radially to their expanded configurations. The guidewire, if used, may then be fully retracted.

Figure 8C:
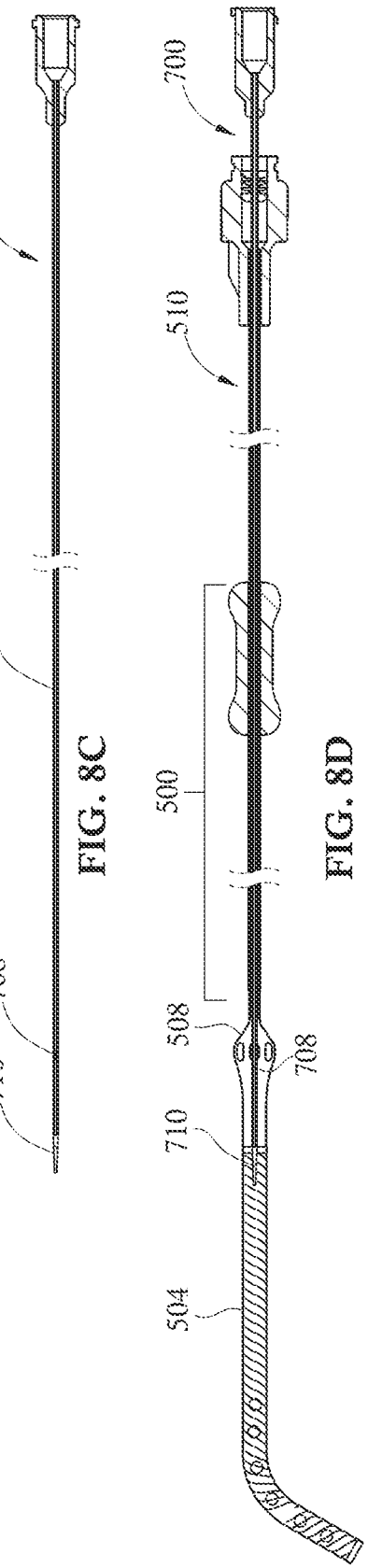
Figure 8D:
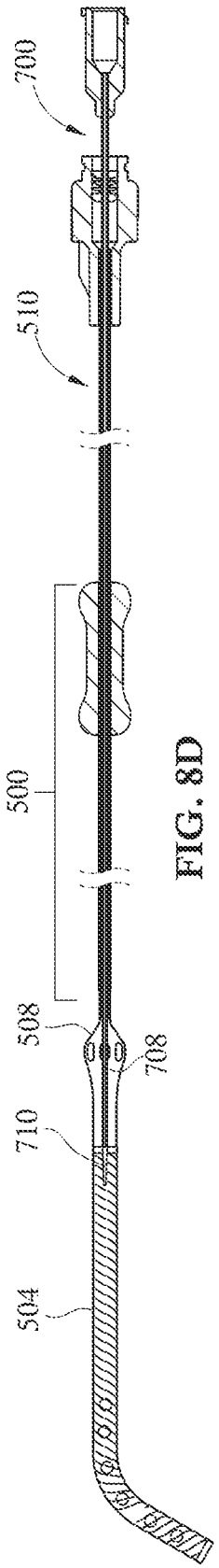

Next, the rotatable inner catheter 700 in its radially contracted configuration (with the impeller 708 deflated) as depicted in FIG. 8C may be advanced within the housing component 510. That is, the rotatable inner catheter 700 is inserted into the hub and lumen of the housing component 510 and advanced distally to arrive at the arrangement illustrated in FIG. 8D in which the impeller 708, still in its contracted configuration, is positioned within the pump housing 508. The rotatable inner catheter 700 is the second part of the two-part blood pump system.

Figure 8E:
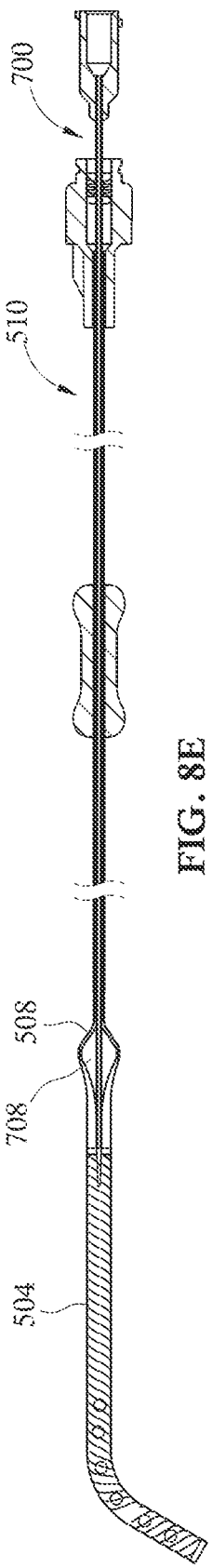

Next, and as illustrated in FIG. 8E, the impeller 708 is inflated and expanded within the pump housing 508. Thereafter, the rotatable inner catheter 700 and its impeller 708 may be rotated by a motor located external to the patient (e.g., see FIG. 1) to provide blood flow and hemodynamic support to the patient.

FIGS. 9A-9F illustrate sequential steps for delivering and assembling, in vivo, a blood pulling mechanical hemodynamic support device within a patient, for use as part of the system 200 (e.g., FIG. 2), which comprises a blood pump with an internal motor disposed near the distal tip of the catheter system, in accordance with embodiments of the subject matter disclosed herein. The illustrated blood pulling pump device 300 includes the pumping unit 900 and an impeller inflation needle 1600. The pumping unit 900 includes a drive shaft housing, an internal motor 202 disposed toward the distal end of the drive shaft housing and coupled to a short drive shaft and impeller 708 which extend distally from the motor 202, as well as a pump housing 508 and inlet cannula 504 which also extend distally from the motor 202 and surround the impeller 708. The pumping unit 900 is delivered to the target location using the delivery sheath device 500.

First, an access site, such as a radial access site, femoral access site, or other, is formed in the patient. In some embodiments, a guidewire is advanced within the patient's vasculature to the target location (e.g., across the aortic valve). Next, and as illustrated in FIG. 9A, the delivery sheath device 500 containing the distal portion of the pumping unit 900 is advanced through the access site and tracked to the target location within the patient's anatomy (for example, via the previously-positioned guidewire in some embodiments).

Next, and as illustrated in FIG. 9B, the delivery sheath device 500 is retracted by pulling proximally on the sheath handle 512, thereby expressing the inlet cannula 504 and pump housing 508, as well as expressing the impeller in its radially contracted configuration (with the impeller 708 deflated) and the miniature motor 202. With this system driven by the miniature internal motor 202, the impeller 708 may be deployed simultaneously with the housing 508. When the inlet cannula 504 and the pump housing 508 are expressed from the delivery sheath device 500, the inlet cannula 504 and the pump housing 508 expand radially to their expanded configurations. The guidewire, if used, may then be fully retracted, thereby opening up a passage within the pumping unit 900 for inflation of the impeller 708.

Next, an impeller inflation needle 1600 as depicted in FIG. 9C may be advanced within the pumping unit 900. That is, inflation needle 1600 is inserted through the hub and lumen of the pumping unit 900 and advanced distally to arrive at the arrangement illustrated in FIG. 9D in which the distal tip 1602 of the inflation needle 1600 is positioned within the impeller 708.

Next, and as illustrated in FIG. 9E, the impeller 708 is inflated and expanded within the pump housing 508 by applying the pressure of an inflation medium (e.g., saline) to the hub 1606 of the inflation needle 1600 that passes into the impeller 708 via an opening at the distal tip 1602 of the inflation needle 1600. Once the impeller 708 is expanded to its pumping profile, the inflation needle 1600 may be fully removed from catheter system as illustrated in FIG. 9F. Thereafter, the miniature internal motor 202 may be activated to rotate the impeller 708 (e.g., FIG. 2) to provide blood flow and hemodynamic support to the patient.

FIGS. 10A and 10B illustrate the blood pushing mechanical hemodynamic support device 400 that is designed for use as part of the system 100 (FIG. 1), in accordance with embodiments of the subject matter disclosed herein. In some cases, the pump device 400 can be positioned in the patient and operated in the configuration shown in FIG. 4A. In other cases, the pump device 400 can be positioned in the patient and operated in the configuration shown in FIG. 4B. In still other cases, the pump device 400 can be positioned in the patient and operated in other arrangements relative to the patient.

The pump device 400 includes a housing component 510' and a rotatable inner catheter 700'. In a manner analogous to the description above regarding the pump device 300, the delivery sheath device 500 is used to contain the housing component 510' in a radially compressed low-profile delivery configuration during advancement to the target location within the patient's anatomy. In some cases, the advancement takes place over a previously placed guidewire.

If advancement takes place over a previously place guidewire, with the pump housing 408 being the most distal portion of the housing component 510', the pump housing 408 may be designed to have a distal hole for a guidewire to pass through the pump housing 408. Alternatively, the pump housing 408, when in its collapsed, radially contracted state, may be folded in such a way so as to allow a guidewire to enter the contracted pump housing 408 through one of the pump housing exit ports 402, thereby facilitating catheter placement in the anatomy through the use of advancement over a guidewires.

After the advancement of the delivery sheath device 500 and the housing component 510', the clinician operator can pull the delivery sheath device 500 proximally to unsheathe the pump housing 408 and the inlet cannula 406. The pump housing 408 and the inlet cannula 406 are thereby allowed to expand radially to the configurations shown. The guidewire, if used, can then be fully retracted. Thereafter, a rotatable inner catheter 700' with its pump impeller 708' in a deflated state can be inserted into the housing component 510' via the hub and lumen of the housing component 510'. When the impeller 708' is within the pump housing 408, inflation fluid can be delivered to the impeller 708' via the lumen of the rotatable inner catheter 700' in order to inflate and expand the impeller 708' to the operable configuration shown (FIG. 10B). The rotatable inner catheter 700' and its impeller 708' may then be rotated by a motor located external to the patient (e.g., FIG. 1) to provide blood flow and hemodynamic support to the patient.

FIG. 11 illustrates certain interactions between the impeller 708 and the pump housing 508 of the pump device 300 (e.g., FIG. 3), in accordance with embodiments of the subject matter disclosed herein. As the impeller 708 is driven to rotate, the impeller 708 and the pump housing 508 cooperate to act as a centrifugal pump. That is, the rotating impeller 708 exerts centrifugal force on the blood and thereby flings blood outwardly against the inner wall of the pump housing 508. The centrifugal force causes the pressure of the blood to increase as it approaches a maximum diameter portion 1100 of the impeller 708, because the centrifugal forces increase along the tapered diameter of the impeller 708. The outlets 526 defined by the pump housing 508 may be positioned radially around the maximum diameter portion 1100 of the impeller 708. The outlets 526 permit the high pressure blood to exit the pump housing 508 and enter the aorta.

As the impeller 708 rotates within the pump housing 508, the blood surrounding the impeller 708 creates a hydrodynamic bearing that causes the impeller 708 to self-center within the pump housing 508 and rotate while the longitudinal axes of the impeller 708 and pump housing 508 are aligned. Antegrade blood flow 1102, represented by larger arrows, originating from the cannula (shown elsewhere) constitutes the majority of the blood flow, and retrograde flow 1104, represented by smaller arrows, constitutes only a small amount of the blood flow. Accordingly, the rotating impeller 708 may not require conventional mechanical bearings or bushings (conventional mechanical bearing or bushings being defined as physical solid components). In other words, this is a bearing-less two-part blood pump in some embodiments. Instead, the design of the impeller 708 within the pump housing 508 cooperate with each other to create a hydrodynamic bearing that causes the impeller 708 to self-center within the pump housing 508 during rotation of the impeller 708.

Figure 12C:
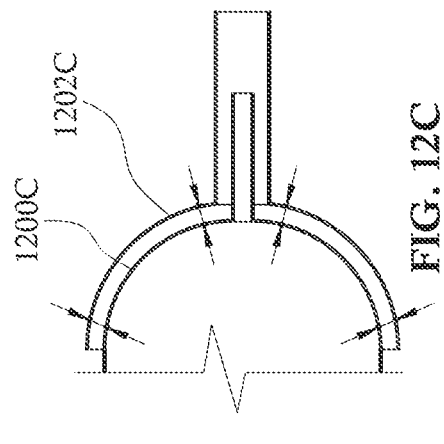
FIGS. 12A-12D illustrate interactions between pump impellers and pump housings having various shapes, in accordance with embodiments of the subject matter disclosed herein.
Figure 12D:
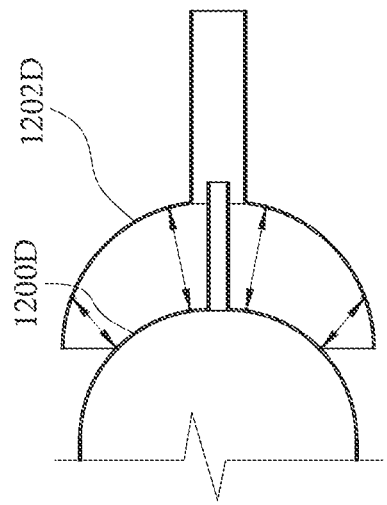
Figure 12A:
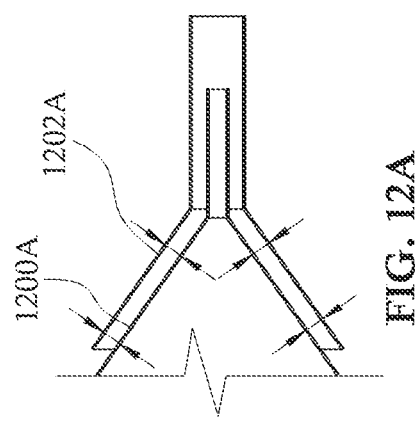
Figure 12B:
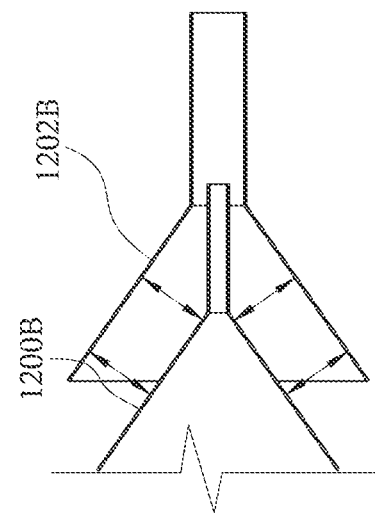

FIGS. 12A and 12B schematically illustrate certain interactions between impellers and pump housings having various shapes, in accordance with embodiments of the subject matter disclosed herein. FIGS. 12A and 12B more specifically illustrate the interaction between the components at two different alignment or spacing distances. In FIG. 12A, the impeller 1200A and pump housing 1202A are close together and the distance therebetween is uniform across their surface profiles. In FIG. 12B, the impeller 1200B and pump housing 1202B are farther apart. However, the distance between the impeller 1200B and pump housing 1202B is uniform across their surface profiles. This distance remains uniform because the angle of the impeller surface and pump housing surface is equal in both cases.

A uniform distance between the impeller and pump housing may facilitate efficient self-centering performance of the impeller within the pump housing, regardless of their relative longitudinal alignment or spacing distance. However, if the interfacing surfaces of the impeller and pump housing are curved, self-centering performance may benefit from more exact longitudinal spacing. For example, and as illustrated in FIG. 12C, the impeller 1200C and the pump housing 1202C are positioned longitudinally to permit a uniform distance therebetween, thereby providing consistent self-centering performance. In contrast, and as illustrated in FIG. 12D, the impeller 1200D and the pump housing 1202D are positioned farther from each other, thereby providing a non-uniform distance therebetween. Such a non-uniform distance may decrease the self-centering performance and detrimentally affect blood flow, fluid pumping efficiency, and component durability. As a result, it may be preferable to construct the impeller and pump housing with linear faced geometry (FIGS. 12A and 12B) instead of curved faces (FIGS. 12C and 12D).

FIGS. 13A and 13B schematically illustrate various impellers and pump housings that exhibit differing blood pumping blood flow characteristics, in accordance with embodiments of the subject matter disclosed herein. FIG. 13A illustrates an impeller 1300A that includes an expandable tapered body 1302A and a plurality of impeller ridges 1304A coupled to, and extending outwardly from, the tapered body 1302A. The tapered body 1302A includes: (i) a distal portion 1306A having a front surface 1308A, (ii) a maximum diameter portion 1310A having an intermediate surface 1312A, and (iii) a proximal portion 1314A having a back surface 1316A. The plurality of ridges 1304A extend radially outwardly from each of the front surface 1308A, the intermediate surface 1312A, and the back surface 1316A.

FIG. 13B illustrates a similar impeller 1300B including an expandable tapered body 1302B, although the plurality of impeller ridges 1304B extend radially outwardly from the front surface 1308B and the intermediate surface 1312B, but are absent from the back surface 1316B. The impeller 1300A, and the ridges 1304A thereof, may advantageously provide relatively high antegrade blood flow, as represented with arrows 1318A. Additionally, the impeller 1300A, and the ridges 1304A thereof, may advantageously provide relatively high retrograde flow, as represented with arrows 1320A. Such retrograde flow may be desirable and act as a lubricant between the drive shaft and drive shaft housing. The impeller 1300B, and the ridges 1304B thereof, may provide the similar benefits to antegrade flow 1318B while simultaneously reducing retrograde flow, as represented with smaller arrows 1320B. The absence of the ridges 1304B on the back surface 1316B may also provide a more uniform and linear surface on the back surface 1316B of the impeller 1300B, thereby providing the advantages described above in connection with the impellers 1200A, 1200B, and the pump housings 1202A, 1202B (FIGS. 12A and 12B).

As illustrated in FIGS. 13A and 13B, in some embodiments the impeller ridges 1304A, 1304B may extend parallel (non-helically) relative to the longitudinal/rotational axes 1322A, 1322B of the impellers 1300A, 1300B. Alternatively, and as illustrated elsewhere, the expandable impeller ridges 1304A, 1304B may extend helically relative to the longitudinal/rotational axes 1322A, 1322B of impellers 1300A, 1300B.

FIGS. 14A and 14B illustrate a possible flow path for the retrograde blood flow 1400 generated by the rotation of the impeller 708 within the pump housing 508, in accordance with embodiments of the subject matter disclosed herein. FIG. 14A displays the operational alignment and relative orientations between the impeller 708 and the pump housing 508. It should be noted that there are no bearings or bushings positioned between the impeller 708 and the pump housing 508, or between the impeller drive shaft 704 and the drive shaft housing 511.

With continued reference to FIG. 14B, in this configuration of the blood pump catheter system, the drive shaft housing 511 may include fenestrations, windows, or openings 3512 and the sheath 502 of the delivery sheath device 500 may also include fenestrations, windows, or openings 3294. When the delivery sheath device 500 is retracted, the sheath windows 3294 may at least partially align with the drive shaft housing 511 windows 3512. The alignment of these windows 3294/3512 may permit for blood to flow through the window openings of the sheath 502 and drive shaft housing 511 and to reach the drive shaft 704. This blood flow may provide a blood source for retrograde blood flow 1400 at the impeller 708 that may have multiple benefits. A couple non-limiting examples of the benefits of retrograde blood flow 1400 through the drive shaft housing 511 may include improving the functioning of the hydrodynamic bearing created between the impeller 708 and the pump housing 508, as well as acting like a lubricant between the drive shaft 704 and the drive shaft housing 511 to decrease the abrasion between the components. This hydrodynamic bearing created between the impeller 708 and the pump housing 508 can eliminate the need for a conventional mechanical bearing or bushing between the impeller 708 and the pump housing 508, and/or between the impeller drive shaft 704 and the drive shaft housing 511.

FIGS. 15A-15C illustrate an example blood pulling mechanical hemodynamic support device for use as part of the system 200 (e.g., FIG. 2), which comprises a blood pump with an internal motor disposed near the distal tip of the catheter system, in accordance with embodiments of the subject matter disclosed herein. The illustrated blood pulling pump device in its fully assembled state is illustrated in FIG. 15A. FIGS. 9A-9F (referred to above) describe the process of assembling this motorized blood pump configuration in-vivo.

FIG. 15B illustrates a close-up view of the expanded impeller 708 within the expanded pump housing 508, as well as the miniature motor 202 located proximally of the impeller 708. With such a pump system that includes a miniature motor 202, a few non-limiting considerations need to be adapted for the pump assembly process. The impeller 708 may be connected to a shortened length drive shaft 1504 that extends from the distal tip of the motor 202 through to the distal end of the impeller 708. This shortened drive shaft 1504 may be connected to the distal tip of the motor rotor 1500, thereby causing the drive shaft 1504 to rotate relative to the motor stator 1502 and the pump housing 508 when the motor 202 turns.

The motor 202 may have a hollow rotor 1500 thereby creating an internal channel or lumen 1512 within and along the central axis of the motor 202. This central lumen 1512, may allow for inflation of the impeller 708 through the motor 202 and drive shaft 1504. In order for the impeller 708 to maintain pressure when inflated, the distal end of the drive shaft 1504 and/or the proximal end of the hollow motor rotor 1500 may have an internal seal. A seal in the distal end of the drive shaft 1504 is illustrated in FIG. 15B as element 1508. FIGS. 15B and 15C illustrate a seal 1510 in the proximal end of the hollow motor rotor 1500. These seals may allow for the catheter system to be delivered over a guidewire into the correct anatomical position, and then may subsequently create a pressure tight seal once the guide wire is removed from the system, allowing the impeller 708 to maintain pressure.

Once the system is in the correct anatomical location, the inflation needle 1600 (e.g., FIGS. 9C-9E) may be advanced through the proximal seal 1510 thereby allowing for inflation of the impeller 708. Once the inflation needle 1600 is removed, the impeller 708 may maintain pressure due to the presence of the seals.

When the catheter system is ready to be removed from the patient, the inflation needle 1600 may again be inserted through the proximal seal 1510 and used to deflate the impeller 708. In some embodiments, the distal seal 1508 and the proximal seal 1510 may also function as pressure relief valves to prevent over inflation of the impeller 708

The miniature motor 202 may be connected to a controller external to the patient 206 (FIG. 2) through electrical wires 1506 which may be embedded within the walls of the catheter shaft.

Referring also to FIGS. 16A and 16B, additional views of the example inflation needle 1600, which may be used to inflate the impeller 708 through the miniature internal motor 202 are provided. The needle 1600 may include a sharp distal tip 1602, a surface bump 1604 and a hub 1606. The sharp distal tip 1602 may function to allow the distal tip portion of the inflation needle 1600 to pass through the proximal seal 1510 on the proximal end of the miniature motor 202 without damaging the sealing membrane or compromising the functionality of the seal 1510.

The surface bump 1604 may be an increase in diameter or a surface protrusion from the main body of the inflation needle 1600. This surface bump 1604 may function to prevent the inflation needle 1600 from being tracked too far through the hollow motor rotor 1500, thereby preventing the sharp distal tip 1602 of the inflation needle 1600 from damaging the impeller 708.

FIGS. 17A-17C illustrate an example sequence of steps to expand the impeller 708 and then couple the rotatable inner catheter 700 to an external motor 1700 which may for example be represented by the motor 104 (FIG. 1) in accordance with embodiments of the subject matter disclosed herein. The external motor 1700 includes a motor coupler 1702, a motor rotor 1704, and motor stator 1706.

The rotatable inner catheter 700 is shown with the impeller 708 in its radially contracted configuration in FIG. 17A. Then in FIGS. 17B and 17C, the impeller 708 has been expanded to its pumping profile by applying pressure through the hub 702 of the rotatable inner catheter 700.

The rotatable inner catheter 700, with its expanded impeller 708, may subsequently be connected to the motor 1700 using the motor coupler 1702. The motor coupler 1702 may be a connector that mechanically couples the motor rotor 1704 and the catheter hub 702.

Figure 18A:
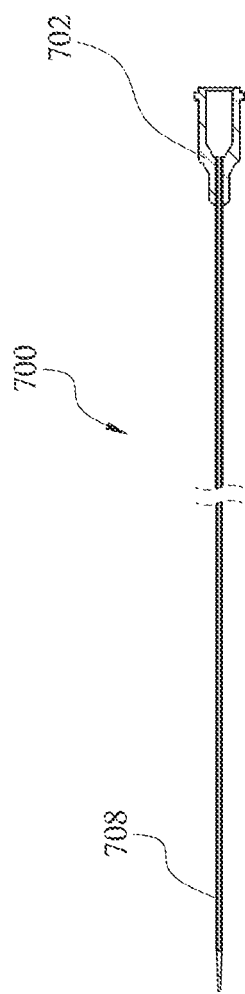
FIGS. 18A-18C illustrate steps for coupling an impeller drive shaft to a motor and expanding an example pump impeller, in accordance with embodiments of the subject matter disclosed herein.
Figure 18B:
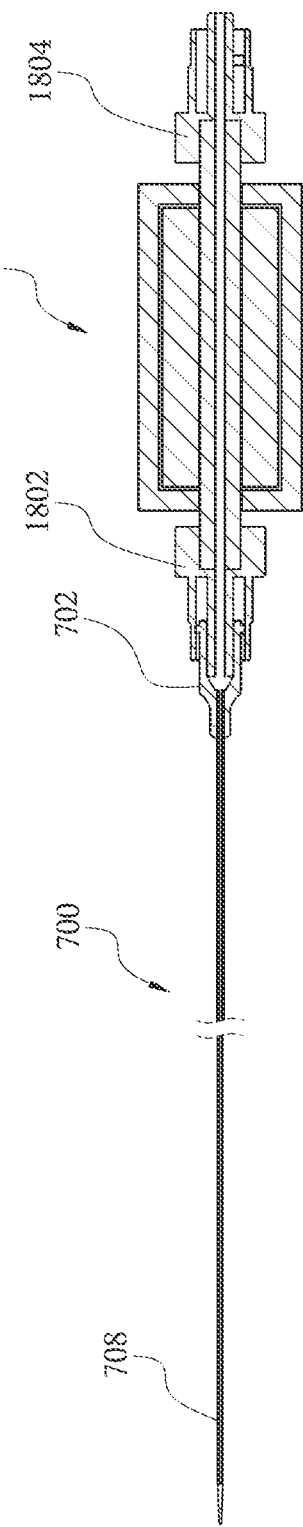
Figure 18C:
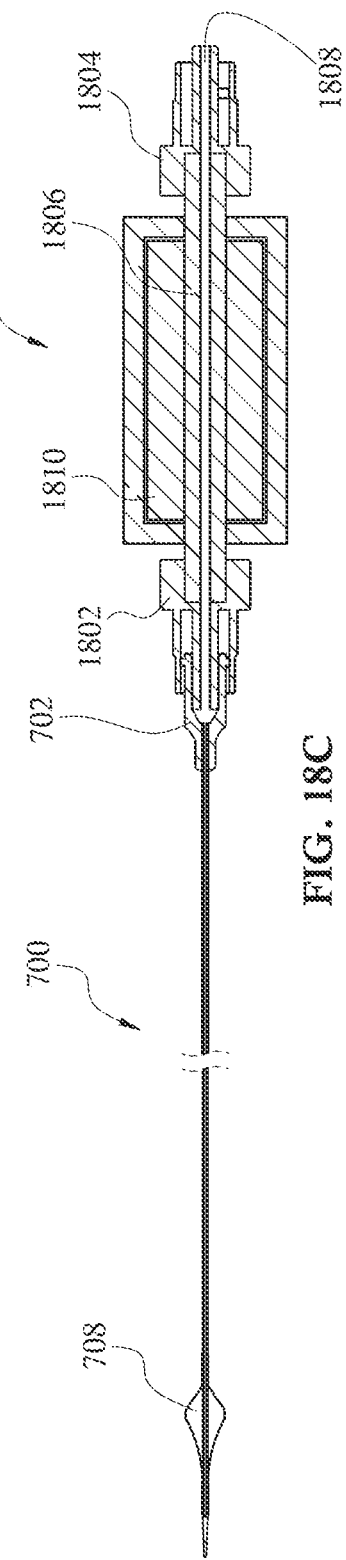

FIGS. 18A-18C illustrate a potential sequence of steps to couple the rotating inner catheter 700 to an external motor 1800, which may for example be represented by the motor 104 (FIG. 1), and subsequently expand the impeller 708 in accordance with embodiments of the subject matter disclosed herein. The rotatable inner catheter 700 is shown with the impeller 708 in its radially contracted configuration in FIG. 18A. Then as shown in FIG. 18B, the hub 702 of the rotatable inner catheter 700 may be coupled to the motor 1800 through a motor coupler 1802. Once the rotatable inner catheter 700 is coupled to the motor 1800, the impeller 708 may be expanded by applying pressure through an inflation port 1804 located proximally on a motor rotor 1806. The pressure may pass through the inflation path 1808 that may be located within a hollow motor rotor 1806, as shown in FIG. 18C.

With general reference to FIGS. 17A-17C and FIGS. 18A-18C, once the rotating inner catheter system 700 is coupled to the motor 1700/1800 and the impeller 708 is in its expanded state, the motor rotor 1704/1806 may be activated causing the motor rotor 1704/1806 to rotate while the motor stator 1706/1810 remains stationary. The rotating motor rotor 1704/1806 may impart rotational velocity to the rotatable inner catheter system 700 thereby causing the impeller 708 to rotate and create blood flow.

While FIGS. 18B and 18C illustrate a motor system 1800 with a hollow motor rotor 1806 to allow pressure to be applied through the motor, there are many other options for inflating the impeller 708 after the catheter is coupled to the motor without the inflation path 1808 passing through the motor rotor. To illustrate a non-limiting example, the hub 702 may be attached to a geared system and be offset from the motor 1800, thereby allowing the inflation path to traverse through the center of a gear instead of through the motor (not shown).

FIGS. 19A and 19B illustrate an example configuration of the inlet cannula 504 and the pump housing 508 located at the distal end portion of the housing component 510 in their expanded state in accordance with embodiments of the subject matter disclosed herein.

During use, the AV leaflets may press on the outside surfaces of the inlet cannula 504, compressing it radially as the inlet cannula 504 sits across the AV. Therefore, the inlet cannula 504 may require sufficient radial strength, also known as hoop strength, to maintain its expanded diameter as it sits across the AV. The tendency of the inlet cannula 504 to maintain the desired expanded profile helps to ensure proper pumping performance and desired blood flow during use. Similarly, the pump housing 508 houses the pump impeller 708 (shown elsewhere) and may require a precise expanded profile to ensure proper pumping performance and desired blood flow in cooperation with the impeller 708.

In the depicted embodiment, the inlet cannula 504 is composed of a flexible wall 536 with an expandable braid support structure 1900 coupled to or within the flexible wall 536. The expandable braid support structure 1900 is constructed of one or more elongate elements 1902 that is/are braided or woven into a tubular construct. This same braid support structure 1900 extends continuously through to the pump housing 508 and supports the flexible wall 524 of the pump housing 508. The braid support structure 1900 may be disposed internally to the flexible walls 536/524, it may be embedded within the flexible walls 536/524, it may be disposed externally to the flexible walls 536/524, or any combination thereof.

When employing the expandable braid support structure 1900 as a support structure for the flexible walls 536/524, the inlet cannula 504 and pump housing 508 may extend longitudinally when in a collapsed and radially constricted configuration, and then contract longitudinally when self-expanding to their fully expanded operational profile. This braid support structure 1900 may provide sufficient radial strength in the inlet cannula 504 to resist compression from the AV.

FIGS. 20A and 20B illustrate another example configuration of the inlet cannula 504 and the pump housing 508 located at the distal end portion of the housing component 510 in their expanded state, in accordance with embodiments of the subject matter disclosed herein. The inlet cannula 504 may be composed of the flexible wall 536 with an expandable coil support structure 2000 coupled to the flexible wall 536.

The expandable coil support structure 2000 may be composed of a single filar coil 2002 or of multiple separate filars 2002. In some embodiments, the coil support structure 2000 may extend between the distal marker 530 and the proximal marker 528 and terminate distally of the pump housing 508. The coil support structure 2000 may be disposed internally to the flexible wall 536, it may be embedded within the flexible wall 536, it may be disposed externally to the flexible wall 536, or any combination thereof. The coil support structure 2000 may provide sufficient radial strength in the inlet cannula 504 to resist compression from the AV.

In the depicted embodiment, the pump housing 508 may not include any support structures within its flexible wall 524. The pump housing 508 may be expanded by the pumping action of the impeller 708 (shown elsewhere). When the impeller 708 rotates creating blood flow, the pressure within the pump housing 508 may increase in relation to the pressure external to the pump housing 508. This increased internal pressure may expand the pump housing 508 to its optimal pumping configuration or profile.

Figures 21A, 21B:
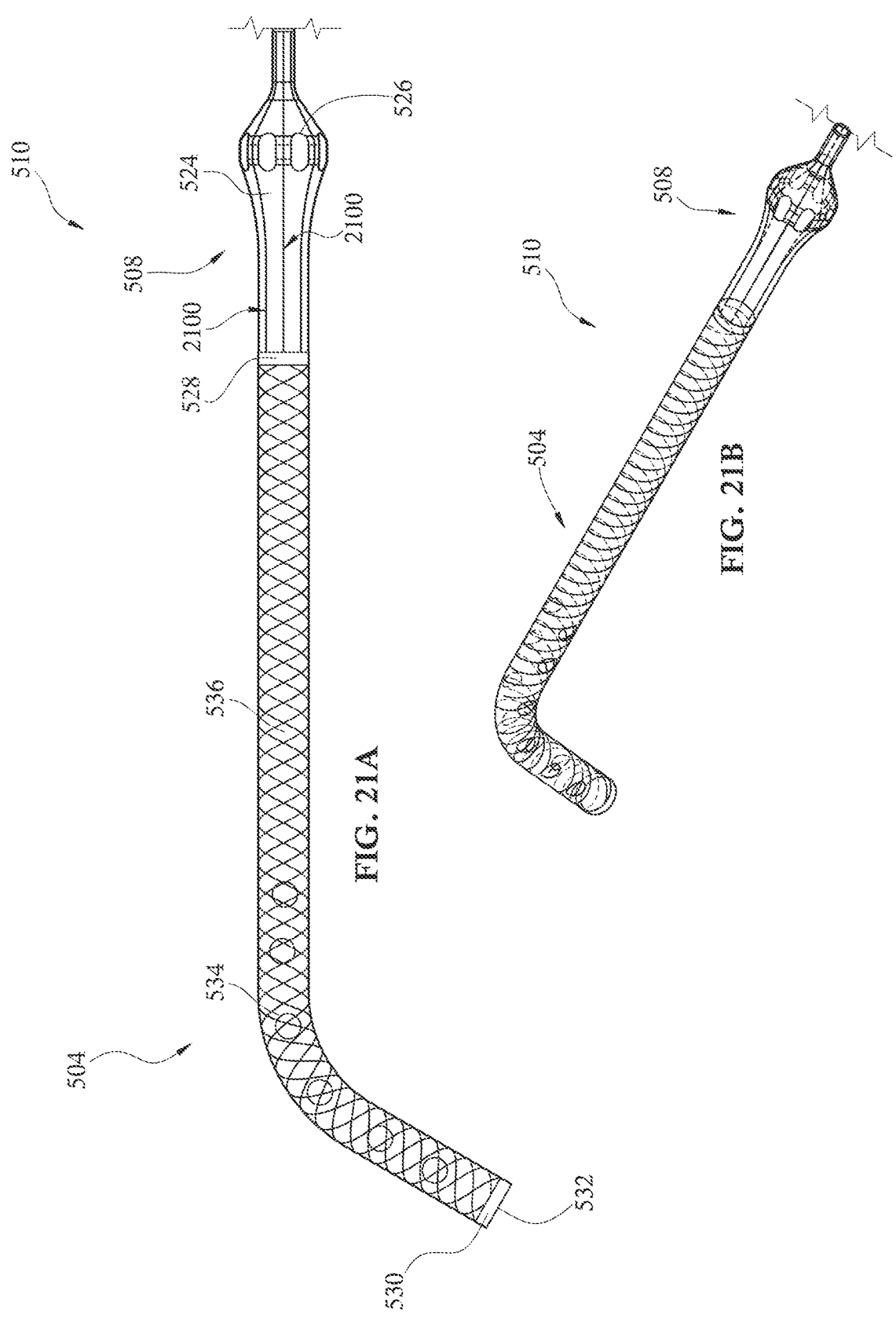
FIGS. 21A-21B illustrate an example coil supported inlet cannula and a longitudinally supported pump housing, in accordance with embodiments of the subject matter disclosed herein.

FIGS. 21A and 21B illustrate another possible configuration of the inlet cannula 504 and the pump housing 508 in their expanded state, in accordance with embodiments of the subject matter disclosed herein. The pump housing 508 may be reinforced with a longitudinal support structure 2100 to provide additional column strength. This longitudinal support structure 2100 may be within, embedded, or externally coupled to the flexible wall 524. The additional column strength may aid in device delivery, operation and positional adjustments, and retrieval. In some embodiments, the same elongate elements of the longitudinal support structure 2100 in the region of the pump housing 508 extend into the region of the inlet cannula 504 and are braided or woven as shown. Alternatively, in some embodiments the elongate elements of the longitudinal support structure 2100 in the region of the pump housing 508 are separate from the elongate elements in the region of the inlet cannula 504. In other embodiments, the elongate elements of the longitudinal support structure 2100 in the region of the pump housing 508 are separate from, but attached to, the elongate elements in the region of the inlet cannula 504.

Figure 22A:
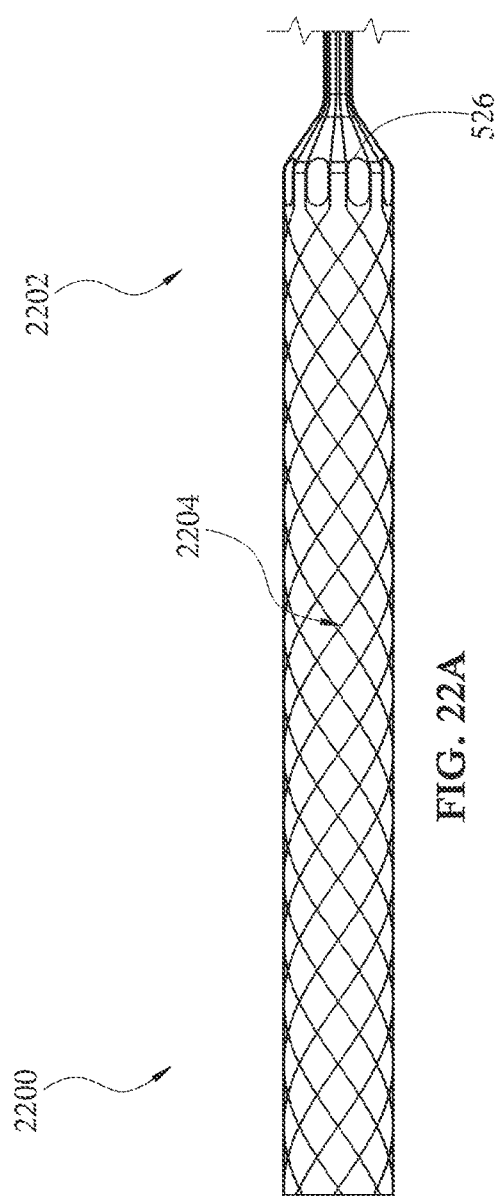
FIG. 22A illustrates an example braid supported inlet cannula and pump housing with a constant diameter, in accordance with embodiments of the subject matter disclosed herein.

FIG. 22A illustrates another example configuration of an inlet cannula 2200 and a pump housing 2202 in their expanded state, in accordance with embodiments of the subject matter disclosed herein. The inlet cannula 2200 and the pump housing 2202 can be located at the distal end portion of some embodiments of the housing component 510. As shown, a possible configuration of the inlet cannula 2200 and the pump housing 2202 is for the diameter of the inlet cannula 2200 and the diameter of the pump housing 2202 to be the same diameter. In other configurations described herein, the inlet cannula 504 and the pump housing 508 (shown elsewhere) are different diameters, with the pump housing 508 having a larger diameter and the inlet cannula 504 having a smaller diameter to allow for easier accommodation within the AV. However, if the patient is large enough, and if the anatomy of the AV can accommodate a larger inlet cannula 2200, then having a larger internal diameter of the inlet cannula 2200 may reduce the pressure gradients within the inlet cannula 2200 and improve blood flow dynamics. In the configuration depicted in FIG. 22A, the flexible walls of the inlet cannula 2200 and the pump housing 2202 are supported by a continuous diameter expanding braid structure 2204.

Figure 22B:
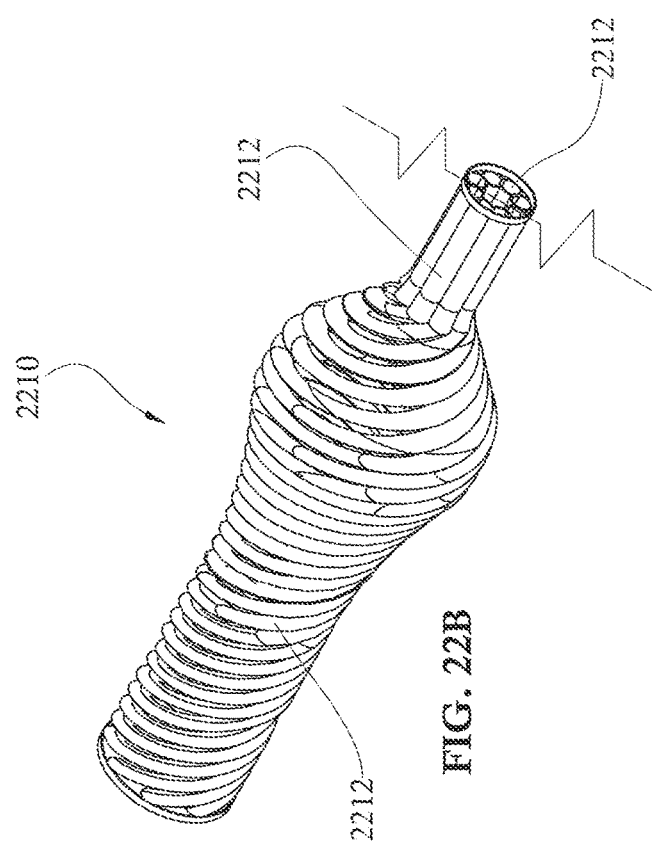
FIG. 22B illustrates an example balloon based inlet cannula and pump housing, in accordance with embodiments of the subject matter disclosed herein.

Additionally, as shown in FIG. 22B, in some embodiments the inlet cannula and pump housing 2210 may be composed of a helical balloon 2212 in a coiled stack configuration. The helical balloon pump housing 2210 may be a single helical stacked balloon (not shown) or comprised of a plurality of coiled balloons 2212 as shown in FIG. 22B. This structure may be folded down during delivery and subsequently expanded through the use of pressure to maintain a rigid shape.

With general reference to FIGS. 19A-22B, in accordance with embodiments of the subject matter disclosed herein, the support structures used to reinforce the inlet cannula and pump housing can be comprised of multiple different materials, components, or a combination thereof. The braids and coils may be composed of (but not limited to) a metallic structure, like super-elastic Nitinol for example. They may also be composed of a polymer material, like an Aramid or a Nylon. The coil structures may also be composed of long tubular balloon structures that would allow them to be inflated to expand the inlet cannula and pump housing.

FIGS. 23A and 23B illustrate another example mechanical hemodynamic support device 2300 (or "pump device 2300") in an expanded configuration across the aortic valve AV. The pump device 2300 includes a skirt 2302 attached at the junction between the pump housing 2304 and the inlet cannula 2306, in accordance with embodiments of the subject matter disclosed herein.

The skirt 2302 may be self-expanding once unsheathed (e.g., from the delivery sheath device 500 described above) via a self-expanding support structure 2308. The self-expanding support structure 2308 can be constructed from super elastic Nitinol wire, for example. After the skirt 2302 is expanded, it may rest against the aortic valve AV and thereby prevent the device 2300 from migrating excessively distally to within the left ventricle. The skirt 2302 may also assist in stabilizing the deployed device within the patient's anatomy. Additionally, the skirt 2302 may reduce aortic insufficiency by obstructing blood regurgitation through the aortic valve and increasing pressure against the aortic valve AV, thereby permitting the valve to sufficiently, or fully, close during diastole.

FIGS. 24A and 24B illustrate another example mechanical hemodynamic support device 2400 (or "pump device 2400") in an expanded configuration across the aortic valve AV. The pump device 2400 includes petals 2402 attached at the junction between the pump housing 2404 and the inlet cannula 2406, in accordance with embodiments of the subject matter disclosed herein.

The petals 2402 may be self-expanding once unsheathed (e.g., from the delivery sheath device 500 described above) via a self-expanding support structure 2408. The self-expanding support structure 2408 can be constructed from super elastic Nitinol wire, for example. After the petals 2402 are expanded, they may rest against the aortic valve AV and thereby prevent the device 2400 from migrating excessively distally to within the left ventricle. The petals 2402 may also assist in stabilizing the deployed device within the patient's anatomy. Additionally, the petals 2402 may reduce aortic insufficiency by obstructing blood regurgitation through the aortic valve AV and increasing pressure against the aortic valve AV, thereby permitting the valve to sufficiently, or fully, close during diastole. Having petals 2402 resting against the AV as opposed to a skirt 2302 may be less obstructive to the native continued blood flow provided by the patient's heart.

Figure 25:
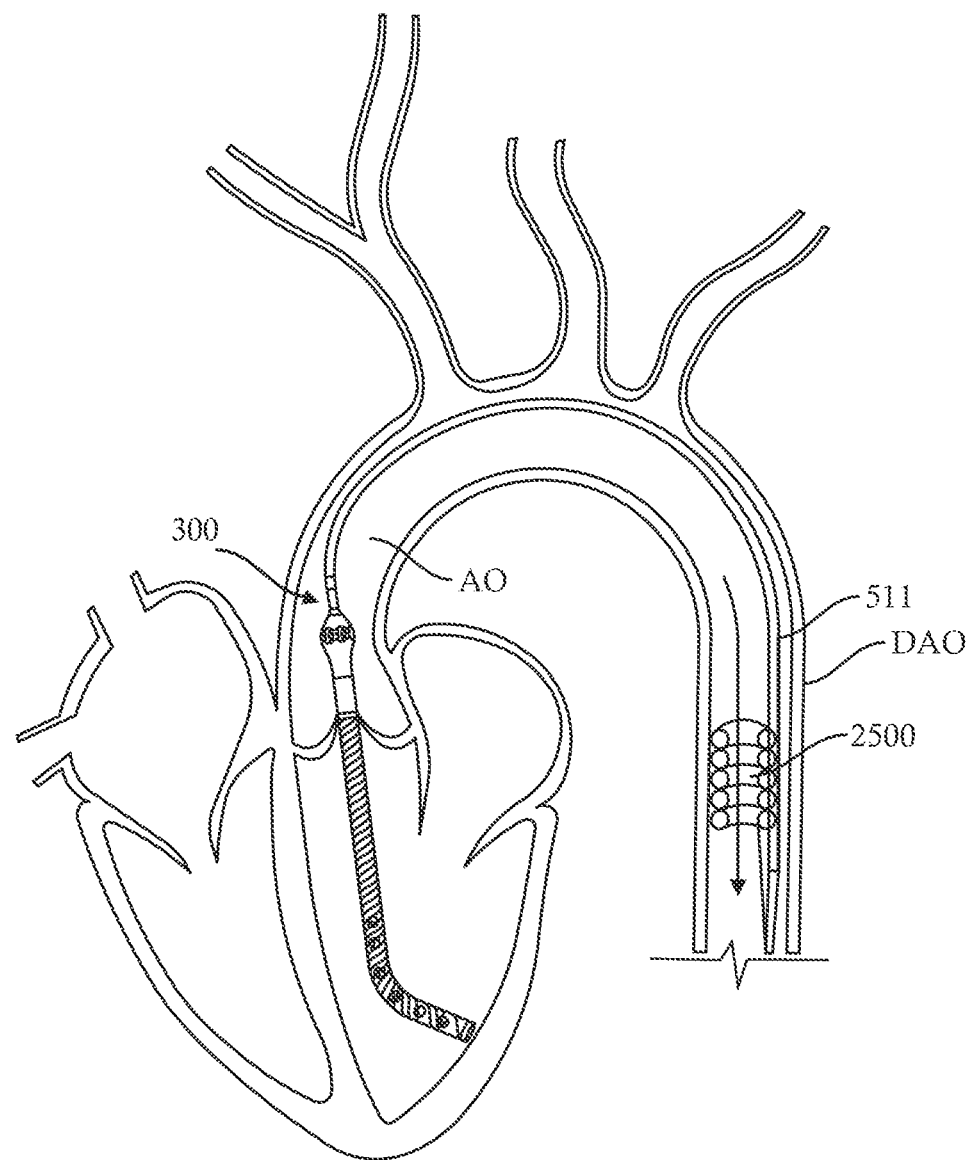
FIG. 25 illustrates an example method for securing the mechanical hemodynamic support device of FIG. 3 within a patient's anatomy, in accordance with embodiments of the subject matter disclosed herein.

FIG. 25 illustrates an example system and method for securing or anchoring the pump device 300 within a patient's anatomy, in accordance with embodiments of the subject matter disclosed herein. The method includes deploying a balloon 2500 in the aorta AO or the arteries that originate from the aortic arch, such as the descending aorta DAO. The balloon 2500 may be a separate device or a balloon that is attached to the drive shaft housing 511 and tracked through the anatomy simultaneously with the main pumping device 300.

When the balloon 2500 is inflated, it creates apposition against the vessel wall thereby securing the balloon 2500 within the anatomy. If the balloon 2500 is attached to the drive shaft housing 511, then when the balloon 2500 is secured within the anatomy, the pump device 300 is secured within the anatomy. If the balloon 2500 is a separate device, when the balloon 2500 is inflated and secured within the anatomy, it may press and pin the drive shaft housing 511 against the vessel wall, thereby securing the pump device 300 within the anatomy.

In some embodiments, the balloon 2500 in its expanded state may have a spiral configuration that defines an open central passageway that permits blood perfusion through the balloon 2500 as illustrated. The balloon 2500 may be constructed of a semi-compliant material, permitting the balloon 2500 to conform to the patient's vessel anatomy, thereby allowing it to be more versatile in terms of deployment locations.

Figure 26:
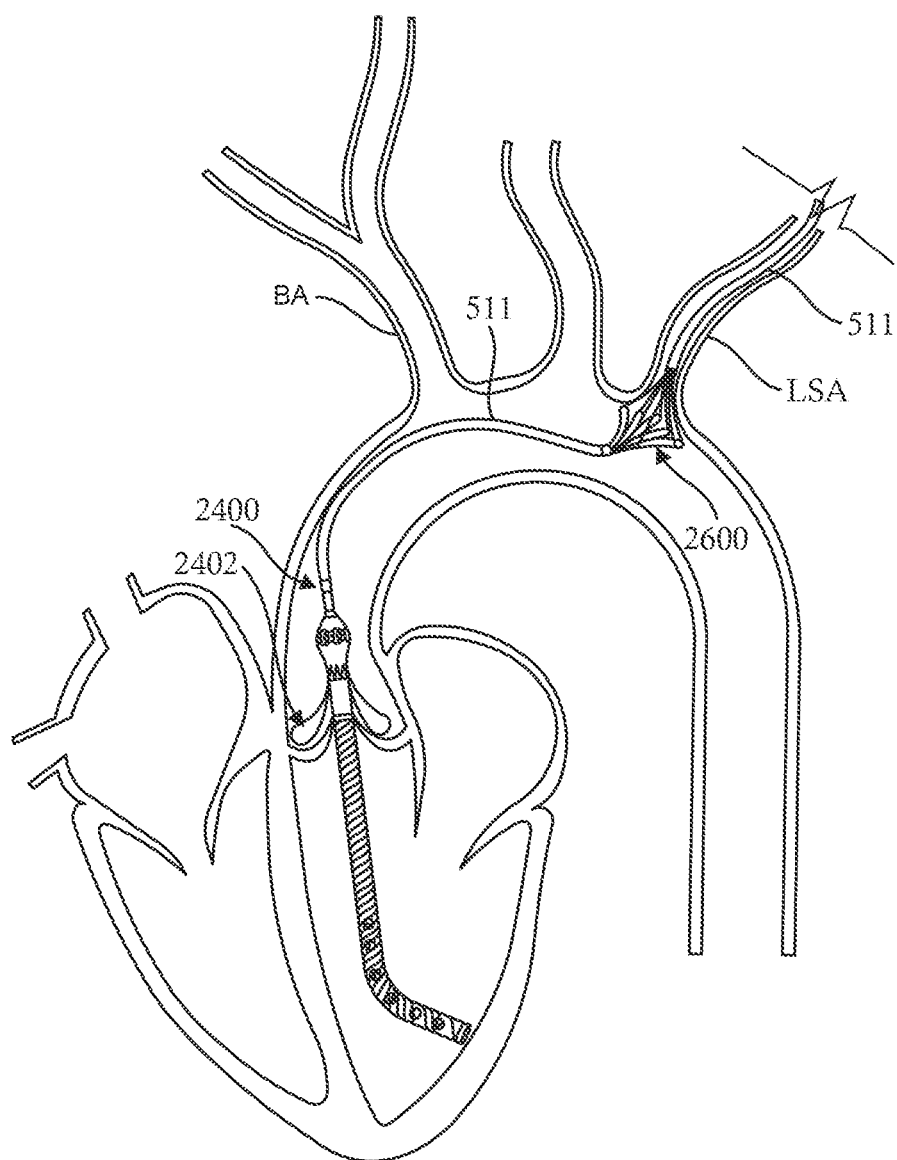
FIG. 26 illustrates another example method and apparatus for securing the mechanical hemodynamic support device of FIG. 3 within a patient's anatomy, in accordance with embodiments of the subject matter disclosed herein.

FIG. 26 illustrates another example system and method for securing the pump device 2400 (FIGS. 24A and 24B) within a patient's anatomy, in accordance with embodiments of the subject matter disclosed herein. The petals 2402 may prevent the pump device 2400 from migrating distally within the patient's anatomy once deployed. However, the variable thrust generated by the pumping action of the pump device 2400 may cause the pump device 2400 to migrate proximally away from the desired positioning within the anatomy. The overall device thrust will vary based upon the flow rate. As a result, it may be beneficial to add an additional component or mechanism to inhibit the device 2400 from migrating proximally within the anatomy after deployment.

An example of an additional anti-migration mechanism is an expandable ostial shaft anchor 2600 shown in FIG. 26. In some embodiments, the anchor 2600 may self-expand when unsheathed after navigating through the brachiocephalic artery BA or the left subclavian artery LSA, as illustrated. The anchor 2600 may expand to a diameter greater than that of the artery. As a result, the expanded anchor 2600 cannot migrate proximally through the artery, thereby preventing proximal movement of the device 2400 within the patient.

In some embodiments, the ostial shaft anchor 2600 may be constructed with an open-celled stent-like expandable structure (that is, not covered by a membrane), thereby permitting perfusion through the artery. The ostial shaft anchor 2600 may be in a fixed position along the drive shaft housing 511, or it may be movable along the drive shaft housing 511 and securable onto the drive shaft housing 511 after expansion. The ostial shaft anchor 2600 may be re-collapsible (e.g., into the delivery sheath device 500) to facilitate subsequent removal from the anatomy.

Figure 27:
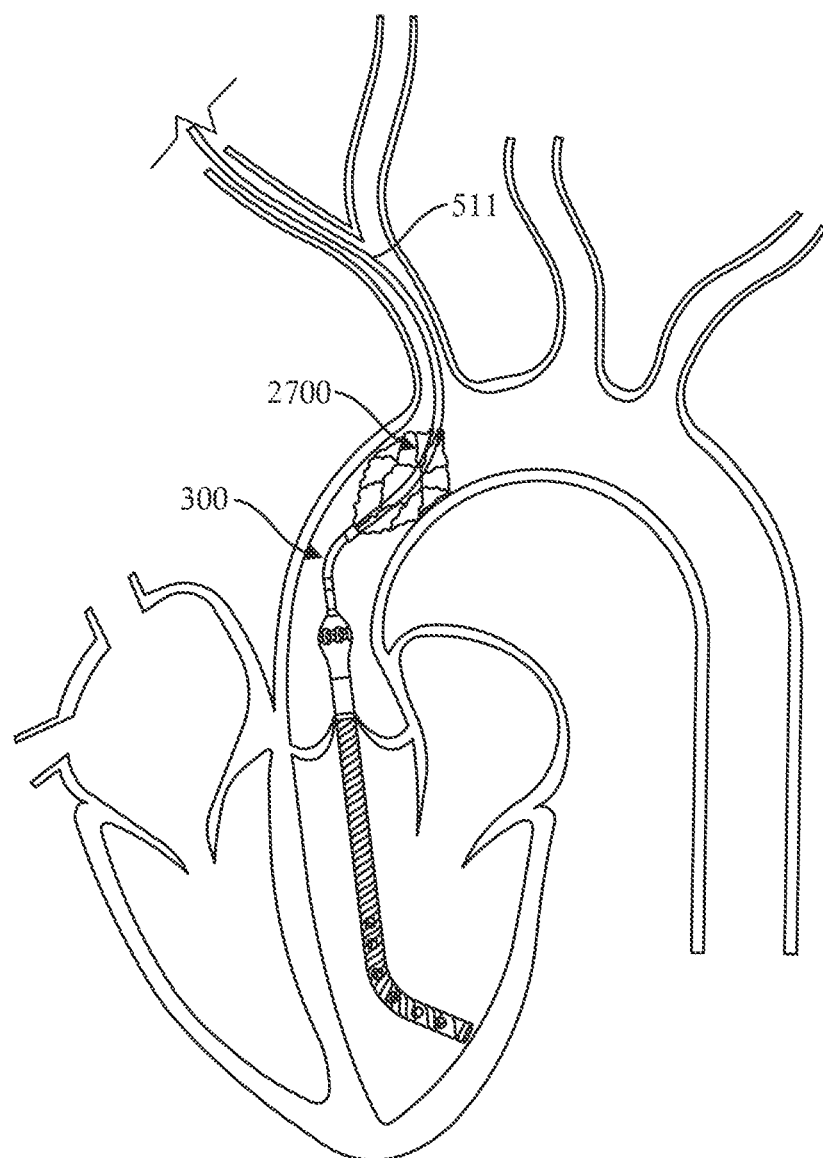
FIG. 27 illustrates another example method and apparatus for securing the mechanical hemodynamic support device of FIG. 3 within a patient's anatomy, in accordance with embodiments of the subject matter disclosed herein.

FIG. 27 illustrates yet another example system and method for securing the pump device 300 within a patient's anatomy, in accordance with embodiments of the subject matter disclosed herein. In this embodiment, an expandable cage anchor 2700 is coupled to the drive shaft housing 511. Upon self-expansion when expressed from the delivery sheath device 500, the cage anchor 2700 creates appositional forces against the vessel walls and thereby secures the drive shaft housing 511 within the anatomy. The expandable cage anchor 2700 may permit blood perfusion through the aorta and adjacent vessels.

Although not specifically illustrated, mechanical hemodynamic support devices in accordance with embodiments of the subject matter disclosed herein may include any combination of the anchoring mechanisms illustrated in FIGS. 23, 24, 25, 26, and 27.

FIGS. 28A-28F illustrate various possible configurations of the pump housing 508 and its exit ports, in accordance with embodiments of the subject matter disclosed herein. The proximal portion of the pump housing 508 includes the exit ports (e.g., exit ports 526) where the high-pressure blood exits the pump housing 508 and enters the AO. The exit ports 526 act like nozzles when there is a large pressure gradient across them. Therefore, it may be desirable to make modifications to the standard exit ports 526 to reduce the abruptness of the pressure gradient and reduce the stresses (e.g., shear stresses) on the blood.

FIGS. 28A, 28B, and 28C show the exit ports 526 with example exit port relief cutouts 2802. The exit port relief cutouts 2802 are cut out of the flexible wall 524 of the pump housing 508. These exit port relief cutouts 2802 may be positioned around the periphery of the exit ports 526 to create exit port flaps 2804 between adjacent cutouts 2802 that may bend or flex outward when the pump housing 508 is pressurized. The exit port flaps 2804 may act as a ramp or smooth transition and funnel the blood that is flowing out of the pump housing 508 more gradually and with less stress, thereby improving the flow dynamics.

FIGS. 28D, 28E, and 28F take the concept of exit port relief cutouts 2802 further. In this configuration, the example exit ports 2810 are mostly comprised of the relief cutouts 2812 instead of a larger hole cut in the flexible wall 524 of the pump housing 508 (e.g., as shown in FIGS. 28A-28C). The hole in the center of the exit ports 2810 may even be decreased down to being non-existent. The relieve cutouts 2812 are much larger (e.g., longer) and may be large enough to converge with each other. This leads to the exit port flaps 2814 being much larger. The advantage of this configuration of exit ports 2810 is that the exit ports 2810 may now act as a one-way valve allowing blood to flow out of the pump housing 508 when the impeller 708 (shown elsewhere) is rotating and the pressure inside the pump housing 508 is higher than in the AO. Conversely, when the pump is not running, the larger exit port flaps 2814 may converge with each other, thereby closing the exit ports and preventing blood back flow from the AO, through the pump housing 508 and into the LV via the inlet cannula.

FIGS. 29A-29C illustrate cross sectional views of the pump housing exit ports 526, in accordance with embodiments of the subject matter disclosed herein. FIG. 29A illustrates the pump housing 508A and its exit ports 526A configured axially in a ring around the perimeter of the pump housing's 508A flexible wall 524, thereby having a 90 degree angle in relation to a tangent line 2904A from the center axis 2902A of the pump housing 508A. FIG. 29B illustrates how a pump housing 508B and its exit ports 526B may be configured at any degree of angle between 0 and 90 degrees (shown at 68 degrees for example) to the axis of revolution 2902B. FIG. 29C illustrates a pump housing 508C with its exit ports 526C configured in a plane tangent to the center axis 2902C of the pump housing 508C and perpendicular to the flexible wall 524 of the pump housing 508C resulting in a 0 degree angle in relation to a tangent line 2904C from the center axis 2902C of the pump housing 508C. FIGS. 29A-29C each illustrate the blood flow 2900A, 2900B, and 2900C, through the different exit port angles. Adjusting the exit port angles may improve the laminar flow dynamics of the blood as it passes through the exit ports, thereby decreasing hemolysis.

FIG. 30 illustrates another view of the delivery sheath device 500. The delivery sheath device 500 includes the handle 512, the sheath 502, the radiopaque distal marker band 514 (optional), and the atraumatic bumper tip 506 (optional). The handle 512 is located at the proximal end of the delivery sheath device 500 and remains external to the patient. The sheath 502 extends distally from the handle 512. The radiopaque distal marker band 514 can be located anywhere on the sheath 502 such as at a distal tip portion of the sheath 502. In some embodiments, multiple radiopaque distal marker bands 514 can be located along the sheath 502. The atraumatic bumper tip 506 may be located at the distal tip of the sheath 502.

The sheath 502 can be made of a thin and flexible, yet non-compliant (low stretching/yielding), membrane. In some embodiments, the sheath 502 can be purely polymer based. In some embodiments, the sheath 502 can be polymer based and can include structural reinforcements in the form of metal or polymer members to increase parameters such as kink resistance and/or column strength.

As described above, the sheath 502 defines a lumen in which the housing component (e.g., the housing component 510) can be slidably contained in a radially compressed low-profile delivery configuration. After advancing the sheath 502 containing the housing component to a target location within a patient, the heart for example, the delivery sheath device 500 can then be retracted proximally (while maintaining the position of the housing component) to express the distal end portion of the housing component from containment within the sheath 502. In some cases, when it is desired to reposition the pump device or to remove the pump device, the delivery sheath device 500 can be advanced distally to recapture the housing component within the sheath 502.

FIGS. 31A-31C illustrate that, in some embodiments, the delivery sheath device 500 can be configured as a tear-away sheath or a split-able sheath. In such a case, the delivery sheath device 500 can be advantageously removed from the patient after its function of advancing and deploying the housing component has been performed. Removing the delivery sheath device 500 in such a manner can be advantageous because the size of the percutaneous opening of the patient can be slightly reduced after the removal of the delivery sheath device 500.

In FIG. 31A, the sheath 502 includes two sets of linearly arranged indentations or perforations 3182. In FIG. 31B, the sheath includes two linearly arranged grooves 3186. FIG. 31C shows that, in some embodiments the perforations 3182 or the grooves 3186 are arranged about 180° opposite of each other. In each case, the perforations 3182 or the grooves 3186 configure the sheath 502 with weakened regions that make the sheath 502 manually breakable or split-able. The handle 512 can also be made of two separate portions or be made to be split-able into two portions.

FIG. 32 shows another optional feature that can be included as part of some embodiments of the delivery sheath device 500. That is, as shown in the depicted embodiment, the sheath 502 can define one or more fenestrations, windows, or openings 3294. In the depicted non-limiting example, the openings 3294 are longitudinally elongated openings 3294. Any suitable sizes and shapes of the openings 3294 can be implemented for the delivery sheath device 500. The openings 3294 are not located on the proximal portions of the sheath 502 that are likely to be positioned external of the patient's body when in use.

As described further herein, in some embodiments the openings 3294 can permit blood to flow laterally into the sheath 502 and then into a housing component (e.g., the housing component 510) that also includes openings in its drive shaft housing (e.g., the drive shaft housing 511). Such blood flowing into the housing component can advantageously provide lubrication and cooling, because heat may be generated from the friction between the rotating impeller drive shaft and the stationary drive shaft housing.

Moreover, and also in reference to FIGS. 14A and 14B, in some embodiments the blood flow into the drive shaft housing that is permitted through the openings 3294 of the sheath 502 and then through openings in the drive shaft housing advantageously facilitate the hydrodynamic bearing functionality described in reference to FIGS. 11-13B.

Further, in some cases the openings 3294 can advantageously allow for air to be vented out of the sheath 502 and/or the drive shaft housing prior to and during insertion into a patient.

FIGS. 33A and 33B show another optional feature that can be included as part of some embodiments of the delivery sheath device 500. In the depicted embodiment, the proximal portion of the sheath 502 includes a cutout proximal portion 3302. The cutout proximal portion 3302 is located along the proximal portion of the sheath 502 where the sheath 502, when in use, passes through the skin and subcutaneous puncture at the vasculature access site. Accordingly, the size of the skin and subcutaneous puncture can be reduced in some cases, as compared to sheaths 502 that do not include the cutout proximal portion 3302. In some embodiments, one or more longitudinally extending stiffening rods 3390 can be included, as shown, to provide structural reinforcement to the cutout proximal portion 3302 of the sheath 502.

FIGS. 34A-34C illustrate optional features that can be included as part of some embodiments of the housing component 510. In the depicted embodiment, the housing component 510 includes a drive shaft housing hub 518, a drive shaft housing 511, a pump housing (not shown; refer to pump housing 508 in FIG. 6, for example), and an inlet cannula (not shown; refer to inlet cannula 504 in FIG. 6, for example).

The drive shaft housing hub 518 is located at a proximal end portion of the housing component 510. A drive shaft hub seal 3404 configured to slidably receive, and seal against, an impeller drive shaft (e.g., the drive shaft 704) is located in the drive shaft housing hub 518. The drive shaft housing 511 distally extends from the drive shaft housing hub 518. The drive shaft housing 511 defines a lumen configured to receive an impeller drive shaft (e.g., the drive shaft 704). The pump housing (not shown) is attached to and extends distally from a distal end portion of the drive shaft housing 511. The inlet cannula (not shown) is attached to and extends distally from the pump housing.

In the depicted embodiment, the inner diameter of the drive shaft housing 511 includes an annular protrusion 3408. The annular protrusion 3408 creates a region at which the inner diameter of the lumen of the drive shaft housing 511 is constricted to a smaller open diameter as compared to other portions of the drive shaft housing 511.

As shown in FIG. 34C, the annular protrusion 3408 can interface with an annular projection 3468 on the impeller drive shaft (e.g., the impeller drive shaft 704). The outer diameter of the annular projection 3468 can be larger than the inner diameter of the annular protrusion 3408. Accordingly, the dimensional interference between the annular protrusion 3408 the annular projection 3468 can serve to locate the distal-most longitudinal position of the impeller drive shaft relative to the housing component 510. This longitudinal locational registration can ensure that the pump impeller (e.g., the pump impeller 708 and other pump impellers described herein) is located properly within the pump housing (e.g., the pump housing 508).

Figure 35:
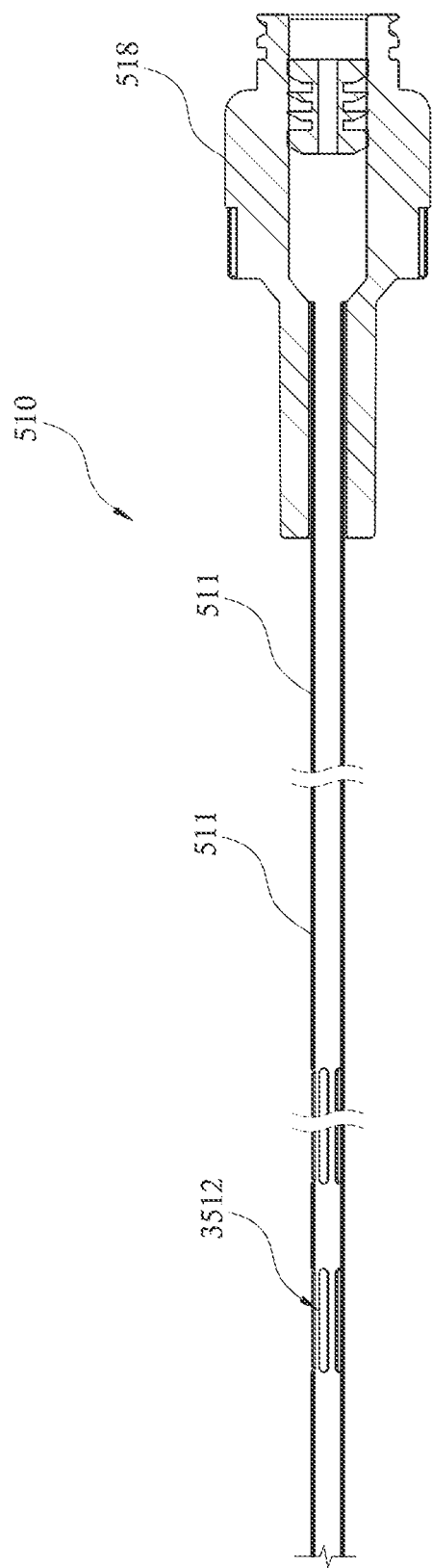
FIG. 35 illustrates an example housing component with blood perfusion holes, in accordance with embodiments of the subject matter disclosed herein.

FIG. 35 illustrates additional optional features that can be included as part of some embodiments of the housing component 510. In the depicted embodiment, the drive shaft housing 511 of the housing component 510 defines one or more fenestrations, windows, or openings 3512. In the depicted non-limiting example, the openings 3512 are longitudinally elongated openings 3512. Any suitable sizes and shapes of the openings 3512 can be implemented for the drive shaft housing 511.

The openings 3512 can at least partially align with, or otherwise cooperate with, the openings 3294 (FIG. 32) defined by the sheath 502 so that blood can flow through the sheath 502 and into the drive shaft housing 511. Such blood flow into the drive shaft housing 511 can: (i) provide lubrication and cooling to mitigate the heat generated from the friction between the rotating impeller drive shaft and the stationary drive shaft housing 511 as well as (ii) facilitate the hydrodynamic bearing functionality described in reference to FIGS. 11-13B.

Figure 36:
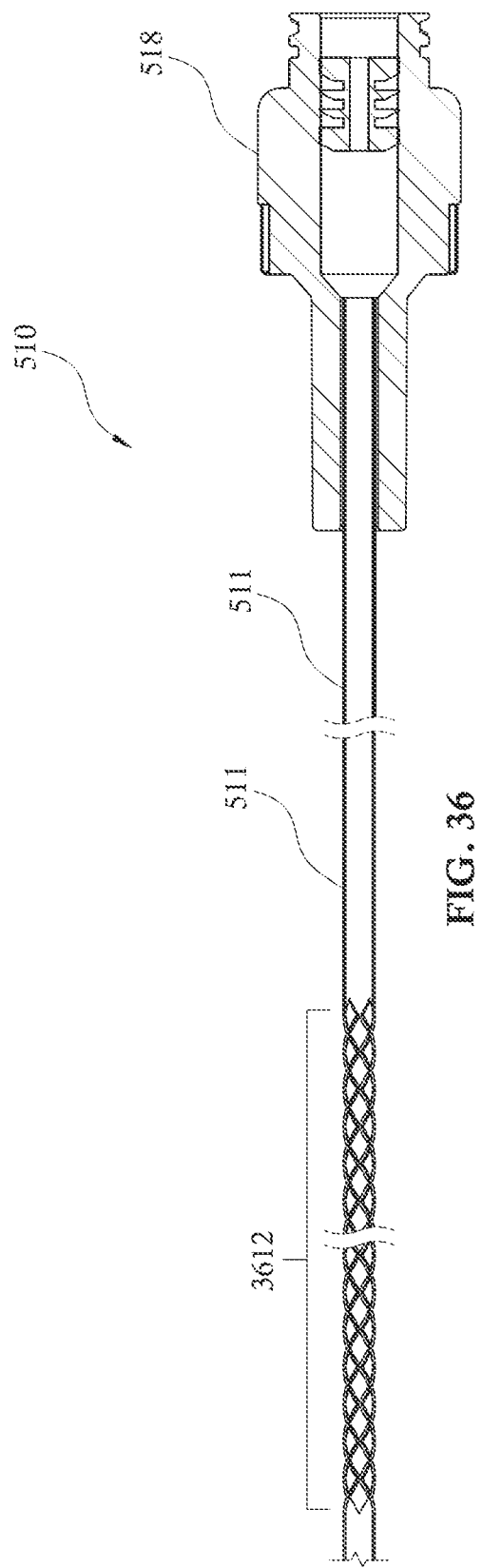
FIG. 36 illustrates an example housing component with an open-celled matrix, in accordance with embodiments of the subject matter disclosed herein.

FIG. 36 illustrates additional optional features that can be included as part of some embodiments of the housing component 510. In the depicted embodiment, the drive shaft housing 511 of the housing component 510 includes one or more open-celled portions 3612. The one or more open-celled portions 3612 may be a stent-like construct. That is, the one or more open-celled portions 3612 can be either braided, woven, or laser cut and expanded, for example. The one or more open-celled portions 3612 have multiple open areas that (in combination with openings 3294 in the sheath 502 of the delivery sheath device 500 as shown in FIG. 32, or in combination with a tear-away sheath device 500 as shown in FIGS. 31A-31C) allow lateral blood flow into the drive shaft housing 511 for lubrication, cooling, and hydrodynamic bearing benefits as described above. While the open-celled portions 3612 may allow for lateral blood flow, they may still shield the rotating drive shaft (e.g., the drive shaft 704) from damaging the patient's anatomy or entangling with separate devices being employed by the clinician.

Figure 37A:
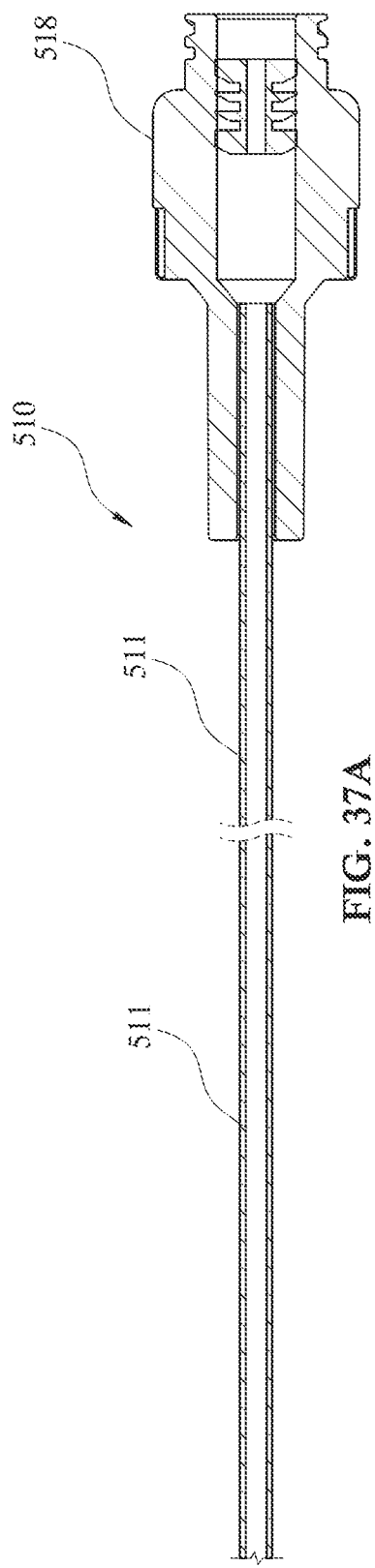
FIGS. 37A-37B illustrate an example housing component with lumens for electrical connections, in accordance with embodiments of the subject matter disclosed herein.
Figure 37B:
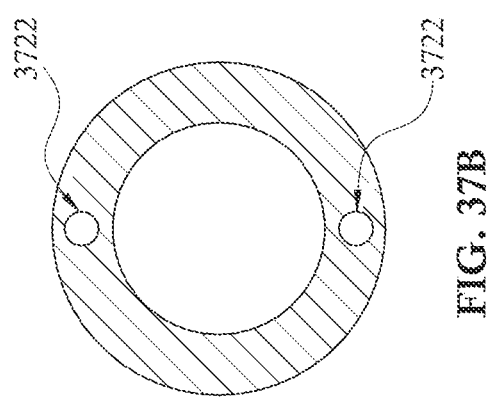

FIGS. 37A and 37B illustrate features that may be included as part of some embodiments of the housing component 510 when considering the requirements for a miniature internal motor 202, (not shown; e.g. the motor 202 in FIG. 15) as may be used for the pump system 200 as shown in FIG. 2. In this embodiment, the drive shaft housing 511 may include lumens 3722 embedded within the wall of the drive shaft housing 511. These lumens 3722 may accommodate the passage of the wires 1506 (not shown; refer to FIG. 15) which may connect the motor 202 inside the patient's body to the controller 206 outside the patient's body, in order to power and control the motor 202.

FIGS. 38A-38E illustrate examples of a torque-transmitting drive shaft 3800, in accordance with embodiments of the subject matter disclosed herein. The drive shaft 3800 may be used as, for example, the drive shaft 704 of the rotatable inner catheter of the pump devices described herein.

In some embodiments, the drive shaft 3800 is constructed of a bi-directional helical hollow stranded coil 3802. The coils 3802 have high performance torque transmitting properties and facilitate flexibility and tracking through anatomy. As illustrated, the coils 3802 may be unencapsulated (FIGS. 38A and 38B) or encapsulated by an outer cover 3804 (FIGS. 38C-38E). The outer cover 3804 may be constructed of a polymer and isolate a central lumen 3806 (FIG. 38D) of the drive shaft 3800 from its external environment. As a result, the central lumen 3806 may be used as an inflation lumen to provide an inflation fluid to the pump impeller 708 (shown elsewhere). The outer cover 3804 may also enhance torque transmission and decrease longitudinal elongation of the drive shaft 3800.

With specific reference to FIG. 38E, in some embodiments a lumen support mandrel 3808 may be removably inserted into the central lumen 3806 to further enhance torque transmission. The mandrel 3808 may have different surface finishes or coatings to facilitate insertion in the central lumen 3806 of the drive shaft 3800 or facilitate coupling between the drive shaft 3800 and the mandrel 3808 during rotation. The luminal support mandrel 3808 may rotate at the same angular velocity as the coils 3802, thereby reducing friction and wear between the components.

The luminal support mandrel 3808 may inhibit transmission of an inflation fluid via the central lumen 3806 and, as a result, the inflation fluid may be transmitted before insertion of the mandrel 3808. In fact, in some cases the mandrel 3808 may act as a plunger in the central lumen 3806 and thereby increase the hydraulic pressure provided to the pump impeller 708 (shown elsewhere). As a result, it may be beneficial to consider the pressure increase caused by insertion of the mandrel 3808 when initially providing the inflation fluid to the pump impeller 708 via the lumen 3806 of the drive shaft 3800. Alternatively, a pressure release valve (not shown) may be included to maintain the desired pressure.

FIGS. 39A-39C further illustrate the drive shaft 3800 and potential failure modes thereof. More specifically, FIG. 39B illustrates one potential failure mode 3810 of the drive shaft 3800 that may result when subjected to high levels of rotational resistance. Due to the presence of the central lumen 3806 (FIGS. 38B and 38D), the drive shaft 3800 may collapse down upon itself when subjected to high levels of torque, thereby compromising torque transmission at the collapsed location. This leads to a stress riser in which the drive shaft 3800 begins to wrap on itself at the collapsed location instead of transmitting torque and, eventually, the drive shaft 3800 will separate at the collapsed location 3810. When the drive shaft 3800 is rotated at a high angular velocity, the time between such a collapse and drive shaft separation is extremely short. As a result, there may not be sufficient time for reacting to a collapsed drive shaft and stopping drive shaft rotation.

With specific reference to FIG. 39C, one solution to mitigate this failure mode is to place the luminal support mandrel 3808 within the central lumen 3806 of the drive shaft 3800. The presence of the mandrel 3808 in the central lumen 3806 inhibits collapse of the drive shaft 3800, thereby inhibiting formation of a stress riser and avoiding the failure mode. The mandrel 3808 may also provide additional benefits, such as improved kink resistance, durability, and fatigue resistance.

FIGS. 40A-40D illustrate the drive shaft 704, a drive shaft hub 4002, and inflation needle 4006 in accordance with embodiments of the subject matter disclosed herein. The drive shaft 704 and the drive shaft hub 4002 may be, for example, part of the system 100 (FIG. 1). The drive shaft hub 4002 and the drive shaft 704 define lumens that may facilitate the transmission of an inflation fluid from the inflation needle 4006 to the pump impeller 708 (shown elsewhere).

The drive shaft hub 4002 can be configured to maintain the pressure of the inflation fluid once the inflation needle 4006 is detached. More specifically, the drive shaft hub 4002 may carry or include a drive shaft hub seal 4004, which may be a septum or pressure activated seal.

Embodiments of the drive shaft hub 4002 that include a pressure activated drive shaft hub seal 4004 can be manually compressible and extendable. In some such embodiments, the drive shaft hub 4002 can comprise two portions that are in threaded engagement with each other, and that are manually compressible and extendable by manually adjusting the extent to which the two part are threaded together. In another example embodiment, the drive shaft hub 4002 can comprise a detent mechanism by which the drive shaft hub 4002 can be manually adjusted between a compressed configuration (FIG. 40C) and an extended configuration (FIG. 40A).

When the drive shaft hub 4002 is extended, as shown in FIG. 40A, the pressure activated driveshaft hub seal 4004 is open or readily openable. When the drive shaft hub 4002 is compressed, as shown in FIG. 40C, the pressure activated drive shaft hub seal 4004 is compressed causing the pressure activated drive shaft hub seal 4004 to close and inhibit flow therethrough.

In some embodiments, the drive shaft hub 4002 may carry multiple seals 4004. The drive shaft hub 4002 may also permit the drive shaft 704 to receive the mandrel 3808 (e.g., FIG. 38E) without a loss of pressure.

With continued reference to FIGS. 40A-40D and specific reference to FIG. 40A, the inflation needle 4006 may be manually inserted and extended through the hub seal 4004 while the hub seal 4004 is in its open or openable state. While the inflation needle 4006 is extending through the hub seal 4004, the hub seal 4004 compresses and thereby seals around the inflation needle 4006. Thereafter, inflation fluid may be delivered via the inflation needle 4006 to inflate the pump impeller coupled to the drive shaft 704 (e.g., pump impeller 708). After an appropriate pressure within the pump impeller is reached, the inflation needle 4006 may be slidably retracted proximally, and the hub seal 4004 closes to maintain the seal once the inflation needle 4006 is fully removed. At such a time, the pump impeller is pressurized (and expanded) and sealed.

If a drive shaft luminal support mandrel 3808 is to be used, it may be inserted by pushing it through the seal 4004 and tracking it through the drive shaft 704 without depressurizing the system. The drive shaft hub 4002 may also include features that facilitate coupling to a motor. For example, FIG. 40D illustrates that the hub 4002 can define coupling features such as three symmetrically placed grooves 4008 around the outer perimeter to facilitate coupling and torque transmission between a motor (shown elsewhere) and the drive shaft 704.

FIGS. 41A and 41B illustrate an example expandable, inflatable, or balloon-based pump impeller 4100, in accordance with embodiments of the subject matter disclosed herein. The impeller pump 4100 includes smooth surfaces without any protruding external features, such as grooves or ridges (e.g., as shown in some other impellers herein). The pump impeller 4100 with the smooth surfaces may have enhanced self-centering capabilities. The impeller 4100 may be attached to the distal end of the drive shaft 704 at both the distal and proximal waists of the impeller, thereby allowing for even torque transmission between the drive shaft and the impeller from both the proximal and distal ends of the impeller.

FIGS. 42A and 42B illustrate an example of a self-expandable, or a hybrid between self-expandable and balloon-based, pump impeller 4200, in accordance with embodiments of the subject matter disclosed herein. The impeller 4200 may include a self-expanding support structure 4204 within impeller 4200. Once un-sheathed, this support structure 4204 may expand to bring the impeller 4200 to its full expanded operational pumping profile. In a self-expanding impeller configuration, no inflation medium or inflation technique may be required. The self-expanding impeller 4200 may be slidably tracked through the internal lumen of the drive shaft housing 511 (shown elsewhere) in a collapsed state and then it self-expands once it is advanced into the pump housing 508 (shown elsewhere). To re-collapse the self-expanding impeller 4200, for device removal, the impeller 4200 and drive shaft 704 (shown elsewhere) may be retracted proximally through the drive shaft housing 511.

In this configuration, the impeller 4200 may also be a hybrid expandable impeller 4200, where the support structure 4204 facilitates the expansion of a portion of the impeller 4200 and the addition of pressure within the balloon-based impeller 4200 may contribute additionally to fully expanding the impeller 4200. Once expanded, the impeller may rotate around its axis 4202 to create blood flow.

FIGS. 43A-43C illustrate an example expandable, triangular pump impeller 4300, in accordance with embodiments of the subject matter disclosed herein. In this configuration, the impeller 4300 expansion may be facilitated by a triangular support structure 4304. The support structure 4304 may have a three filar configuration that expands within the impeller 4300 membrane once un-sheathed. This expansion may be self-expandable, or expandable through longitudinal compression along the rotational axis 4302 of the impeller. FIG. 43B shows the expanded triangular impeller 4300 within the pump housing 508 and illustrates a small clearance gap between the triangle corners of the impeller 4300 created by the internal support structure 4304 and the pump housing's 508 flexible wall 524 and the pump housing 508 exit ports 526. When the impeller 4300 rotates about its axis 4302, it may create flow by pushing blood out through the pump housing 508 exit ports 526. This configuration of the impeller is shown to be triangular, however, it may also be flat (not shown) with a two filar support structure or have a plurality of filars to create an impeller with any number of flat surfaces (not shown). In some embodiments, these internal filar support structures may spiral around the impeller's 4300 central axis 4302 when expanded to create helical surfaces (not shown).

FIGS. 44A-44C illustrate another example expandable, inflatable, or balloon-based pump impeller 4400, in accordance with embodiments of the subject matter disclosed herein. In this example, the impeller 4400 may have a plurality of ridges 4406 disposed along the external surface 4404 of the impeller 4400. In the depicted embodiment, the plurality of ridges 4406 are aligned longitudinally along, or parallel to, the axis 4402 of the impeller 4400.

There are many different possible configurations for creating the ridges 4406. A few non-limiting examples are that the ridges 4406 may be solid, non-expanding ridges formed directly into the external surface 4404 of the impeller 4400. The ridges 4406 may also be pressure-expandable and inflate when the balloon-based impeller 4400 is pressurized. Pressure-expandable ridges 4406 may be formed directly into the surface of the impeller 4400, or may be long and thin tubular balloons bonded onto the external surface 4404 of the impeller 4400 which have separate internal lumens within the ridges 4404.

These ridges 4406 may further increase the blood contacting surface area of the impeller 4400 to create more push against the blood by having the angled surface of the ridges 4406 pushing against the blood instead of only having the tangentially spinning surface 4404 propelling the blood. These ridges 4406 may lead to an increased flow rate per rpm and a decrease in blood shear stresses.

FIGS. 45A-45C illustrate another example expandable, inflatable, or balloon-based pump impeller 4500, in accordance with embodiments of the subject matter disclosed herein. In this example, the impeller 4500 is similar to impeller 4400 (see FIGS. 44A-44C) however, the plurality of ridges 4506 disposed around the external surface 4504 of the impeller 4500 may be aligned in a spiral configuration along the axis 4502 of the impeller 4500, instead of being aligned longitudinally along the axis 4402 of the impeller 4400. Having a spiral configuration may increase blood flow rate per rpm and decrease blood shear stresses.

FIGS. 46A-46D illustrate another example expandable, inflatable, or balloon-based pump impeller 4600, in accordance with embodiments of the subject matter disclosed herein. In contrast to ridges along the external surface of the impellers (shown above), the impeller 4600 may have a plurality of valley features 4608 disposed along the external surface 4604 of the impeller 4600. The valleys 4608 may also be referred to as grooves, channels, recesses, and the like. The valleys 4608 may be disposed longitudinally, extending parallel to the axis 4602 of the impeller 4600. Some non-limiting examples for how the valleys 4608 may be created are that the valleys 4608 may be formed directly in the external surface 4604 of the impeller membrane 4604 or they may be formed using a support structure 4606 disposed externally to the surface 4604 of the impeller 4600. The support structure 4606 may act as a cage around the impeller 4600, thereby preventing the impeller 4600 from fully expanding at the location of the support structure 4606 when fully inflated. This prevention of full expansion is what may create these valleys 4608. These valleys 4608 may lead to an increased flow rate per rpm and a decrease in blood shear stresses.

FIGS. 47A-47C illustrate another example expandable, inflatable, or balloon-based pump impeller 4700, in accordance with embodiments of the subject matter disclosed herein. In this example, the impeller 4700 is similar to impeller 4600 (see FIGS. 46A-46D) however, the plurality of valleys 4706 disposed along the external surface 4704 of the impeller 4700 may extend along a spiral configuration around the axis 4702 of the impeller 4700 instead of being aligned longitudinally along the axis 4602 of the impeller 4600. Having a spiral configuration may increase blood flow rate per rpm and decrease blood shear stresses.

FIGS. 48A and 48B illustrate another example expandable, inflatable, or balloon-based pump impeller 4800, in accordance with embodiments of the subject matter disclosed herein. Similar to impeller 4100 (see FIGS. 41A and 41B), the distal impeller surface may have the same profile. However, the proximal surface 4804 may be flattened out leading to a larger angle between the proximal surface 4804 and the axis of rotation 4802. The impeller 4800 having a flattened out proximal surface 4804 may reduce blood backflow through the pump housing created by the proximal end of the impeller in comparison to the proximal surface of impeller 4100.

FIGS. 49A and 49B illustrate another example expandable, inflatable, or balloon-based pump impeller 4900. Impeller 4900 is similar to impeller 4800 (shown above), however, the proximal surface 4904 may have a concave profile. This concave proximal surface 4904 may reduce blood backflow through the pump housing created by the proximal end of the impeller 4900 in comparison to the proximal surface of impeller 4800.

FIGS. 50A and 50B illustrate another example expandable, inflatable, or balloon-based pump impeller 5000. Impeller 5000 is similar to impeller 4800 (shown above), however, the proximal surface 5004 may have a convex profile.

With general reference to FIGS. 48A-50B, the proximal surface of the impeller may be designed to reduce the pumping action and minimize the blood backflow through the pump housing. This may be desired to reduce the amount of time blood is in contact with the impeller as well as to reduce the risk of the impeller aspirating air through the device hub. In contrast, the proximal surface of the impeller may be designed to increase the pumping action and/or to maximize the blood backflow through the pump housing. Specifically tailoring and/or increasing the blood backflow may be desired because the backflow may be used as a lubricant or coolant to improve impeller self-centering within the pump housing as well as to improve drive shaft to drive shaft housing interactions (e.g., reduce friction, provide cooling, etc.). In some embodiments, a purge fluid (e.g., saline, Dextrose, etc.) from outside the body may be introduced into the drive shaft housing to act as a lubricant or coolant to improve impeller self-centering within the pump housing and/or to improve drive shaft to drive shaft housing interactions (e.g., reduce friction, provide cooling, etc.).

FIGS. 51A and 51B illustrate another example expandable, inflatable, or balloon-based pump impeller 5100, in accordance with embodiments of the subject matter disclosed herein. When considering a catheter-based blood pump configured in a blood pushing configuration (e.g., pump device 400, FIGS. 4 and 10), the impeller of the system may have some modifications as compared to impellers of blood pulling pump devices. With the blood moving in a proximal to distal direction, the design of the impeller may be optimized to pump blood in said direction. Many of the impeller examples disclosed are configured for a blood pulling configuration, however, if the impellers are flipped proximal to distal, then their designs would be optimized for increasing blood flow in a proximal to distal direction in relation to the catheter.

In FIGS. 51A and 51B, the impeller 5100 profile is similar to the impeller 4100 (see FIG. 41). However, what is the distal end of impeller 4100, is now the proximal end of impeller 5100. The distal surface 5104 of impeller 5100 differs from the proximal surface of impeller 4100. With a blood pushing configuration, there may not be a cannula extending distally from the end of the pump housing 408 (see FIG. 10) therefore, the impeller 5100 may be configured without a distal tip protruding along the axis 5102. The impeller's 5100 distal tip may be folded back inside itself to create a truncated distal tip, or a more rounded distal tip as shown. This impeller 5100 tip profile may improve the interaction between the impeller 5100 and the closed distal configuration of the pump housing 408.

FIGS. 52A-52D illustrate another example expandable pump impeller 5200, in accordance with embodiments of the subject matter disclosed herein. The pump impeller 5200 includes a plurality of expandable ridges 5202 that may provide improved fluid pumping dynamics. The ridges 5202 begin at the distal portion 5204 of the pump impeller 5200, progress through the maximum diameter portion 5206 of the impeller pump 5200, and terminate before the proximal portion 5208 of the impeller pump 5200. Such ridges 5202 provide relatively large gaps therebetween, and such gaps may act as channels for blood ingress.

In some embodiments, the ridges 5202 may have a tapered width, as illustrated in FIG. 52D, where the distal tip of the ridges 5202 have a width of X, and the proximal portion of the ridges 5202 have a greater width of Y (where X<Y). This tapering width may also facilitate efficient ingress of blood between the ridges 5202.

With continued reference to FIGS. 52A-52D, in the depicted non-limiting embodiment the ridges 5202 extend helically or spirally relative to the longitudinal/rotation axis 5210 of the pump impeller 5200. More specifically, the ridges 5202 are offset from the longitudinal axis 5210 (if the ridges 5202 are extended, they will never converge on the rotational axis 5210 of the impeller 5200) and wrap around the surfaces of the pump impeller 5200 at a uniform angle. Alternatively, the ridges 5202 may wrap around the pump impeller 5200 at a variable, non-uniform angle.

FIGS. 53A-53C illustrate another example expandable pump impeller 5300, in accordance with embodiments of the subject matter disclosed herein. The pump impeller 5300 is similar to the impeller 5200 illustrated in FIGS. 52A-52D, except that the pump impeller 5300 includes segmented expandable ridges 5302 that are spaced apart from each other along their length by one or more gaps 5304. As the pressure increases within the pump impeller 5300, the pump impeller 5300 will tend to round out, thereby reducing the protrusion height of the ridges 5302. The gaps 5304 may not expand when the pump impeller 5300 is pressurized, and the gaps 5304 thereby act as tethers to provide hoop strength to maintain the integrity of the expanded impeller profile and the ridges 5302.

Figure 54B:
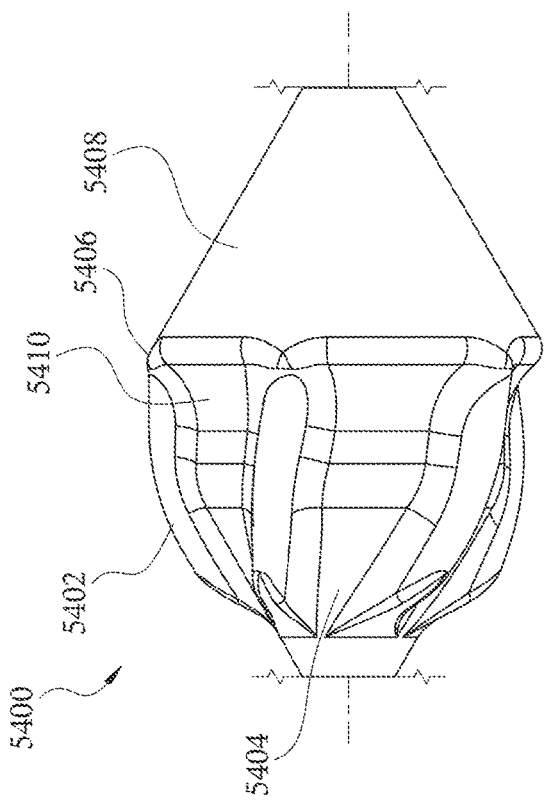
FIGS. 54A-54C illustrate another example expandable impeller of a mechanical hemodynamic support device, in accordance with embodiments of the subject matter disclosed herein.
Figure 54C:
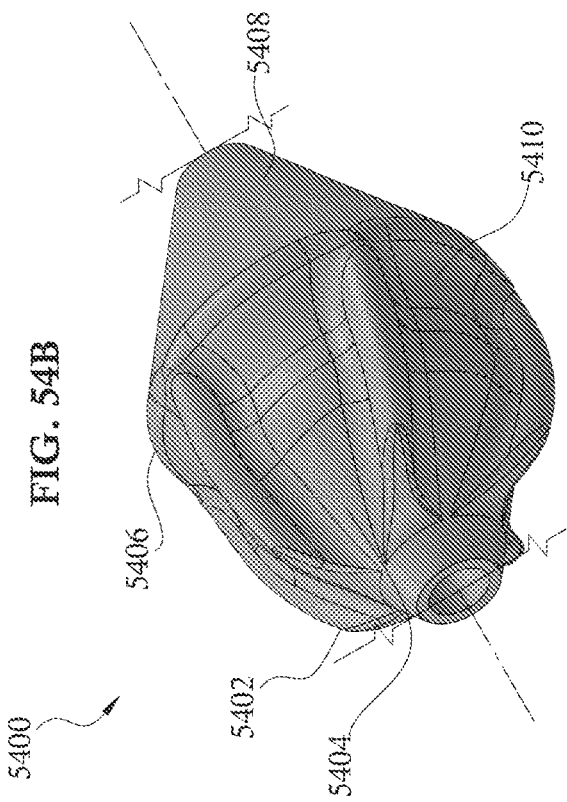
Figure 54A:
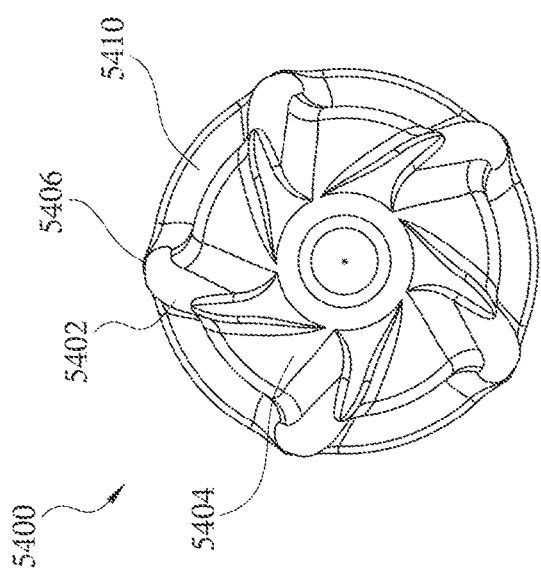

FIGS. 54A-54C illustrate another example expandable pump impeller 5400, in accordance with embodiments of the subject matter disclosed herein. The pump impeller 5400 is similar to the impeller 5200 illustrated in FIGS. 52A-52D, except that the pump impeller 5400 includes a plurality of tapered and angled ridges 5402 on the distal portion 5404 and the maximum diameter portion 5406. The proximal portion 5408 has a smooth surface and is relatively large to converge with the outermost dimensions of the ridges 5402. Such a proximal portion 5408 may provide several advantages. One advantage is that there is no step along the side profile of the pump impeller 5400—as a result, it may be relatively easy to construct a smooth walled pump housing that matches the rotating profile of the impeller 5400. Another advantage is that the proximal portion 5408 may enhance self-centering performance of the pump impeller 5400. Yet another advantage is that the pump impeller 5400 defines blood re-direction ramps 5410. Such ramps 5410 may re-direct the blood from an axial flow path to a radial flow path, thereby pushing blood circumferentially out of the pump housing outlets.

FIGS. 55A-55D illustrate another example expandable pump impeller 5500, in accordance with embodiments of the subject matter disclosed herein. The pump impeller 5500 is similar to the impeller 5400 illustrated in FIGS. 54A-54D, except that the pump impeller 5500, while being generally inflatable and expandable, includes a plurality of non-expandable ridges 5502, which may also be referred to as fins. The fins 5502 may be formed by fusing balloon membranes of the pump impeller 5500 together, thereby making the fins 5502 non-expandable. However, the fins 5502 are nevertheless flexible, thereby permitting the fins 5502 to be radially collapsed to a relatively small delivery profile.

In the expanded configuration of the pump impeller 5500 (as shown), the fins 5502 are supported by the hydraulic pressure used to inflate the pump impeller 5500. Additionally, the spine of each fin 5502 may be under tension between the distal portion 5504 of the pump impeller 5500 and the maximum diameter portion 5506 of the pump impeller 5500.

With sufficient hydraulic pressure in the pump impeller 5500, the fins 5502 may withstand the blood pressure exerted on them when rotating and pumping blood. The pump impeller 5500 may also define blood re-direction ramps 5508 to direct blood through the pump housing outlets.

As illustrated in FIGS. 55A-55C, in some embodiments the fins 5502 may extend non-helically or along linear pathways relative to the longitudinal/rotation axis 5510 of the pump impeller 5500. Alternatively, and as illustrated specifically in FIG. 55D, in some embodiments the pump impeller 5500 may include the fins 5512 extending helically or along curved pathways relative to the longitudinal/rotation axis 5510.

Figure 56E:
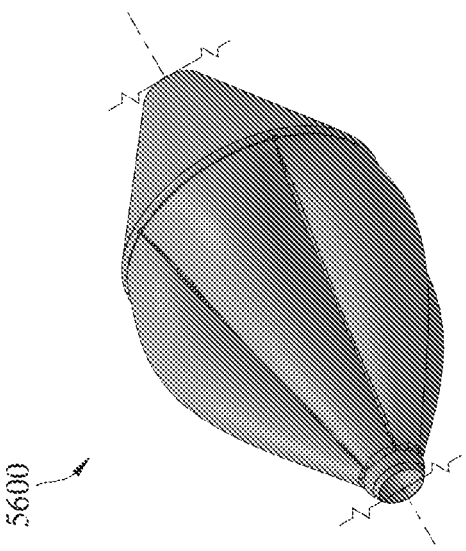
FIGS. 56A-56F illustrate components and steps of an example method for manufacturing an expandable impeller, in accordance with embodiments of the subject matter disclosed herein.
Figure 56F:
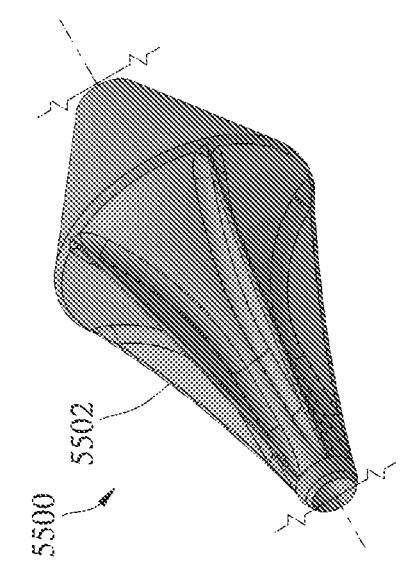
Figure 56C:
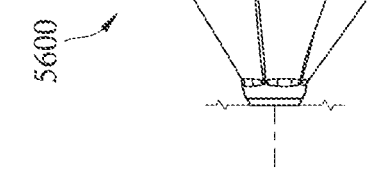
Figure 56D:
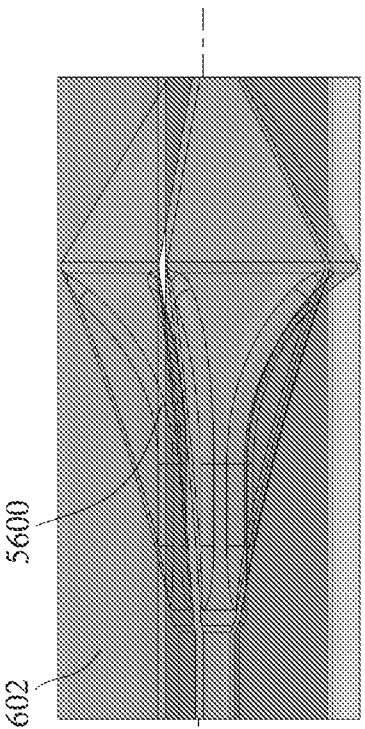
Figure 56A:
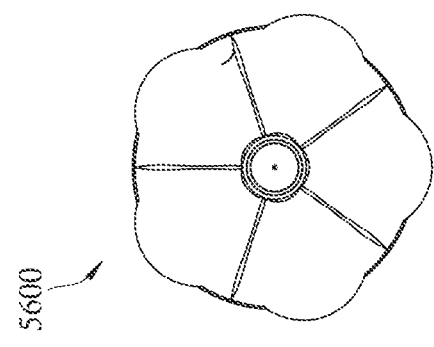
Figure 56B:
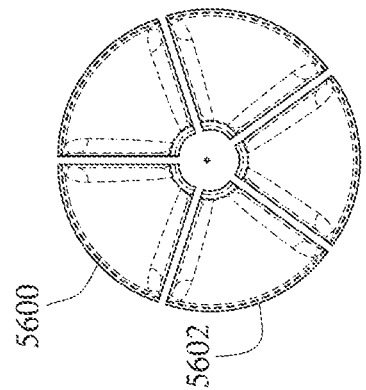

FIGS. 56A-56F illustrate components and steps of a method for manufacturing the pump impeller 5500 of FIGS. 55A-55D, in accordance with embodiments of the subject matter disclosed herein. First, and as illustrated in FIGS. 56A, 56C, and 56E, a preform 5600 of the impeller without fins is blown to an enlarged configuration. Next, and as illustrated in FIGS. 56B and 56D, the enlarged preform 5600 is positioned in a fixture 5602 including an internal profile corresponding to the desired final profile of the pump impeller 5500. The preform 5600 may be pressurized and positioned in the fixture 5602 while sections of the fixture 5602 are separated from each other. Next, the sections of the fixture 5602 may constrict, like an iris, until the sections contact each other. The preform 5600 and the fixture 5602 may be heated to cause the membranes to fuse together and thereby form the fins 5502 (FIG. 56F). Alternatively, the pump impeller 5500 may be formed by creating the membrane from a co-extrusion with a tie-layer on the internal diameter of the extrusion, thereby increasing the bonding strength of the fusion.

Figure 57A:
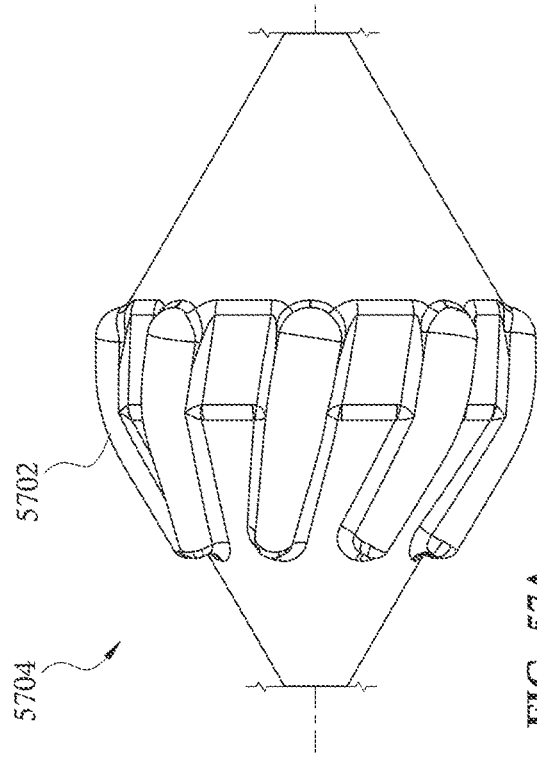
FIGS. 57A-57B illustrate components and steps of an example method for manufacturing another expandable impeller, in accordance with embodiments of the subject matter disclosed herein.
Figure 57B:
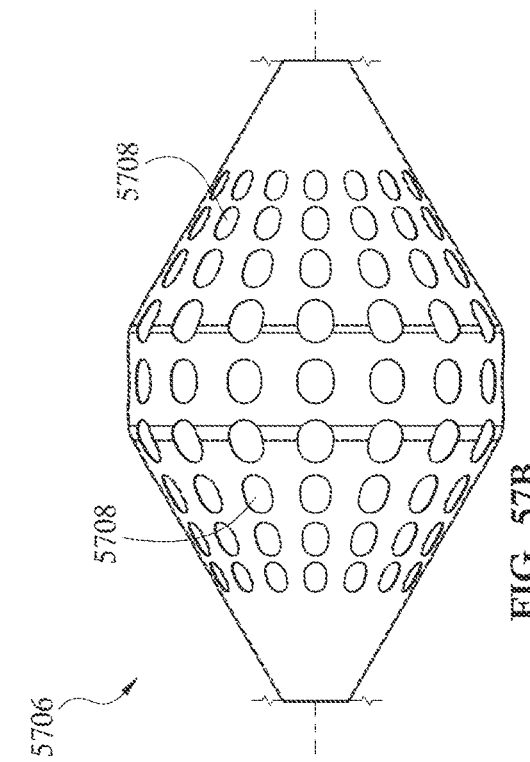
Figure 57C:
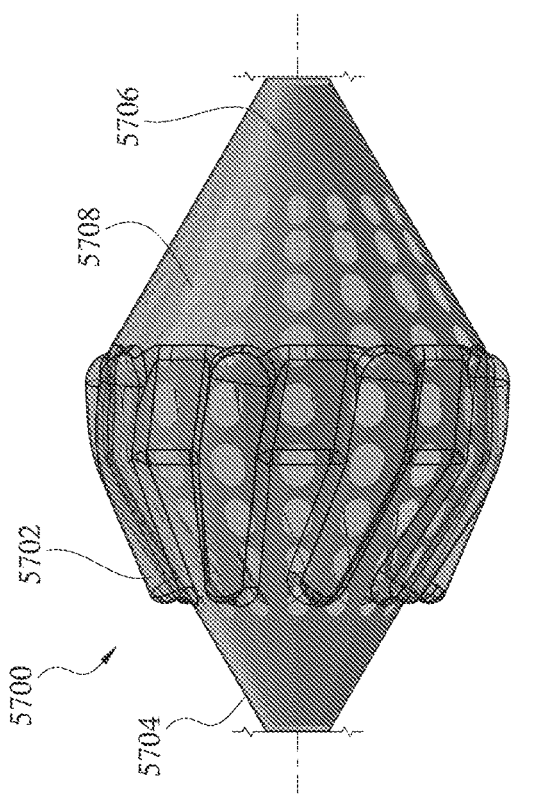
FIGS. 57C-57D illustrate an expandable impeller created by the method illustrated in FIGS. 57A-57B, in accordance with embodiments of the subject matter disclosed herein.
Figure 57D:
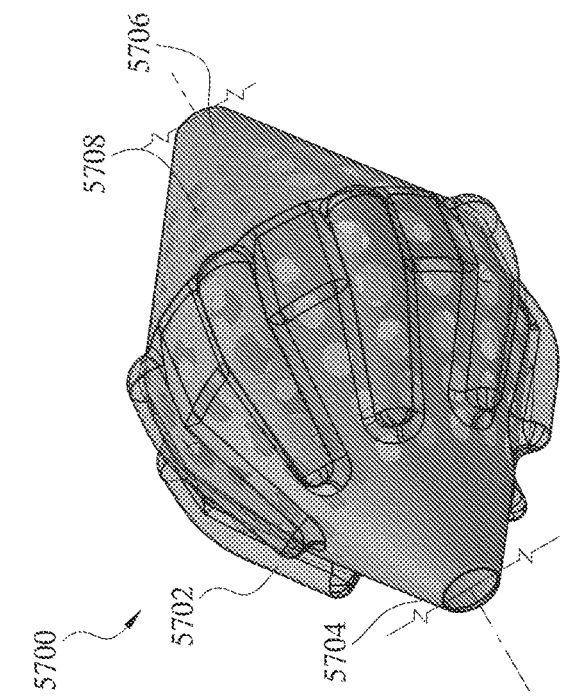

FIGS. 57A and 57B illustrate components and steps of a method for manufacturing another example pump impeller 5700 including expandable ridges 5702, as illustrated in FIGS. 57C and 57D, in accordance with embodiments of the subject matter disclosed herein. The method generally includes joining two membrane layers. The membrane layers include an outer layer 5704, illustrated in FIG. 57A, which is formed to the desired external impeller profile. The membrane layers also include an internal layer or mesh 5706, illustrated in FIG. 57B. The internal mesh 5706 includes a plurality of holes 5708 that may be created by laser cutting. After creating the outer layer 5704 and the internal mesh 5706, the internal mesh 5706 may be positioned in the outer layer 5704, and the outer layer 5704 and the internal mesh 5706 may be fused together to create the pump impeller 5700 as illustrated in FIGS. 57C and 57D. Such a construction of the pump impeller 5700 may make it less susceptible to rounding out when pressurized, thereby maintaining its shape (including the shape of the expandable ridges 5702). The strength of the fusion bond between the membrane layers may be increased by using co-extrusions with a tie-layer on the fusing side of the layers.

FIGS. 58A-58C illustrate components and steps of a method for manufacturing another example pump impeller 5800 including expandable ridges 5802, as illustrated in FIGS. 58D and 58E, in accordance with embodiments of the subject matter disclosed herein. First and as shown in FIG. 58A, an internal compliant or semi-compliant membrane 5804 is formed. FIG. 58A illustrates the membrane 5804 as formed and without being pressurized. FIG. 58B illustrates the pressurized membrane 5804 stretching and rounding out. FIG. 58C illustrates an outer layer 5806 constructed of a noncompliant material including a plurality of openings 5808 that define the base perimeter of the expandable ridges 5802. The outer layer 5806 is laminated over the membrane 5804. The outer layer 5806 thereby acts as a cage to constrict expansion of the membrane 5804 when pressurized. That said, the openings 5808 do not constrict the membrane 5804 from expanding and thereby permit the membrane 5804 to expand and stretch through the openings 5808 when pressurized, creating the ridges 5802. As a result and as illustrated in FIGS. 58D and 58E, the pump impeller 5800 is a dual layer impeller with expandable ridges 5802. The strength of the laminating bond between the membrane layers may be increased by using co-extrusions with a tie-layer on the fusing side of the layers.

FIGS. 59A and 59B illustrate components and steps of a method for manufacturing another example pump impeller 5900 including expandable ridges 5902, as illustrated in FIG. 59C, in accordance with embodiments of the subject matter disclosed herein. The method is similar to the method illustrated in FIGS. 58A-58C, except that a single co-extrusion, as shown in FIG. 59A, may be used to create the impeller membrane 5904. The external layer of the co-extrusion may be non-compliant, and the internal layer may be compliant or semi-compliant. Openings in the external layer 5906 may be created, for example, by ablating off the external layer, therefore allowing the internal layer to expand through the openings 5906 and creating the expandable ridges 5902, as illustrated in FIG. 59C.

FIGS. 60A and 60B illustrate an example method of using a pressurized balloon in a patient's cardiovascular system to act as a pressure transducer and thereby provide measurements of the patient's systolic and diastolic pressure. The method includes using a balloon pressure transducer system 6000, and the system 6000 includes a balloon 6002, a pressure gauge inflation conduit 6004, and a pressure gauge 6006. After the balloon 6002 is positioned in the left ventricle and inflated, the pressure gauge 6006 registers the internal gauge pressure of the balloon 6002. During diastole, the balloon 6002 will have less external pressure exerted upon it. As a result, and as illustrated in FIG. 60A, the gauge 6006 will read a relatively low diastolic pressure 6008 (for example, 80 mmHg). During systole, the balloon 6002 will have more external pressure exerted upon it. As a result, and as illustrated in FIG. 60B, the gauge 6006 will read a relatively high systolic pressure 6010 (for example, 120 mmHg).

Any of the expandable, inflatable, or balloon-based, pump impellers described herein may be used to perform the function of the balloon 6002 for measuring blood pressure. More specifically, after the pump impeller is inflated and rotating to pump blood, there will be a rhythmic external pressure variation exerted on the pump impeller due to the patient's QRS complex resulting from the continued heartbeat of the patient. While the pumping action of the catheter-based blood pump may change the external blood pressures experienced by the balloon-based impeller, with proper adjustment factors, the internal pressure rhythm of the balloon-based impeller may be monitored to calculate an accurate blood pressure reading. A non-exhaustive list of adjustment factors to be accounted for include pressure losses along the internal lumen of the drive shaft, angular velocity of the impeller, initial baseline inflation pressure of the impeller, and the patient's initial diastolic and systolic arterial pressures prior to placement of the mechanical hemodynamic support device.

Figure 61:
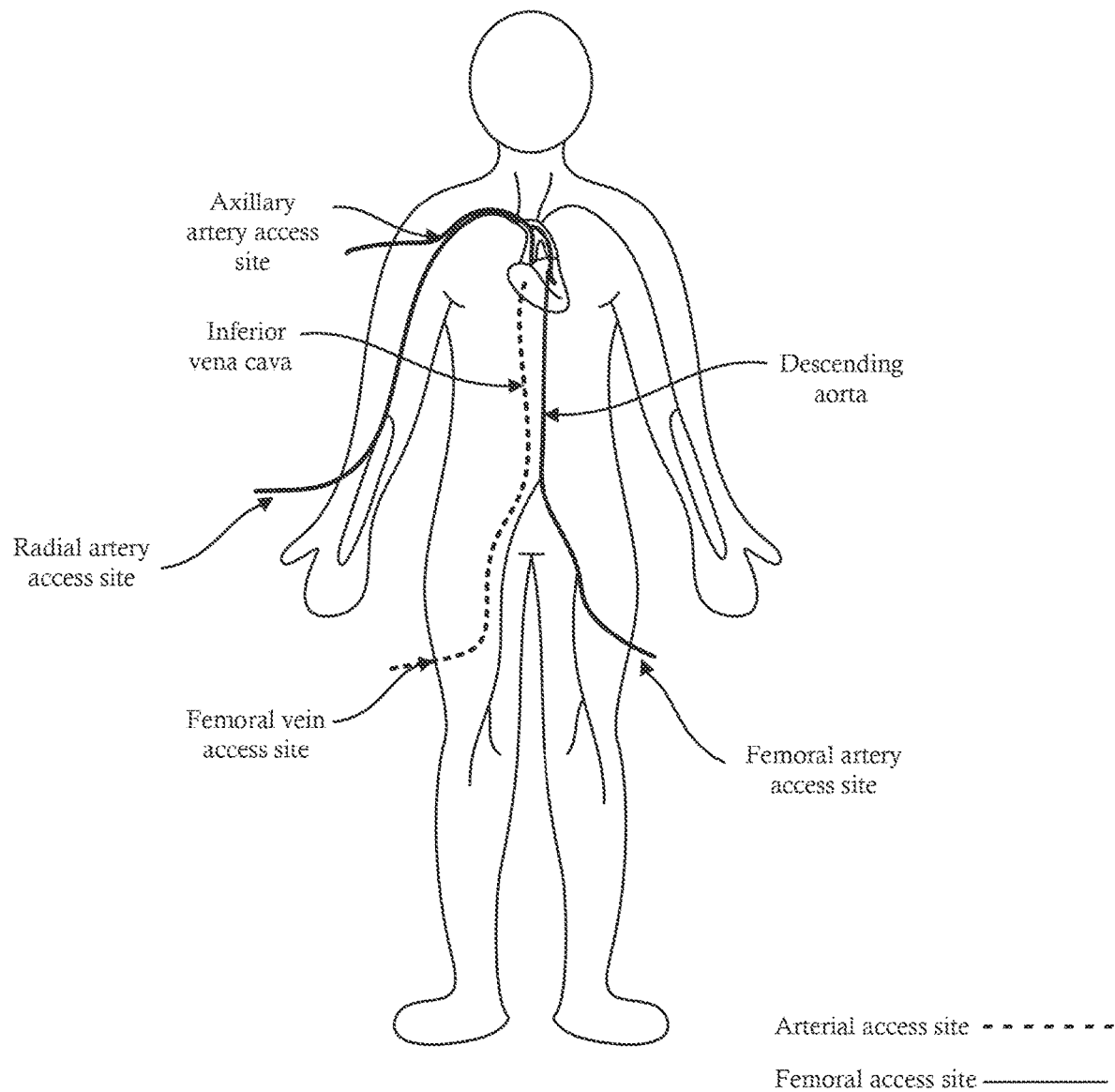
FIG. 61 illustrates different arterial and venous access sites and pathways for delivery of mechanical hemodynamic support devices to a patient's heart.

FIG. 61 illustrates different arterial and venous access sites and pathways for delivery of the mechanical hemodynamic support devices described herein to a patient's heart. The most common access site is the femoral artery because it accommodates larger devices, is easy to access, and is easy to subsequently seal. Axillary artery access sites may alternatively be used if the patient has femoral arteries that are too small or too diseased to accommodate a device. With an appropriate mechanical hemodynamic support device, such as the pumping devices described herein, the use of a radial access site either through the wrist or through a snuff box access site is, for the first time, possible and beneficial because of the ease of access and the ease of access site closure.

Venous access sites may be used to place mechanical hemodynamic support devices in the right ventricle to support pulmonary circulation. Right heart circulatory support may be provided alone, or in conjunction with left heart circulatory support to provide full heart circulatory support. Additionally, a venous access site may be used and then a mechanical hemodynamic support device may be tracked through a trans-caval or an atrial transseptal pathway to reach the arterial system and provide left heart circulatory support if direct arterial access is not possible.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

OPTIONAL FEATURES AND ADDITIONAL EMBODIMENTS

With general reference to inflatable balloon-based pump impellers, some embodiments may utilize the fact that the impeller spins at a high rpm to assist with impeller expansion. That is, when the pump impeller is spinning, it imparts centrifugal force on the inflation fluid within the impeller. The impeller will tend to expand in response to the inflation fluid's centrifugal force. As a result, additional inflation fluid will be drawn into the impeller to fully expand the impeller. The centrifugal force may be sufficient to maintain a balloon in an inflated or expanded operational state. When centrifugal force is used in such a manner, then the rotatable inner catheter 700 need not be a fully sealed system in some examples.

An inflatable balloon-based pump impeller may be inflated, for example, via a luer adaptor using standard balloon catheter inflation medium (e.g., a mixture of saline and contrast), or it may also be inflated with a more viscous fluid or a higher density fluid. The impeller may also be inflated with a fluid that takes a gelatinous set to help the impeller maintain its surface features once expanded and spinning. To deflate the impeller that is filled with a liquid that sets may require the additional delivery of a chemical or enzyme to break down the gelatinous structure. If the impeller is inflated with a mixture of saline and contrast, for example, then it may be deflated with standard balloon deflation techniques (e.g., suction of the inflation medium).

In some embodiments, the impeller may have one or a plurality of radiopaque markers that help the user identify the location of the impeller in relation to the patient anatomy and in relation to the pump housing to ensure correct placement. These radiopaque markers may be placed either on the impeller membrane, or on the drive shaft within the impeller, or a combination of both locations. Additionally, in some embodiments the inflation medium used to expand the impeller may be radiopaque, thereby allowing the full impeller to be visible under fluoroscopy.

With general reference to the rotatable drive shaft that drives the pump impeller, in accordance with embodiments of the subject matter disclosed herein, if the impeller is designed as a self-expanding impeller (as opposed to a hydraulically expandable impeller), then there may be no need for the drive shaft to include an inflation lumen. Accordingly, in some such embodiments the drive shaft may therefore be designed as a solid cable, without any lumen for inflation medium delivery to the impeller.

A torque transmitting drive shaft may optionally contain structural reinforcement that is designed to maintain flexibility while transmitting torque. Several possible designs for the structural reinforcement include a structure made of a hypotube with a pattern laser cut out of the walls to increase flexibility. This may also be combined with a second layer of a laser cut hypotube with a mirroring (opposite) pattern to the first hypotube to further increase torque transmission. The support may also be made of multifilar coils such as HHS ("Helical Hollow Strand") coils in either a single or two bi-directional, or even three directional coils concentrically placed inside one another. Multifilar coil reinforcement provides robust flexibility and torque transmission properties. The structural reinforcement may also be a combination of the aforementioned support structures. A polymer membrane liner may be placed either on the inside of the hollow shaft, or on the outside of the hollow shaft, to seal the shaft and create an inflation lumen. The inside or outside of the coils may have a polymer membrane or a polymer jacket to seal off the shaft and create an inflation lumen for inflating a balloon impeller.

In some embodiments, the structural torque transmitting elements may be made of a twisted stranded cable that may be wound in a single layer or in two opposing layers or three opposing layers. In a cable configuration, because there is no hollow opening on the inside of the cable, there can be a loose-fitting membrane around the outside of the cable with enough clearance for fluids to pass between the membrane and the cable. When rotating, both the membrane and the cable may rotate at the same angular velocity.

With general reference to the two catheter systems that rotate relative to each other and the system components implanted within a patient, in accordance with embodiments of the subject matter disclosed herein, there may be coatings disposed on the surfaces of the components which make up the catheter based blood pump. Friction reducing coatings such as but not limited to a hydrophilic coating or a hydrophobic coating, like silicone, may be applied to reduce component wear. Thrombus reducing coating such as but not limited to a heparin coating may be used to reduce the changes of thrombus forming on the surface of the components. A bioactive or biocompatibility improving coating such as but not limited to a hydrogel or a Limus drug based coating may be used to reduce the patient's response to the presence of foreign objects within the body.

Specifically regarding friction-reducing coatings, they may be applied to the exterior of the sheath 500 to facilitate tracking the sheath through the access site and the anatomy. A friction reducing coating may also be applied to the interior of the sheath 500 or the exterior of the housing component 510 (or both) to reduce the friction between the two components, thus facilitating retraction of the sheath 500 and expression of the inlet cannula 504 and pump housing 508. A friction-reducing coating between the sheath 500 and housing component 510 may also facilitate re-advancement of the sheath 500 over the housing component 510 to collapse the pump housing 508 and inlet cannula 504 radially into the sheath 500 before device withdrawal. The inside lumen of the housing component 510 may also benefit from a friction reducing coating to allow for easier tracking over a previously placed guidewire and into the anatomy. Having a friction reducing coating on the inside of the drive shaft housing 511 may also facilitate the advancement of the rotatable inner catheter 700 through the drive shaft housing 511 and into the pump housing 508. Coating the drive shaft 704 with a friction reducing coating may reduce the resistance when spinning the rotatable inner catheter 700 that could lead to a reduction in drive shaft fatigue and abrasion, and may also result in an increase in the life span of the device.

Specifically regarding thrombus-reducing coatings, because the device is situated in blood and pumping blood throughout its components, there may be locations within the device where blood flow is stagnant. In these locations, it could be beneficial to apply a thrombus-reducing coating to the surface of these components to reduce the probability of any thrombus forming on the device or in the patient. One non-limiting example where it may be beneficial is on the interior of the drive shaft housing 511 where there may be minimal blood or fluid perfusion through the drive shaft housing 511.

Specifically regarding biocompatibility enhancing coatings, if the apparatus is being used as a long-term ventricular assist device, it may be beneficial to coat the components to improve biocompatibility. These coatings could function by making the devices less "visible" to the patient's body therefore reducing the chances of rejection. They may also function by reducing cell proliferation therefore reducing the rate of endothelialization on the device and increasing the usable lifespan of the apparatus. The notable components that may benefit from a biocompatibility improving coating are the housing component 510 and the sheath 500, though any of the other components may also benefit from one of these coatings.

With general reference to the two-part catheter systems that rotate relative to each other, there may be mechanisms to ensure optimal longitudinal alignment between the housing component 510 and the rotatable inner catheter 700, in accordance with embodiments of the subject matter disclosed herein. The pump impeller and pump housing may have a precise longitudinal alignment mechanism. A non-limiting example may be for the alignment mechanism to be controlled by adjusting the position between the hubs of the drive shaft and the drive shaft housing. The alignment mechanism may consist of the two hubs being locked in a static position therefore not allowing them to move freely, and then being able to precisely fine-tune their alignment. This fine tuning may be performed using a lead screw style mechanism where turning the screw causes the drive shaft to move distally or proximally in relation of the drive shaft housing therefore adjusting the impeller to pump housing positioning. The alignment mechanism may also use a fine adjustment thumb wheel style mechanism to precisely adjust the alignment between the components.

Another non-limiting example is for the alignment mechanisms to be controlled electronically to have increased precision of the alignment. With an electronic mechanism, it may be possible to have a worm gear coupled to a linear gear for increased precision and automatic position locking. An electronic alignment mechanism may allow the component alignment to be optimized by factoring in the current draw of the main motor driver and adjusting the component alignment to minimize the required current to rotate the impeller at a set rotational velocity.

An electronic alignment mechanism may allow the component alignment and the drive shaft tension to be optimized in real time as the rotational velocity of the impeller increases or decreases. As an example, as the rotational velocity increases, the self-centering functionality of the pump impeller may tend to thrust the impeller distally or proximally within the pump housing. As the impeller rotational velocity increases and the impeller tries to move, the electronic alignment mechanism may be adjusted to move the drive shaft proximally or distally, therefore maintaining the optimal impeller positioning within the pump housing. This real time alignment adjustment may be performed automatically if the alignment mechanism is motorized and communicates with the controller system to correctly adjust alignment based upon impeller rotational velocity.

The hubs of the drive shaft housing and the drive shaft may have a home position where they lock into place and the precise alignment mechanism engages. This home position may ensure the impeller is sufficiently well aligned within the pump housing to pump blood safely if not optimally. Then, once the device is on and rotating, the precise alignment mechanism may be used to optimize the component positioning by moving the impeller proximally or distally within the pump housing.

With general reference to catheter-based blood pumps, there may be alternate embodiments of the system, such as but not limited to daisy-chaining multiple pumping units in series, in accordance with embodiments of the subject matter disclosed herein. It is possible to daisy-chain multiple pumping units (inlet cannulas, pump housings, and impellers) on a single device. The outer catheter system may have multiple inlet cannulas and pump housings connected in series, and the drive shaft may have multiple impellers mounted in series around the shaft. All the impellers mounted on the single drive shaft may all rotate at the same angular velocity, therefore if it is desired to tailor flow dynamics for each pumping unit, the flow may be tailored by using differing impeller and pump housing geometry. Daisy-chaining multiple pumping units on a single device may allow the system to pump more blood with less damage to blood by rotating the impellers at a lower angular velocity. Each inlet cannula of a pumping unit may be located proximally of the distal pump housing's exit ports, therefore reducing backpressure the distal pumping unit needs to work against. A non-limiting example where the distal most pumping unit may have its inlet cannula located is within the left ventricle.

Due to a decreased backpressure against the distal pumping units when daisy-chaining pumping units together, the overall system may be able to support a higher fluid flow with a lower rotational angular velocity. Though this setup may result in a lower peak blood pressure at the distal most pump housing exit ports, the proximal pumping units may continue to increase the outlet blood pressure until the desired blood pressure and perfusion are achieved.

The proximal inlet cannulas and pump housings may be sized in a way to reduce back flow down the inside of the vessel from the pump housing exit ports back to the inlet cannulas. Additionally, blocking the back flow down the vessel may be achieved through each subsequent inlet cannula and pump housing junction having a skirt or petals that provide apposition against the vessel walls resulting in a reduction of the back flow through the vessel.

With general reference to the system controller, there are a plurality of features that may be included with a controller, in accordance with embodiments of the subject matter disclosed herein. The system controller may be a stationary piece of equipment or may be a portable system controller that is mobile with the patient. The controller is the brains of the system. The system controller may be a capital piece of equipment that communicates with and controls the motor used to rotate the impeller and pump blood. The controller may be capable of adjusting the rotational speed of the impeller (rpm) to control the cardiac output. It may as well monitor the motor parameters to ensure smooth device operation. Additionally, the controller may provide feedback of the device's performance and the patient's vitals to the user.

Based upon motor current draw, the impeller placement within the pump housing may be fine-tuned once running to allow for optimal efficiency of fluid flow to rotational rpm. The controller may also inform the user of the pump flow rate and by extension the amount of circulatory support the patient is receiving from the pump. This may be achieved by calculating device rpm to flow rate constant and calibrating the system with said constant.

During an acute procedure, the patient may be immobilized. Therefore, the controller may be a capital piece of equipment that is standalone next to the table where the patient is being treated. However, if the patient is receiving mechanical circulatory support for the treatment of cardiogenic shock or some other reason needing prolonged circulatory support, then a standalone system next to the patient's table is not convenient because it prevents the patient from having the freedom to move or get out of bed. Therefore, a portable controller system and motor may be preferred.

If an upper body access site is used to place the device, then the patient's legs may be free to allow them to be ambulatory if they can easily bring the motor and controller along with them. If a radial access site is used, the patient's arm will either have to be immobilized to prevent the device from shifting within the vasculature due to arm movement. For a radial access site, the patient may have a removable splint-style elbow and shoulder brace to immobilize their arm. The controller and motor may be strapped to the patient's arm thus allowing the full system to be contained on the patients arm and to be portable. Alternatively, when using a radial access site, the device may be immobilized within the vasculature, therefore allowing the patient to move their arm without the risk of displacing the device. Methods of immobilizing the device within the vasculature are discussed and depicted in the diagrams.

Alternatively, if an alternate upper body access site is used such as an axillary or subclavian artery access site, to name a few non-limiting examples, the patient may continue to move their arms, and torso without any risk of causing the device to move within the vasculature. For an axillary or similar access site, the patient may have the controller and motor either strapped directly to their shoulder, like and epaulette, or may have some of the components strapped to their thorax or abdominal area. A portable system may also be placed through an abdominal aortic artery ("AAA") access site, even though an AAA access site requires a surgical cutdown. If an AAA access site is used, then the portable system may be strapped onto a patient's waistband, or portions of the system may even be implanted internal to the patient's abdominal cavity.

A portable controller and motor system may be a single unit all housed together, or they may be separate units that are connected to each other. A few non-limiting examples of the motor and controller being separate may be having an internal implantable motor and having the controller external to the patient. Another example may be having an external motor connected to the patient's shoulder like an epaulette, and then having the controller attached to patient's abdominal area, or in a backpack the patient can carry around with them. The portable controller system may contain the electronics necessary to power the motor and to control the motor speed and monitor the patient and the devices performance.

The controller may be able to monitor the motor performance to determine if the motor is running efficiently or if it may be reaching the end of its life. By monitoring the motor performance, the controller may also be able to determine if the impeller to pump housing alignment is nominal or if it has shifted and needs adjustment. A portable controller may connect (wired or wirelessly) to additional external patient monitoring systems such as, but not limited to, a pulse-oximeter, EKG monitor, and blood pressure monitor to allow for a comprehensive, real-time monitoring of the patient's vitals and be able to adjust the devices performance for optimal patient health, or to inform the patient if they should seek medical treatment.

The portable controller may have data storage capacities to keep track of the device performance and any patient vitals that are also being monitored, this may assist a clinician by providing diagnostic data. This data may also assist with weening patients off mechanical circulatory support. The portable controller may monitor and interpret the data and have an alarm system to notify the patient if any device parameters or patient vitals are drifting from nominal, therefore it may allow for preemptive intervention instead of reactively addressing any issues. The alarm system may be visual, audible, tactile, or any combination thereof. The alarm system may also communicate wirelessly with the patient's clinician as well as with emergency medical services should any issues arise, thereby facilitating a rapid response time.

The controller may have the capabilities to adjust the magnitude of the mechanical circulatory support provided by the catheter-based blood pump. The controller may adjust the flow rate (e.g., the impeller rpm speed) based upon patient vitals such as blood pH levels, blood oxygenation levels, heart rate, blood pressure, etc. The portable controller may also have features to slowly decrease the rate of blood flow it provides while monitoring the patient's vitals, thereby slowly weening the patient off the mechanical circulatory support while ensuring the patient remains stable.

A portable controller may also have an adjustable parameter to allow the patient to adjust the flow rate of the blood pump. Flow rate adjustments may be limited to a specific pre-set range determined by their clinician. Allowing the patient to change the flow rate may allow them to have a mechanical circulatory support experience that is personally tailored to their lifestyle. For example, the patient may increase the flow rate if they are walking or exercising and then decrease the flow rate when they are resting, thereby potentially increasing the life span of the device and improving the patient's quality of life.

A portable controller needs a power source to run the motor and any device and patient monitoring systems. The portable controller may house a battery to run the system for a period while the controller is disconnected from an external power source. When connecting the portable controller to a power source, the portable controller may have plug adaptors that allow it to run off 220-110 VAC, or an adaptor that allows it to run off 12-24 VDC to power the system and motor. A low voltage DC adaptor may allow the controller to be powered from a mobile location like a vehicle. Additionally, portable modular battery packs may be supplied which can connect to the controller to power the system for prolonged periods during times when the patient is not around an external power source or in the case of a power outage at the location where the patient is located.

With general reference to the catheter-based blood pumps described herein, there are many varying use scenarios where a blood pump may support a patient's vitals and improve their outcome, in accordance with embodiments of the subject matter disclosed herein. The catheter-based blood pump will be used to provide mechanical circulatory support to patients who may need additional blood pumping capabilities and/or capacities. This may be used either as a long-term ventricular assist device or as a short-term device to perform protected PCI but is not restricted to these use scenarios. The invention can gain patient access either through a conventional femoral access site or through an upper body access site, for example a radial access site.

Using a radial access site may allow a patient to be ambulatory with the device still in place and pumping blood as long as their arm was immobilized, or the apparatus was immobilized within the ventricle/aorta. A radial access may also allow for the femoral arteries to be used for other concomitant procedures, such as but not limited to percutaneous angioplasty/stenting and lower limb revascularization.

Many alternate access sites may be used for placing the apparatus because a large bore access site is not required for placing the device within a patient. In addition to a radial or femoral artery access site, the access site may be in the femoral veins or in the brachial vessels. The axillary arteries may also be used as access sites for placement of the device. Additionally, in a blood pushing configuration, the device may be placed through a trans-thoracic/trans-apical approach and pump blood from the left ventricle into the aorta as seen in FIG. 4B.

The apparatus may be placed across the aortic valve and pump blood from the left ventricle into the aorta as illustrated in FIG. 3. In a blood pushing configuration the apparatus may be placed in the right ventricle and across the semi-lunar valve to pump blood into the pulmonary artery. A blood pushing configuration may also be placed in the left ventricle through a trans-septal access pathway as seen in FIG. 4A.

To provide general context, Table 1 (below) lists some example size ranges of various components of some embodiments of the percutaneous ventricular assist devices described herein. It should be understood, however, that these are non-limiting examples, and that the components are scalable to various other desired sizes and size ranges, both smaller and larger than listed in Table 1.

TABLE 1

| Introducer Sheath Compatibility | Collapsed Inlet Cannula and Pump Housing Diameters | Expanded Inlet Cannula Diameters | Expanded Pump Housing Diameters | Collapsed Impeller Diameters | Expanded Impeller Diameter |
|---|---|---|---|---|---|
| ≤6 Fr | <.078" | 9 Fr-21 Fr | 14 Fr-30 Fr | <.071" | 9 Fr-27 Fr |
| 7 Fr | .078-.090" | 12 Fr-24 Fr | 24 Fr-42 Fr | <.078" | 18 Fr-39 Fr |
| ≥8 Fr | >.090" | 12 Fr-30 Fr | 24 Fr-78 Fr | >.078" | 21 Fr-75 Fr |

The percutaneous ventricular assist devices described herein may be operated at various speeds (e.g., in terms of revolutions per minute ("rpm") of the pump impeller) in order to obtain the desired operational pumping rate performance. In some non-limiting example embodiments, the pump impeller of the percutaneous ventricular assist devices described herein may be operated in a range of 0 rpm to 10,000 rpm, or 5,000 rpm to 20,000 rpm, or 5,000 rpm to 30,000 rpm, or 5,000 rpm to 40,000 rpm, or 5,000 rpm to 50,000 rpm, or 10,000 rpm to 20,000 rpm, or 10,000 rpm to 30,000 rpm, or 10,000 rpm to 40,000 rpm, or 10,000 rpm to 50,000 rpm, or 10,000 rpm to 60,000 rpm, or 20,000 rpm to 30,000 rpm, or 20,000 rpm to 40,000 rpm, or 20,000 rpm to 50,000 rpm, or 20,000 rpm to 60,000 rpm, or 30,000 rpm to 40,000 rpm, or 30,000 rpm to 50,000 rpm, or 30,000 rpm to 60,000 rpm, or 40,000 rpm to 50,000 rpm, or 40,000 rpm to 60,000 rpm, or 50,000 rpm to 60,000 rpm, or greater than 60,000 rpm. It should be understood that these ranges of pump impeller rpms are purely exemplary and non-limiting as the actual impeller rpm used during a procedure will ultimately depend on many different factors such as, but not limited to, impeller design, pump system size, patient parameters, clinician preferences, and so on.

There are many additional use scenarios for a catheter-base blood pump to support patient blood circulation. A few non-limiting examples of device use are listed herein. The apparatus may be placed in the right ventricle and pump blood to the lungs to improve blood oxygenation circulation. This use scenario may be useful for short-term support during a pulmonary embolism, for example. The device may be placed in the carotid arteries to increase brain perfusion, this may be desired during a transient ischemic attack (ischemic stroke). The device may also be placed in the descending aorta to partially offload the blood backpressure against the heart and provide additional perfusion to the renal arteries and the legs. The device may be placed in the iliac arteries to help with an ischemic lower limb. In general, the blood pump may be place directly upstream of any specific organ, if additional blood perfusion would be helpful or is needed.

Two separate apparatuses may also be used in tandem for supporting dual organ systems simultaneously. An example of this would be to place one in the descending aorta to support the lower limbs while simultaneously placing one in the carotid arteries to maintain adequate blood pressure in the brain.

The devices described herein may be optionally MRI compatible. The drive shaft, and drive shaft housing may be made from an MRI safe support structure material, such as nitinol or PEEK etc., and the sheath, impeller and casing may also be MRI compatible, so the full implantable portion of the apparatus would be MRI compatible. Therefore, with an extended length drive shaft and drive shaft housing outside of the body it would be possible to provide patients with hemodynamic support during MRI imaging.

The devices described herein may be partially implanted if the clinician is un-certain whether mechanical circulatory support will be required during an intervention such as a protected PCI. Partial implantation consists of placing the housing component 510 within the patient, then either expanding the inlet cannula 504 and pump housing 508 or leaving them in their collapsed state. At this point, the clinician could continue the PCI procedure without turning on the blood pump. If the patient ends up not needing circulatory support during the procedure, the stationary outer catheter system can be removed without ever needing to use the rest of the pump assembly. If the patient does require circulatory support during the procedure, the rotatable inner catheter 700 can quickly be deployed in the already placed housing component 510 and the device turned on, thereby drastically reducing the delay from when circulatory support is needed to when the support is provided. Using a partial implantation technique of the device may provide significant cost savings by not requiring the catheter lab time for the complete device implantation as well as not needing to use the rotatable inner catheter 700. If the components are available separately then the clinician may replenish their inventory by replacing the housing component 510 and sheath 500.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. A percutaneous ventricular assist device comprising:
   an elongate flexible drive shaft defining a lumen;
   an inflatable balloon-based pump impeller attached to a distal end portion of the drive shaft, the pump impeller comprising:
   a tapered body with an outer surface; and
   one or more ridges comprising tubular balloons that have separate internal lumens and that are disposed around the outer surface of a distal portion of the tapered body,
   wherein the tapered body and the one or more ridges are expandable in response to receiving an inflation fluid supplied to the pump impeller via the lumen,
   wherein the tapered body has a maximum diameter portion located between a proximal portion of the tapered body and the distal portion of the tapered body, and
   wherein the one or more ridges are located only around the outer surface of the distal portion of the tapered body; and
   a pump housing,
   wherein percutaneous ventricular assist device is configured to pump blood when: (i) the pump impeller is positioned in the pump housing, (ii) the pump impeller is expanded, and (iii) the drive shaft is rotated.

2. The percutaneous ventricular assist device of claim 1, wherein the pump housing is reconfigurable between a low-profile delivery configuration and a radially expanded configuration, and wherein the pump housing defines one or more outlet openings.

3. The percutaneous ventricular assist device of claim 2, wherein the pump housing defines one or more relief cutouts around a periphery of each of the one or more outlet openings.

4. The percutaneous ventricular assist device of claim 1, further comprising an inlet cannula extending from the pump housing, and wherein the inlet cannula defines one or more inlet openings.

5. The percutaneous ventricular assist device of claim 4, wherein the inlet cannula is reconfigurable between a low-profile delivery configuration and a radially expanded configuration.

6. The percutaneous ventricular assist device of claim 1, further comprising a drive shaft housing extending proximally from the pump housing and defining a housing lumen configured to slidably receive the drive shaft and the pump impeller when the pump impeller is deflated.

7. The percutaneous ventricular assist device of claim 1, wherein the one or more ridges spiral around a central axis of the pump impeller.

8. The percutaneous ventricular assist device of claim 1, wherein the tapered body has a smaller outer diameter distally of the maximum diameter portion than proximally of the maximum diameter portion.

9. The percutaneous ventricular assist device of claim 1, wherein the proximal portion of the tapered body has a smooth outer surface.

10. The percutaneous ventricular assist device of claim 1, wherein the pump impeller has no internal support structure.

* * * * *